(12) United States Patent
Perrow et al.

(10) Patent No.: US 12,408,909 B2
(45) Date of Patent: Sep. 9, 2025

(54) APPARATUS AND METHOD FOR ENLARGING AN INCISION

(71) Applicant: Xtant Medical Holdings, Inc., Belgrade, MT (US)

(72) Inventors: Scott J. Perrow, Ishpeming, MI (US); Bruce Anthony Riceman, Leander, TX (US); Jacob Anton Colantonio, Marquette, MI (US)

(73) Assignee: XTANT MEDICAL HOLDINGS, INC., Belgrade, MT (US)

( * ) Notice: Subject to any disclaimer, the term of this patent is extended or adjusted under 35 U.S.C. 154(b) by 0 days.

(21) Appl. No.: 18/658,301

(22) Filed: May 8, 2024

(65) Prior Publication Data
US 2024/0285272 A1    Aug. 29, 2024

Related U.S. Application Data

(63) Continuation of application No. 17/526,766, filed on Nov. 15, 2021, now Pat. No. 11,980,356, which is a
(Continued)

(51) Int. Cl.
*A61B 17/02* (2006.01)
*A61B 1/32* (2006.01)
(Continued)

(52) U.S. Cl.
CPC ............ *A61B 17/0293* (2013.01); *A61B 1/32* (2013.01); *A61B 17/0206* (2013.01);
(Continued)

(58) Field of Classification Search
CPC . A61B 17/02; A61B 17/0206; A61B 17/0293; A61B 17/025; A61B 2017/0268; A61B 1/32
(Continued)

(56) References Cited

U.S. PATENT DOCUMENTS

| 2,473,266 A | 6/1949 | Wexler |
| 2,623,517 A | 12/1952 | Israel et al. |

(Continued)

FOREIGN PATENT DOCUMENTS

| WO | WO 03/086202 | 10/2003 |
| WO | WO 2004/047650 | 6/2004 |

(Continued)

OTHER PUBLICATIONS

Clarity Lateral, Retactor System, Surgical Technique, 2008, 12 pages.
(Continued)

*Primary Examiner* — Eduardo C Robert
*Assistant Examiner* — Christina Negrellirodriguez
(74) *Attorney, Agent, or Firm* — Sheridan Ross P.C.

(57) ABSTRACT

A retraction system and method are provided for retracting tissues surrounding a surgical site. In one aspect, a method including engaging slide connections between a guide dilator and a plurality of tissue engaging members and sequentially enlarging an incision using the guide dilator and the plurality of tissue engaging members. In another aspect, a method of inserting a plurality of tissue engaging members into an incision including fixing tip portions of the plurality of tissue engaging members in an insertion configuration, advancing the tip portions into an incision, and restricting movement of the tip portions away from the insertion configuration. A guide dilator system comprising an elongate body, a plurality of tissue engaging members, and slide connections between the elongate body and the tissue engaging members is also provided.

15 Claims, 67 Drawing Sheets

Related U.S. Application Data continuation of application No. 16/458,945, filed on Jul. 1, 2019, now Pat. No. 11,172,919, which is a continuation of application No. 15/991,502, filed on May 29, 2018, now Pat. No. 10,357,239, which is a continuation-in-part of application No. 15/382,192, filed on Dec. 16, 2016, now Pat. No. 9,980,714, which is a continuation of application No. 14/832,592, filed on Aug. 21, 2015, now Pat. No. 9,579,095, which is a continuation-in-part of application No. 14/250,063, filed on Apr. 10, 2014, now Pat. No. 9,113,852, which is a continuation of application No. 13/415,673, filed on Mar. 8, 2012, now Pat. No. 8,702,600.

(60) Provisional application No. 61/450,560, filed on Mar. 8, 2011.

(51) Int. Cl.
*A61B 17/00* (2006.01)
*A61B 90/00* (2016.01)
*A61B 90/30* (2016.01)

(52) U.S. Cl.
CPC .. *A61B 17/025* (2013.01); *A61B 2017/00261* (2013.01); *A61B 2017/00367* (2013.01); *A61B 2017/00407* (2013.01); *A61B 2017/00477* (2013.01); *A61B 2017/0256* (2013.01); *A61B 2017/0262* (2013.01); *A61B 90/03* (2016.02); *A61B 90/30* (2016.02); *A61B 2090/306* (2016.02)

(58) Field of Classification Search
USPC .................................................. 600/184–246
See application file for complete search history.

(56) References Cited

U.S. PATENT DOCUMENTS

| | | |
|---|---|---|
| 3,038,468 A | 6/1962 | Raeuchle |
| 3,724,449 A | 4/1973 | Gauthier |
| 3,948,259 A | 4/1976 | Bolduc et al. |
| 3,998,217 A | 12/1976 | Trumbull et al. |
| 4,010,741 A | 3/1977 | Gauthier |
| 4,434,791 A | 3/1984 | Darnell |
| 5,616,117 A | 4/1997 | Dinkler et al. |
| 5,667,481 A | 9/1997 | Villalta et al. |
| 5,688,223 A | 11/1997 | Rosendahl |
| 5,728,046 A | 3/1998 | Mayer et al. |
| 5,813,978 A | 9/1998 | Jako et al. |
| 5,928,139 A | 7/1999 | Koros et al. |
| 5,944,658 A | 8/1999 | Koros et al. |
| 5,954,635 A | 9/1999 | Foley et al. |
| 5,957,927 A | 9/1999 | Magee et al. |
| 5,967,973 A | 10/1999 | Sherts et al. |
| 6,083,154 A | 7/2000 | Liu et al. |
| 6,139,493 A | 10/2000 | Koros et al. |
| 6,206,826 B1 | 3/2001 | Mathews et al. |
| 6,213,940 B1 | 4/2001 | Sherts et al. |
| 6,224,545 B1 | 5/2001 | Cocchia et al. |
| 6,322,500 B1 | 11/2001 | Sikora et al. |
| 6,416,467 B1 | 7/2002 | McMillin et al. |
| 6,431,025 B1 | 8/2002 | Koros et al. |
| 6,464,634 B1 | 10/2002 | Fraser |
| 6,616,605 B2 | 9/2003 | Wright et al. |
| 6,800,084 B2 | 10/2004 | Davison et al. |
| 6,849,064 B2 | 2/2005 | Hamada |
| 6,869,398 B2 | 3/2005 | Obenchain et al. |
| 6,896,654 B2 | 5/2005 | Paolitto et al. |
| 6,932,764 B2 | 8/2005 | Kashyap |
| 7,195,592 B2 | 3/2007 | Ravikumar et al. |
| 7,780,594 B2 | 8/2010 | Hutton |
| 7,931,589 B2 | 4/2011 | Cohen et al. |
| 7,985,179 B2 | 7/2011 | Gephart et al. |
| 8,550,995 B2 | 10/2013 | Frasier et al. |
| 8,702,600 B2 | 4/2014 | Perrow |
| 8,882,661 B2 | 11/2014 | Hutton et al. |
| 8,956,285 B2 | 2/2015 | Gephart et al. |
| 9,113,852 B2 | 8/2015 | Perrow |
| 9,498,200 B2 | 11/2016 | Pfabe et al. |
| 9,579,095 B2 | 2/2017 | Perrow |
| 9,980,714 B2 | 5/2018 | Perrow |
| 10,285,680 B2 | 5/2019 | Friedrich et al. |
| 10,357,239 B2 | 7/2019 | Perrow et al. |
| 11,172,919 B2 * | 11/2021 | Perrow .............. A61B 17/0293 |
| 11,980,356 B2 | 5/2024 | Perrow et al. |
| 2002/0111538 A1 | 8/2002 | Wright et al. |
| 2002/0193666 A1 | 12/2002 | Sherts et al. |
| 2003/0191371 A1 | 10/2003 | Smith et al. |
| 2004/0002629 A1 | 1/2004 | Branch et al. |
| 2004/0059193 A1 | 3/2004 | Fanous |
| 2004/0087833 A1 | 5/2004 | Bauer et al. |
| 2004/0133077 A1 | 7/2004 | Obenchain et al. |
| 2004/0133201 A1 | 7/2004 | Shluzas et al. |
| 2004/0176665 A1 | 9/2004 | Branch et al. |
| 2004/0193018 A1 | 9/2004 | Thalgott et al. |
| 2004/0230100 A1 | 11/2004 | Shluzas |
| 2004/0242969 A1 | 12/2004 | Sherts et al. |
| 2005/0080320 A1 | 4/2005 | Lee et al. |
| 2005/0137461 A1 | 6/2005 | Marchek et al. |
| 2005/0149035 A1 | 7/2005 | Pimenta et al. |
| 2005/0159650 A1 | 7/2005 | Raymond et al. |
| 2005/0159651 A1 | 7/2005 | Raymond et al. |
| 2005/0192485 A1 | 9/2005 | Branch et al. |
| 2005/0215862 A1 | 9/2005 | Larson et al. |
| 2005/0215866 A1 | 9/2005 | Kim |
| 2005/0234304 A1 | 10/2005 | Dewey et al. |
| 2005/0261694 A1 | 11/2005 | Orton et al. |
| 2005/0277812 A1 | 12/2005 | Myles |
| 2006/0004261 A1 | 1/2006 | Douglas |
| 2006/0030858 A1 | 2/2006 | Simonson et al. |
| 2006/0052672 A1 | 3/2006 | Landry et al. |
| 2006/0074445 A1 | 4/2006 | Gerber et al. |
| 2006/0224044 A1 | 10/2006 | Marchek et al. |
| 2007/0010716 A1 | 1/2007 | Malandain et al. |
| 2007/0118022 A1 | 5/2007 | Hutton |
| 2007/0156025 A1 | 7/2007 | Marchek et al. |
| 2007/0161867 A1 | 7/2007 | Fowler, Jr. et al. |
| 2007/0238932 A1 | 10/2007 | Jones et al. |
| 2007/0282171 A1 | 12/2007 | Karpowicz et al. |
| 2008/0033251 A1 | 2/2008 | Araghi |
| 2008/0188718 A1 * | 8/2008 | Spitler ............... A61B 17/0206 600/232 |
| 2008/0214898 A1 | 9/2008 | Warren |
| 2009/0069635 A1 | 3/2009 | Gephart et al. |
| 2015/0209022 A1 | 7/2015 | Ruppert et al. |
| 2016/0174997 A1 | 6/2016 | Spitznagel |
| 2016/0331431 A1 | 11/2016 | Gephart |
| 2018/0029824 A1 | 2/2018 | Gephart et al. |

FOREIGN PATENT DOCUMENTS

| | | |
|---|---|---|
| WO | WO 2005/092206 | 10/2005 |
| WO | WO 2005/094695 | 10/2005 |
| WO | WO 2005/096735 | 10/2005 |
| WO | WO 2007/087536 | 8/2007 |
| WO | WO 2008/039427 | 4/2008 |
| WO | WO 2014/140100 | 9/2014 |

OTHER PUBLICATIONS

ProAccess Radiolucent Retractor Blades, Sythes Spine, product offerings guide provided by the manufacturer, 2004, 2 pages, Paoli, Pennsylvania.

SynFrame Access and Retractor System Assembly Guide, Synthes Spine, assembly guide provided by the manufacturer, 1999, 12 pages, Paoli, Pennsylvania.

Webb, J., Spine-the future, AO foundation Webpage, available at: http://www.aofoundation.org/AOFileServer/PortalFiles?FilesPath=/Extranet2007/active/_att/wor/act/Dialogue/1999_2/spine.pdf, accessed Apr. 10, 2009.

(56) References Cited

OTHER PUBLICATIONS

TeDan Surgical Innovations, Phantom XL Series brochure, copyright dale 2013, 2 pages.
Official Action for U.S. Appl. No. 13/415,673, dated Feb. 4, 2013, 10 pages.
Official Action for U.S. Appl. No. 13/415,673, dated Sep. 16, 2013, 9 pages.
Notice of Allowance for U.S. Appl. No. 13/415,673, dated Dec. 5, 2013, 7 pages.
Official Action for U.S. Appl. No. 14/250,063, dated Jul. 1, 2014, 10 pages.
Official Action for U.S. Appl. No. 14/250,063, dated Jan. 28, 2015, 8 pages.
Notice of Allowance for U.S. Appl. No. 14/250,063, dated Apr. 20, 2015, 5 pages.
Official Action for U.S. Appl. No. 14/832,592, dated Oct. 30, 2015, 6 pages.
Official Action for U.S. Appl. No. 14/832,592, dated May 9, 2016, 8 pages.
Notice of Allowance for U.S. Appl. No. 14/832,592, dated Aug. 11, 2016, 12 pages.
Notice of Allowance for U.S. Appl. No. 14/832,592, dated Jan. 24, 2017, 3 pages.
Notice of Allowance for U.S. Appl. No. 15/382,192, dated Jan. 26, 2018, 11 pages.
Official Action for U.S. Appl. No. 15/991,502, dated Aug. 7, 2018, 8 pages.
Notice of Allowance for U.S. Appl. No. 15/991,502, dated Mar. 11, 2019, 5 pages.
Official Action for U.S. Appl. No. 16/458,945, dated Mar. 23, 2021, 8 pages.
Notice of Allowance for U.S. Appl. No. 16/458,945, dated Jul. 15, 2021, 7 pages.
Notice of Allowance for U.S. Appl. No. 17/526,766, dated Dec. 22, 2023, 12 pages.
U.S. Appl. No. 13/415,673, filed Mar. 8, 2012, now issued as U.S. Pat. No. 8,702,600.
U.S. Appl. No. 14/250,063, filed Apr. 10, 2014, now issued as U.S. Pat. No. 9,113,852.
U.S. Appl. No. 14/832,592, filed Aug. 21, 2015, now issued as U.S. Pat. No. 9,579,095.
U.S. Appl. No. 15/382,192, filed Dec. 16, 2016, now issued as U.S. Pat. No. 9,980,714.
U.S. Appl. No. 15/991,502, filed May 29, 2018, now issued as U.S. Pat. No. 10,357,239
U.S. Appl. No. 16/458,945, filed Jul. 1, 2019, now issued as U.S. Pat. No. 11,172,919.
U.S. Appl. No. 17/526,766, filed Nov. 15, 2021, now issued as U.S. Pat. No. 11,980,356.

* cited by examiner

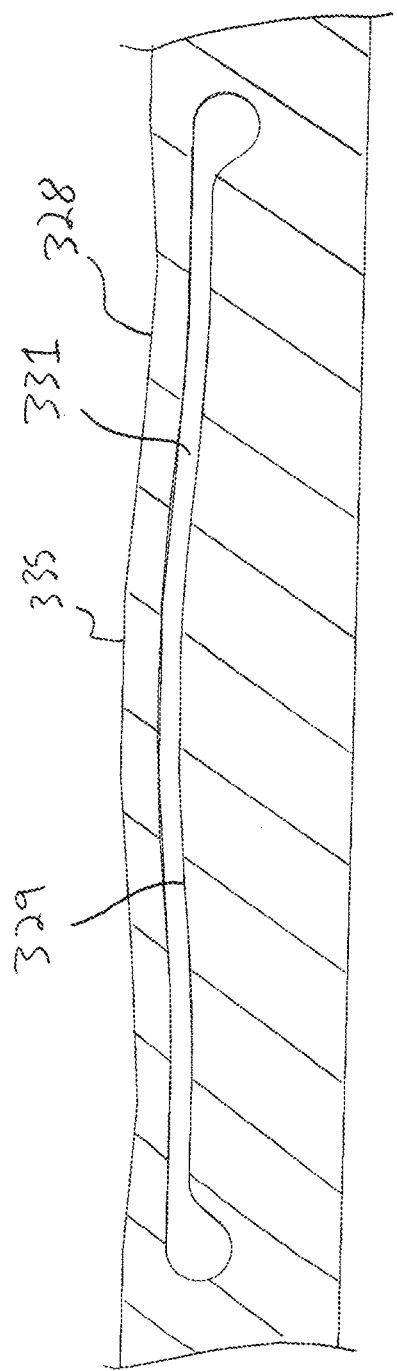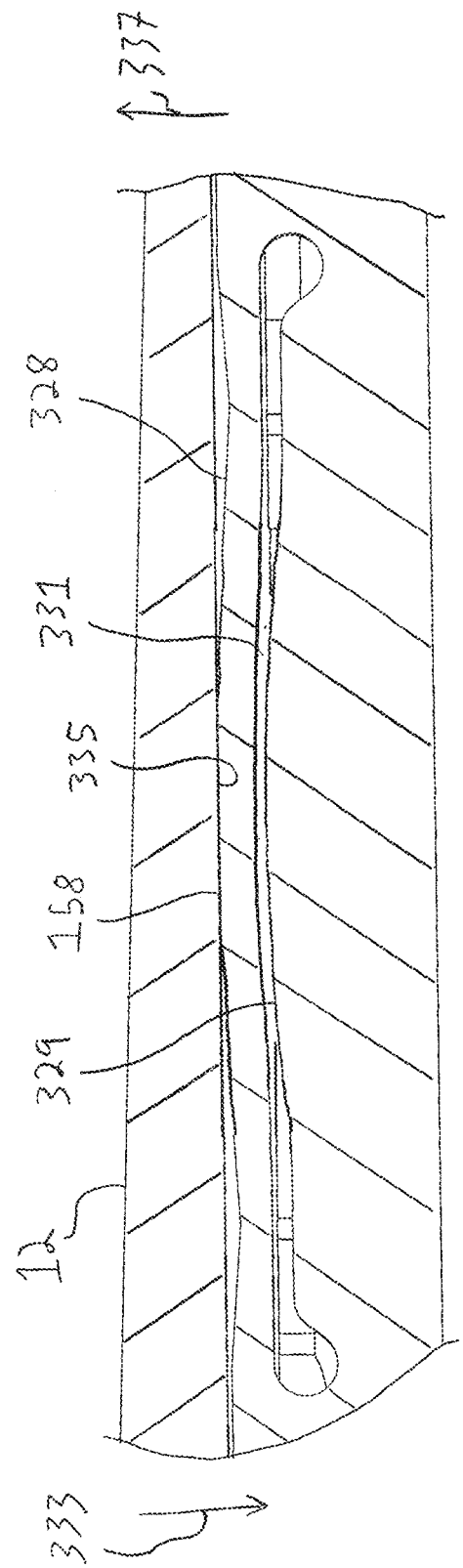

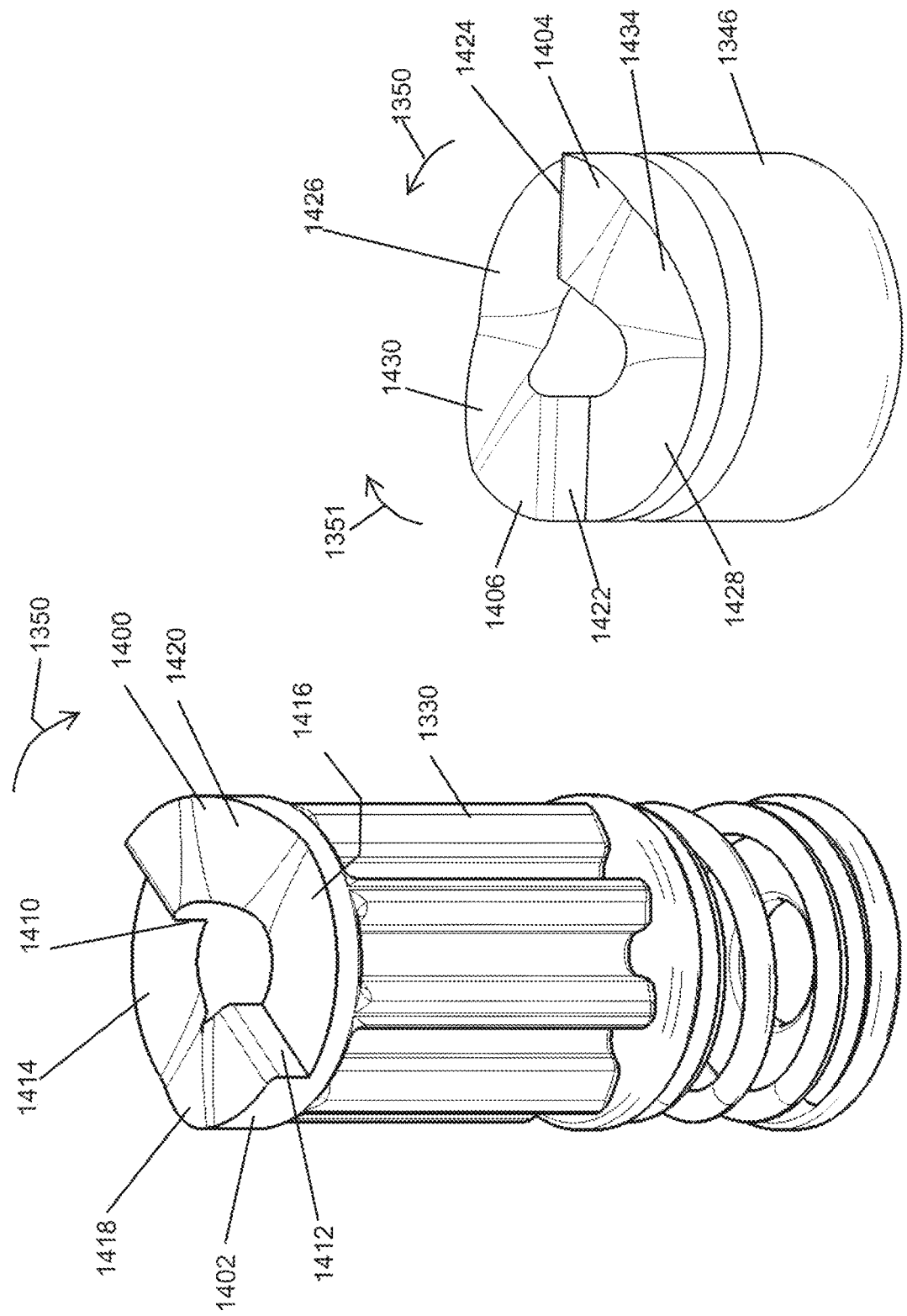

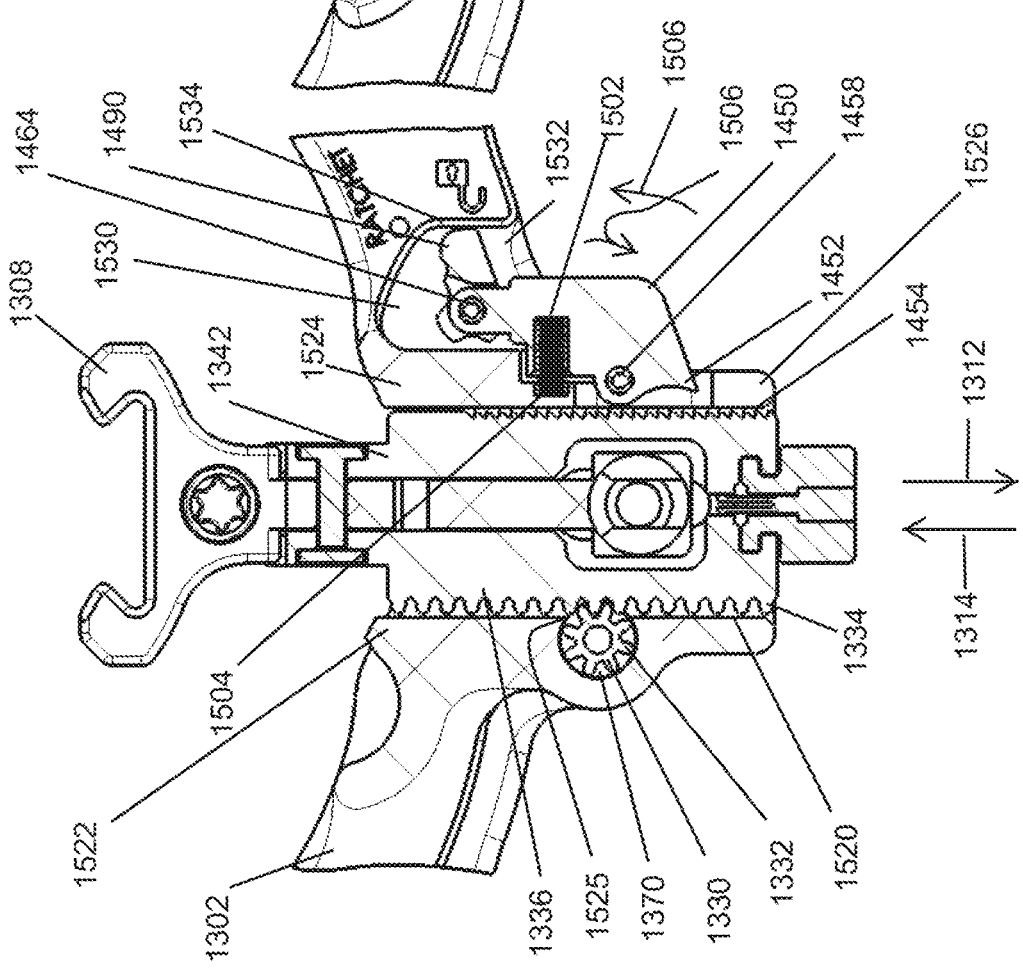

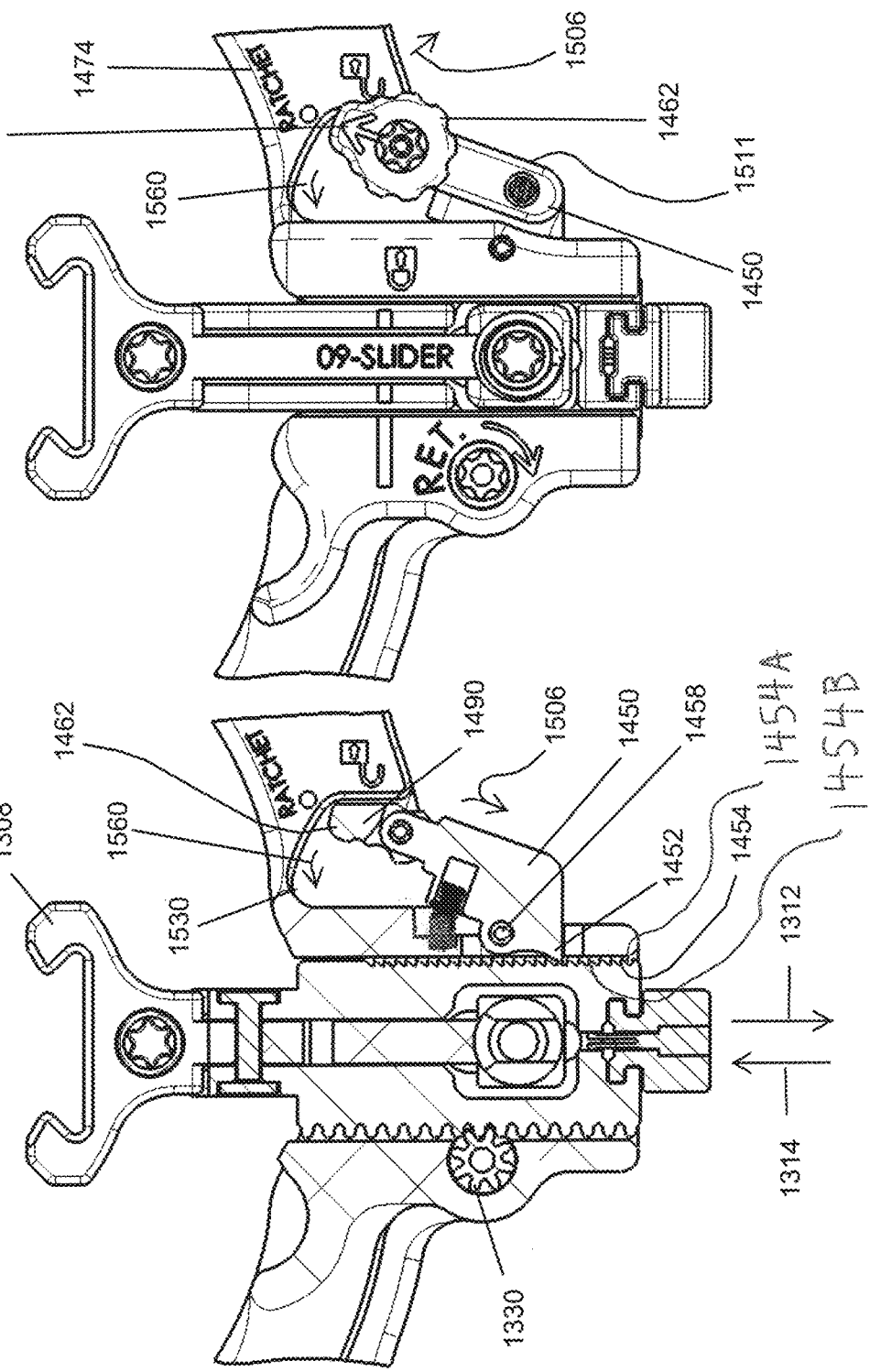

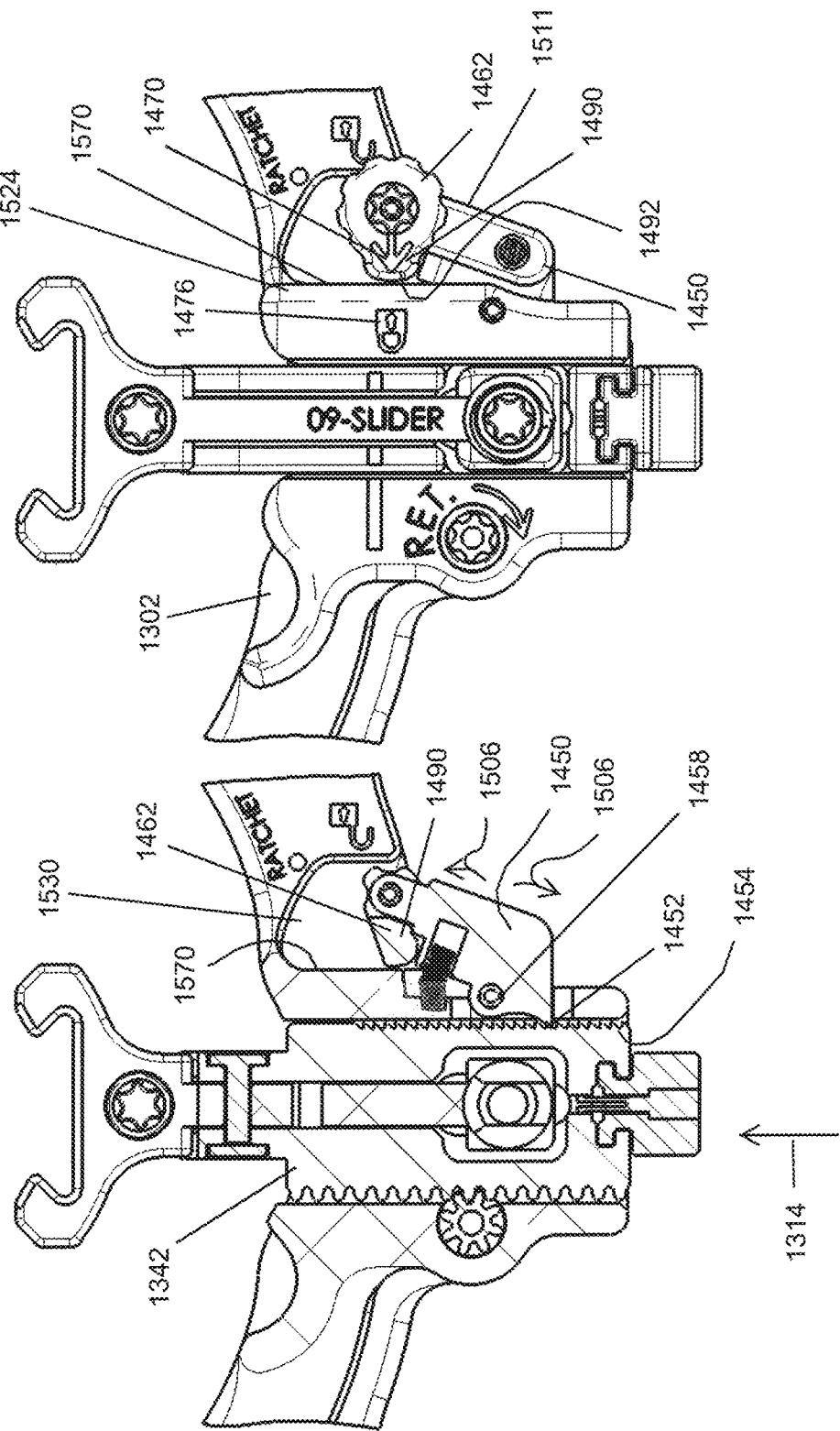

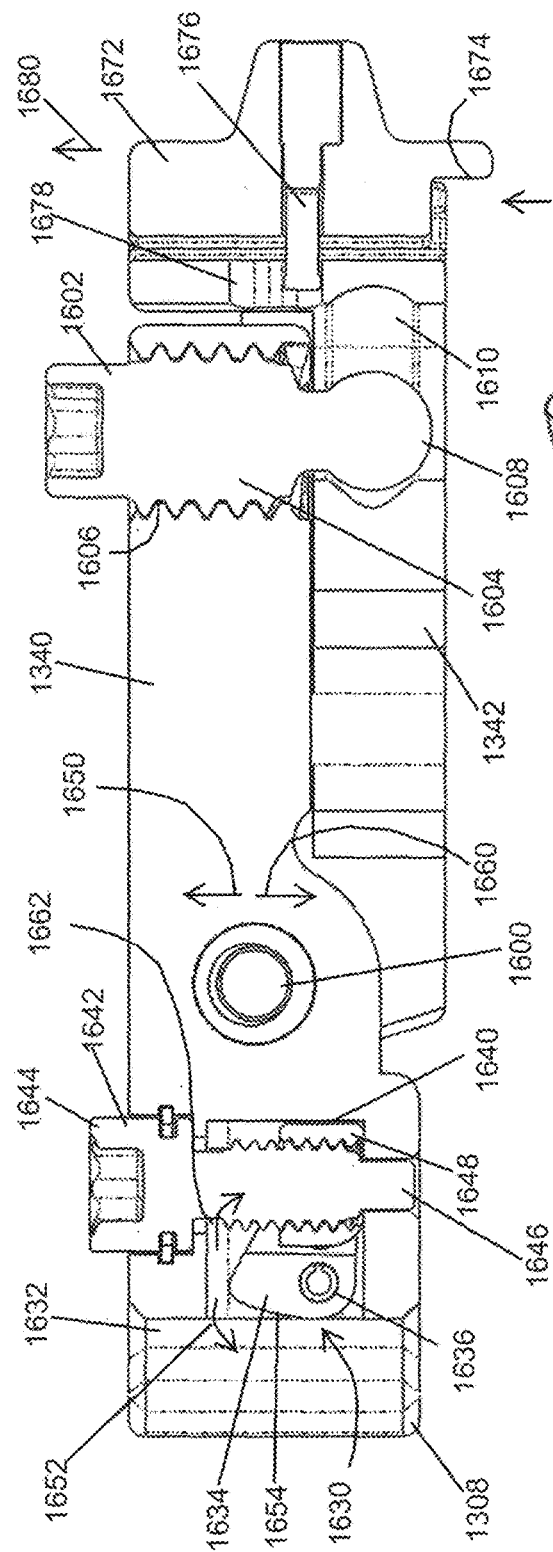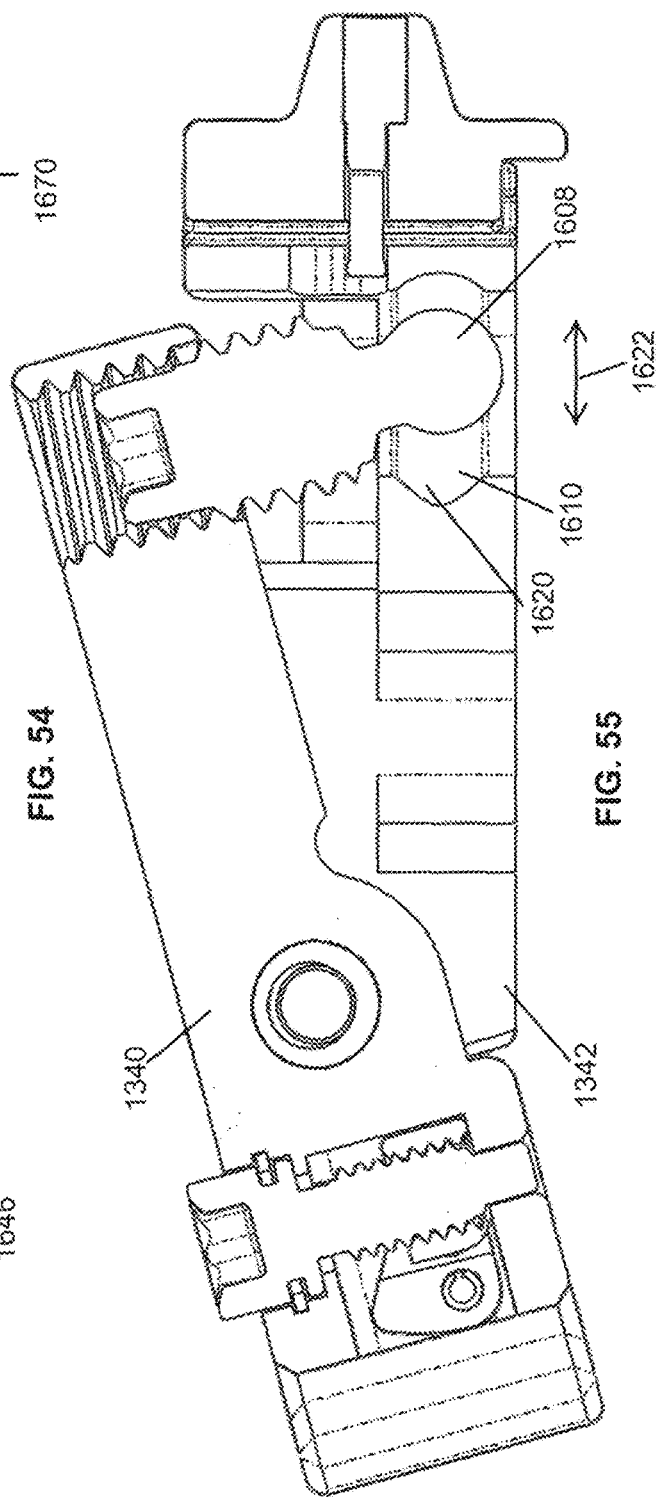
FIG. 54
FIG. 55

APPARATUS AND METHOD FOR ENLARGING AN INCISION

CROSS-REFERENCE TO RELATED APPLICATIONS

This application is a continuation of U.S. patent application Ser. No. 17/526,766, filed Nov. 15, 2021, now U.S. Pat. No. 11,980,356, which is a continuation of U.S. patent application Ser. No. 16/458,945, filed Jul. 1, 2019, now U.S. Pat. No. 11,172,919, which is a continuation of U.S. patent application Ser. No. 15/991,502, filed May 29, 2018, which issued as U.S. Pat. No. 10,357,239 on Jul. 23, 2019, which is a continuation-in-part of U.S. patent application Ser. No. 15/382,192, filed Dec. 16, 2016, which issued as U.S. Pat. No. 9,980,714 on May 29, 2018, which is a continuation of U.S. patent application Ser. No. 14/832,592, filed Aug. 21, 2015, which issued as U.S. Pat. No. 9,579,095 on Feb. 28, 2017, which is a continuation-in-part of U.S. patent application Ser. No. 14/250,063, filed Apr. 10, 2014, which issued as U.S. Pat. No. 9,113,852 on Aug. 25, 2015, which is a continuation of U.S. patent application Ser. No. 13/415,673, filed Mar. 8, 2012, which issued as U.S. Pat. No. 8,702,600 on Apr. 22, 2014, which claims the benefit of U.S. Provisional Patent Application No. 61/450,560, filed Mar. 8, 2011, all of which are hereby incorporated by reference in their entireties.

FIELD OF THE INVENTION

The invention relates to a system and method for providing access to a surgical site and, more particularly, to a system and method for retracting tissue during a surgical procedure.

BACKGROUND OF THE INVENTION

Advancing blades of a surgical retractor through an incision and into position adjacent a surgical site involves overcoming resistance from muscles, tendons, and other tissues within the body. When the surgical retractor is used to access a patient's spine from the side of the patient, known as lateral approach surgery, the distance to the patient's spine is greater than if the spine were accessed through the patient's back, known as posterior approach surgery. The increased distance to the spine during lateral approach surgery means overcoming a greater amount of resistance from muscles, tendons, and other tissues in order to advance the retractor blades to the surgical site than in a posterior approach surgery.

Another difficulty with lateral approach surgery is that the tissues surrounding the retractor blades tightly envelop and deflect the blades as the blades are slid along a dilator toward the surgical site. The increased distance to the spine for lateral approach surgery means that the retractor blades must be longer in order to retract tissues adjacent the surgical site. Like cantilever beams, the longer retractor blades used for lateral approach surgery are subjected to forces from the surrounding tissues that deflect the blades a greater amount than if the blades were shorter blades typically used for posterior approach surgery. Deflection of the long retractor blades allows the tissues enveloping the blades to lodge between the blades and the dilator as well as creep into gaps between the blades. The retractor blades may have to be removed and re-inserted into the patient to remove tissues caught between the blades and the dilator or caught in gaps between the blades, which complicates the surgical procedure.

For longer length blades, such as the 80 mm-180 mm blades typically used for lateral approach surgery, small manufacturing variations in straightness along the blades are magnified by the length of the blades. These variations are problematic, as even a slight curvature may cause the tip of a longer blade to lift up from the dilator and trap tissue as the blade is advanced toward the surgical site. Variations in blade straightness may also cause the tips of the retractor blades to be unevenly spaced around the dilator and permit tissue creep between the retractor blades. These situations increase the difficulty of advancing the retractor blades toward the surgical site and complicate the process of establishing a working channel to the spine.

SUMMARY OF THE INVENTION

In one aspect of the invention, a method is provided for enlarging an incision that limits tissue creep as tissue engaging members are advanced into an incision and substantially improves the ease with which a surgeon may establish a working channel within a patient. More specifically, the method involves engaging slide connections between a plurality of tissue engaging members and a guide dilator which restricts separation of the tissue engaging members and accompanying tissue creep therebetween. Engaging slide connections between the tissue engaging members and the guide dilator also limits tissues lodging between the tissue engaging members and the guide dilator by resisting separation of the tissue engaging members from the guide dilator. Further, the method involves advancing a leading end portion of the guide dilator into the incision to enlarge the incision to an initial opening and advancing distal end portions of the tissue engaging members connected to the guide dilator into the incision to enlarge the initial opening to a larger, intermediate-sized opening. In this manner, the leading end portion of the guide dilator and the distal end portions of the tissue engaging members sequentially dilate the incision and minimize strain on tissues surrounding the incision. In one approach, the method further comprises withdrawing the leading end portion of the guide dilator from the incision while restricting movement of the plurality of the tissue engaging members. This disengages the slide connections between the plurality of tissue engaging members and the guide dilator without having to individually disconnect the tissue engaging members or utilize another tool to disconnect the tissue engaging members from the guide dilator. Accordingly, the present method provides an easier and faster approach for advancing tissue engaging members into position adjacent a surgical site while limiting interference from bodily tissues.

In another aspect of the invention, a method is provided for inserting tissue engaging members into an incision that limits tissue creep even if the tissue engaging members are longer and have varying degrees of straightness. The method includes fixing tip portions of the tissue engaging members in a predetermined insertion configuration and advancing the tip portions into an incision. This way, any variation in the straightness of one or more of the tissue engaging members is compensated for by manipulating the associated tip portion(s) into the predetermined insertion configuration before the tip portions are advanced into the incision. The method further comprises restricting movement of the tip portions of the tissue engaging members away from the insertion configuration. In this manner, the tip portions may be held in the insertion configuration against resistance from bodily tissues as the tip portions are advanced within the patient. In one approach, fixing the tip portions of the plurality of tissue engaging members comprises engaging slide connections between the tissue engaging members and a guide dilator. The slide connections permit a surgeon to rapidly connect the tissue engaging members to the guide dilator and insert the guide dilator and tissue engaging members into the incision without muscle, tendons, or other tissues shifting the tip portions of the tissue engaging members from the predetermined insertion configuration.

A guide dilator system is also provided including an elongate body, a plurality of tissue engaging members, and slide connections between the elongate body and the plurality of tissue engaging members. In this manner, the tissue engaging members can be easily engaged with the elongate body, advanced into an incision, and disengaged from the elongate body adjacent a surgical site. In one form, the slide connections comprise axially extending surfaces of each slide connection that extend a majority of a predetermined length of the respective tissue engaging members with the tissue engaging members in an operative position. In this manner, the slide connections provide a firm engagement between the tissue engaging members and the elongate body when the tissue engaging members are in an operative position on and connected to the elongate body.

The elongate body and the tissue engaging members may further include stop portions configured to abut and limit sliding of the tissue engaging members along the elongate body in a predetermined direction. For example, the predetermined direction can be from a leading end portion of the elongate body toward a trailing end portion of the elongate body. As the leading end portion of the elongate body is advanced toward the surgical site, the stop portions of the elongate body and the tissue engaging members abut and keep the tissue engaging members from sliding off of the elongate body as the surrounding tissues resist movement of the elongate body and the tissue engaging members within the patient. Once the tissue engaging members are positioned adjacent a surgical site, the elongate body is withdrawn from the incision which slides the tissue engaging members off of the elongate body. In this manner, the guide dilator system can simplify and accelerate the process of advancing the tissue engaging members into position adjacent a surgical site.

BRIEF DESCRIPTION OF THE DRAWINGS

FIG. 7A is a cross sectional view taken across line 7A-7A in FIG. 7 showing a resilient member of one of the mounting rails of the guide dilator of FIG. 7;

FIG. 7B is a cross sectional view similar to FIG. 7A showing the resilient member deflected downward and engaged with a retractor blade connected to the mounting rail;

FIG. 45 is a top perspective view of the pinion of FIG. 44 showing an upper portion of the pinion having inclined cam surfaces and vertically extending drive surfaces;

FIG. 46 is a bottom perspective view of the drive cap of FIG. 44 showing inclined cam surfaces and vertically extending drive surfaces;

FIG. 48 is a cross-sectional view taken across line 48-48 in FIG. 42 showing the lock latch in an unlocked position and the tooth of the button disengaged from the slider;

FIG. 49 is a top plan view of the portion of the retractor of FIG. 48 showing the lock latch received in a cavity of the frame and abutting a wall of the cavity;

FIG. 50 is a cross-sectional view similar to FIG. 48 showing the lock latch pivoted to a ratchet position and the tooth of the button engaged with the slider;

FIG. 51 is a top plan view of the portion of the retractor of FIG. 50 showing the lock latch in the ratchet orientation and the lock latch having clearance within the frame cavity to permit the lock latch to pivot back and forth with the button as the tooth thereof ratchets in and out of depressions of the slider;

FIG. 52 is a cross-sectional view similar to FIG. 48 showing the lock latch pivoted to a locked position such that the lock latch abuts a surface of the frame and the tooth of the button is fixed in engagement in a depression of the slider;

FIG. 53 is a top plan view of the portion of the retractor of FIG. 52 showing the lock latch holding the button and tooth thereof in fixed engagement with the slider;

FIG. 54 is a cross-sectional view taken across line 54-54 in FIG. 43 showing an inner member of the slider in an initial configuration;

FIG. 55 is a cross-sectional view similar to FIG. 54 showing an elevation screw of the slider having been rotated to pivot the inner member to an inclined orientation relative to an outer member of the slider;

DETAILED DESCRIPTION OF THE PREFERRED EMBODIMENTS

In FIGS. 1-6, a guide dilator 10 for inserting tissue engaging members, such as retractor blades 12, 14, 16, 18, through an incision and into position adjacent a surgical site is provided. The guide dilator 10 provides a rigid support for the retractor blades 12, 14, 16, 18 as the guide dilator 10, and the retractor blades 12, 14, 16, 18 connected thereto, slide along one or more initial dilators 516, 520 (see FIG. 12) into position adjacent a surgical site. The guide dilator 10 supports the retractor blades 12, 14, 16, 18 against resistance from muscles, tendons, and other tissues and to limit splaying of the retractor blades 12, 14, 16, 18 as they are advanced along the guide dilator 10 into the incision. In this manner, the guide dilator 10 allows a surgeon to easily advance the retractor blades 12, 14, 16, 18 into an incision without the retractor blades 12, 14, 16, 18 shifting and permitting tissues to encroach into gaps between the blades 12, 14, 16, 18.

Figure 1:
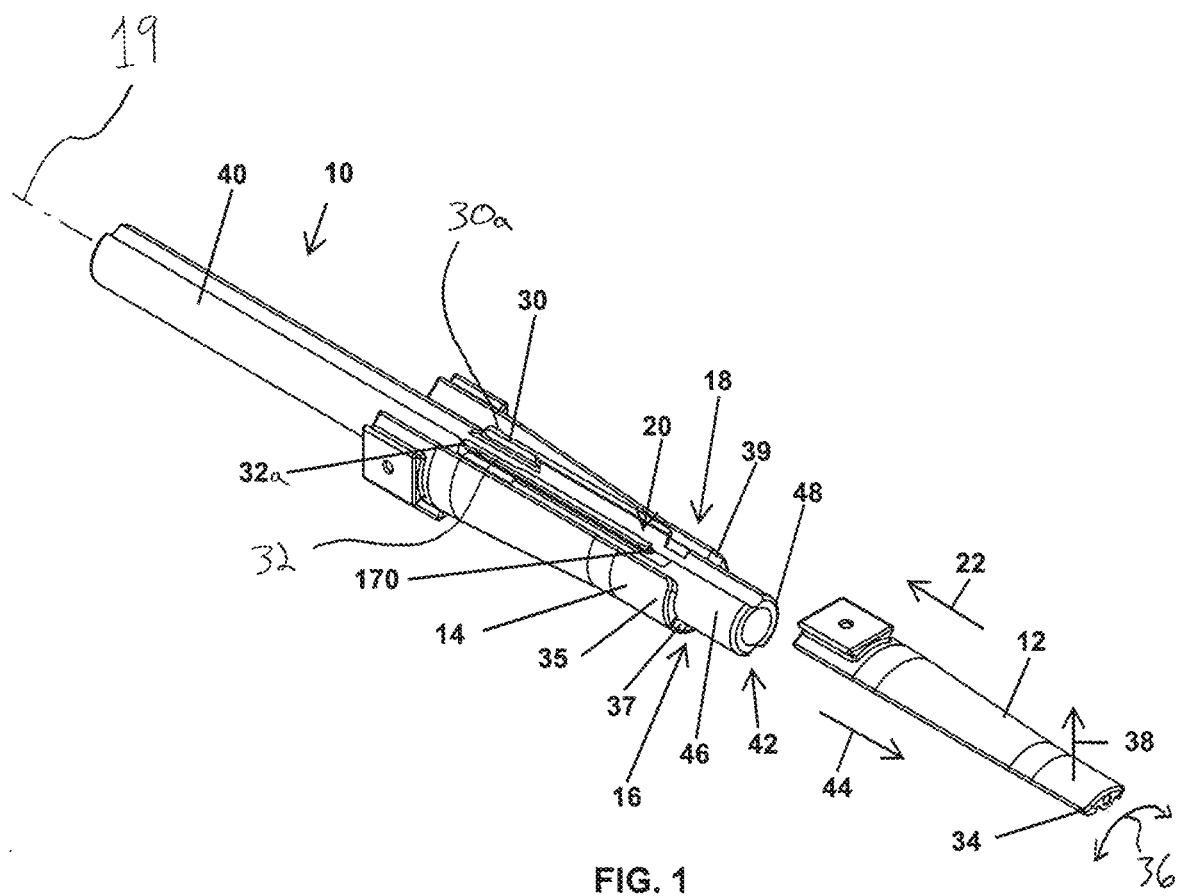
FIG. 1 is a perspective view of a guide dilator and retractor blades in accordance with one form of the present invention showing one of the retractor blades slid off of the guide dilator.

With reference to FIG. 1, the guide dilator 10 has a generally tubular configuration extending along a longitudinal axis 19. Further, the guide dilator 10 has slide connections with the retractor blades 12, 14, 16, 18, such as a mounting rail 20 that is received in sliding engagement in a slot 190 (see FIG. 5) on the blade 12, which permit the blades 12, 14, 16, 18 to be easily slid onto the guide dilator 10 in direction 22 and off of the guide dilator 10 in direction 44, as shown in FIG. 1. This way, the guide dilator 10 and blades 12, 14, 16, 18 can be rapidly and securely assembled during a surgery. The slide connections have stop portions, such as a lower end wall 170 of the mounting rail 20 and a stop surface 174 (see FIG. 5) of the blade 12, which are configured to abut and keep the blades 12, 14, 16, 18 from sliding off of the guide dilator 10 in direction 22 as tissues resist movement of the blades 12, 14, 16, 18 into an incision.

Figure 5:
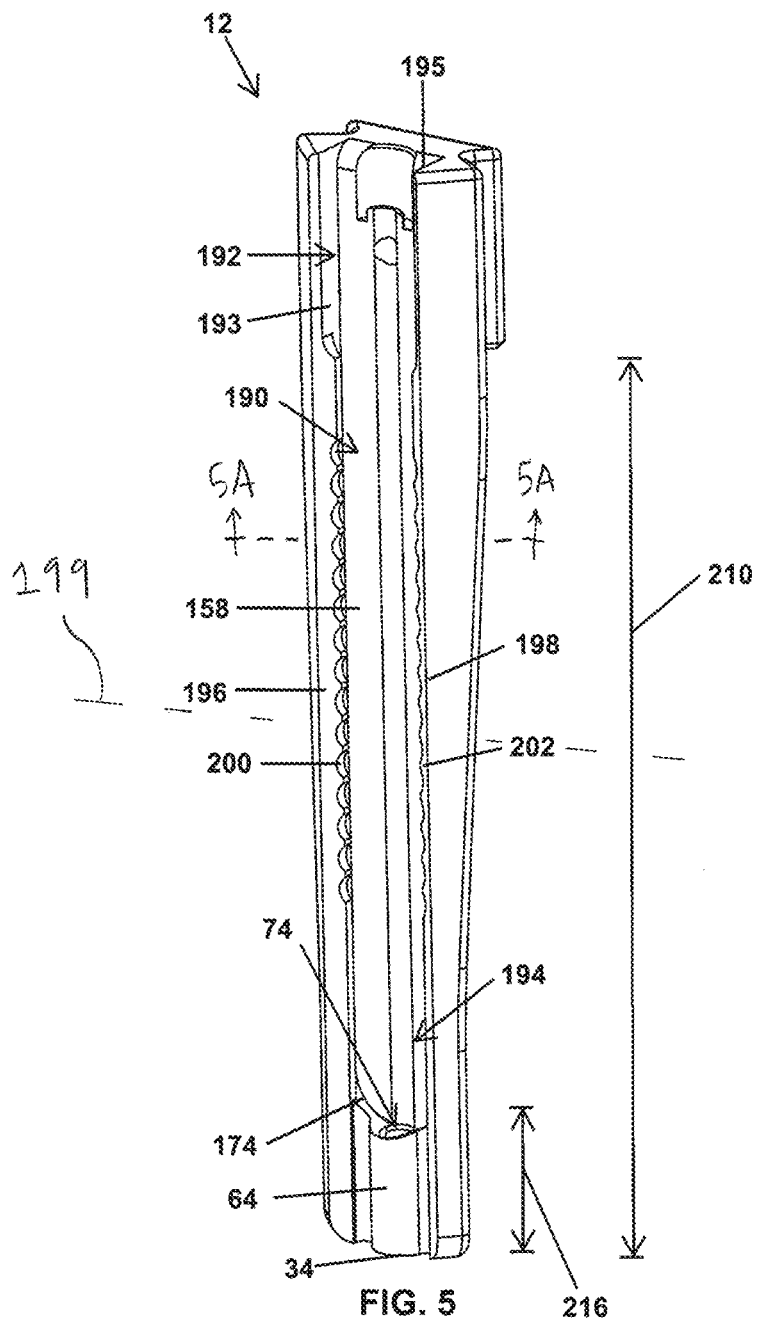
FIG. 5 is a perspective view of one of the retractor blades of FIG. 1 showing a slot of the blade for slidably receiving a mounting rail of the guide dilator and a cannula disposed at the distal end of the retractor blade.

In one form, the guide dilator 10 has a tissue engaging member retention mechanism, such as resilient arms 30, 32 of the mounting rail 20 which have distal ends 30a, 30b configured to be spaced apart by a distance that is greater than a width of the slot 190 of retractor blade 12 (see FIG. 5). When the blade 12 is slid onto mounting rail 20, the blade 12 deflects the distal ends 30a, 30b of the arms 30, 32 toward each other. The deflected arms 30, 32 resiliently bias against and frictionally engage surfaces 193, 195 of the slot 190. In this manner the tissue engaging member retention mechanisms engage the blades 12, 14, 16, 18 and provide resistance to removal of the blades 12, 14, 16, 18 from the guide dilator 10, as shown in FIG. 1. The frictional resistance is sufficient to keep the blades 12, 14, 16, 18 engaged with the guide dilator 10 when the guide dilator 10 is assembled and handled within the operating room, but permit the blades 12, 14, 16, 18 to be slid off of the guide dilator 10 when the blades 12, 14, 16, 18 are at a desired position within a patient. In this manner, the guide dilator 10 provides an elegant solution to the problem of handling the retractor blades 12, 14, 16, 18 throughout a surgical procedure.

A trailing end portion 40 of the guide dilator 10 is grasped after the retractor blades 12, 14, 16, 18 are mounted on the guide dilator 10 and a leading end portion 42 of the guide dilator 10 is advanced into an incision in direction 44, as shown in FIG. 1. Once the leading end portion 42 reaches the surgical site through the incision, the blades 12, 14, 16, 18 are slid downward in direction 44 along an outer bearing surface 46 of the leading end portion 42 until distal ends of the retractor blades 12, 14, 16, 18 reach an end 48 of the guide dilator 10. Next, a surgical retractor is connected to the blades 12, 14, 16, 18 to hold the retractor blades stationary in the incision and the guide dilator 10 is withdrawn from the incision in direction 22. The relative movement between the guide dilator 10 and the retractor blades 12, 14, 16, 18 withdraws guide dilator mounting rails 20, 92, 94, 96 (see FIG. 3) from associated slots in the blades 12, 14, 16, 18 and disengages the guide dilator 10 from the blades 12, 14, 16, 18. In this manner, moving the guide dilator 10 in a linear motion in direction 44 into an incision advances the connected retractor blades 12, 14, 16, 18 to a desired position adjacent a surgical site, and a reverse, linear motion in direction 22 disengages the guide dilator 10 from the blades 12, 14, 16, 18 and withdraws the guide dilator 10 from the incision in a single linear motion. As is apparent, this is an intuitive and speedy procedure for inserting retractor blades into position adjacent a surgical site.

With reference to the blade 12 in FIG. 1, the connection between the retractor blade 12 and the mounting rail 20 holds a tip 34 of the blade 12 against sliding in rotary direction 36 around the guide dilator 10 and radially away from the guide dilator 10 in direction 38. The connections between the mounting rails 92, 94, 96 and the blades 14, 16, 18 similarly limit movement of tips 35, 37, 39 of the blades 14, 16, 18 around and radially away from the guide dilator 10. In contrast to some previous techniques, where tissues could shift retractor blades as the blades were slid along a dilator into an incision, the guide dilator 10 holds retractor blade tips 34, 35, 37, 39 in a predetermined orientation around the guide dilator 10 against deflection and tissue creep until the guide dilator 10 is disengaged from the retractor blades 12, 14, 16, 18.

Figure 2:
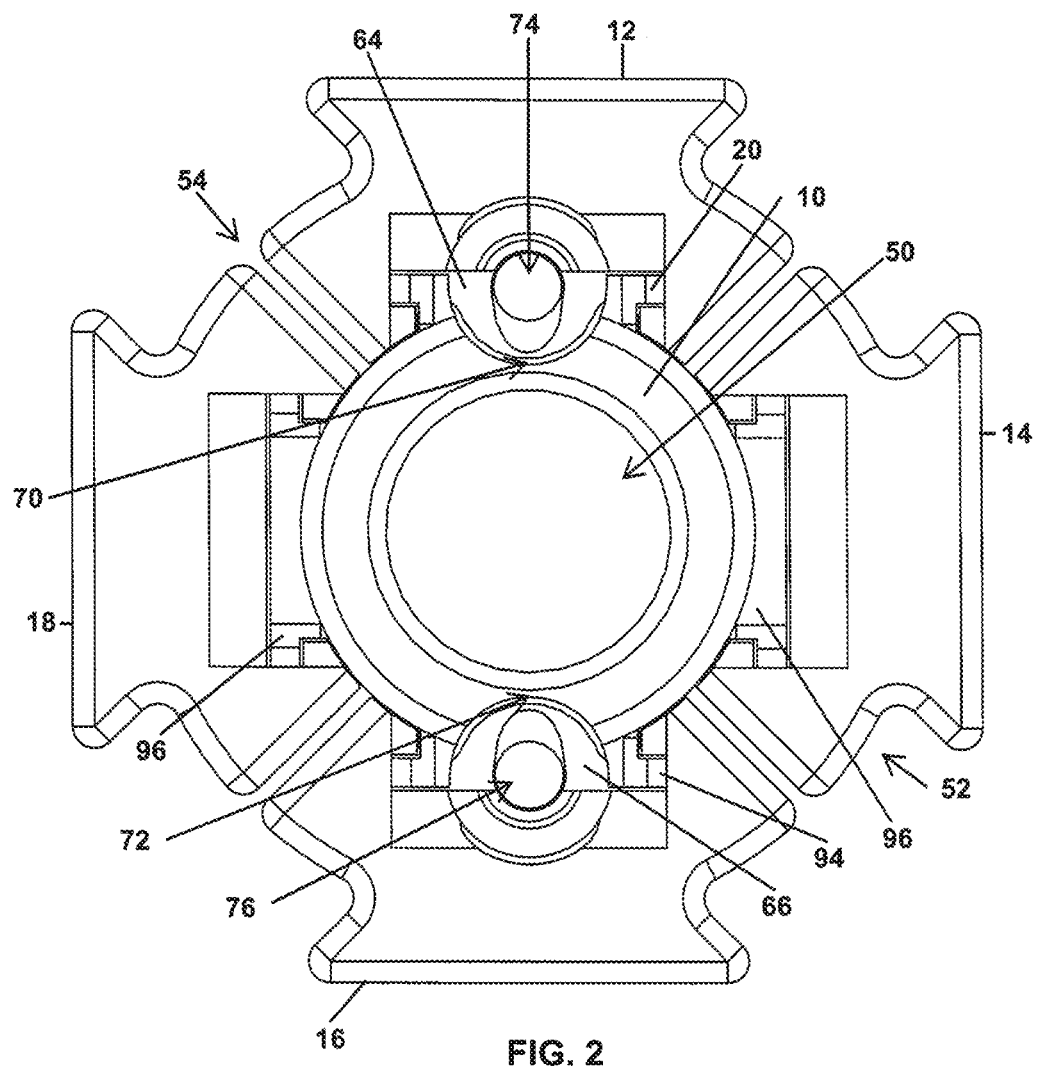
FIG. 2 is an enlarged, end view of the guide dilator of FIG. 1 with all of the retractor blades connected to the guide dilator showing an outer profile of the retractor blades.

Turning to FIG. 2, the guide dilator 10 has a central cannula 50 that permits the guide dilator 10 and connected retractor blades 12, 14, 16, 18 to be slid over one or more dilators used to initially enlarge an incision, as will be discussed in greater detail below. The blades 12, 14, 16, 18 form a round outer profile 52 around the guide dilator 10 interrupted by gap spacings 54 between adjacent retractor blades. With the blades 12, 14, 16, 18 connected to guide dilator 10 and the blade distal ends 34, 35, 37, 39 spaced from the guide dilator end 48, as shown in FIG. 1, the generally cylindrical leading end portion 42 of the guide dilator 10 and the round outer profile 52 of the blade distal ends 34, 35, 37, 39 sequentially dilate an incision and minimize stresses on the tissues surrounding the incision. In an alternative embodiment, the guide dilator 10 may lack a central cannula 50 and instead have a generally cylindrical configuration. In this approach, the leading end portion 42 may have a configuration to provide a controlled dilation of the incision.

Figure 3:
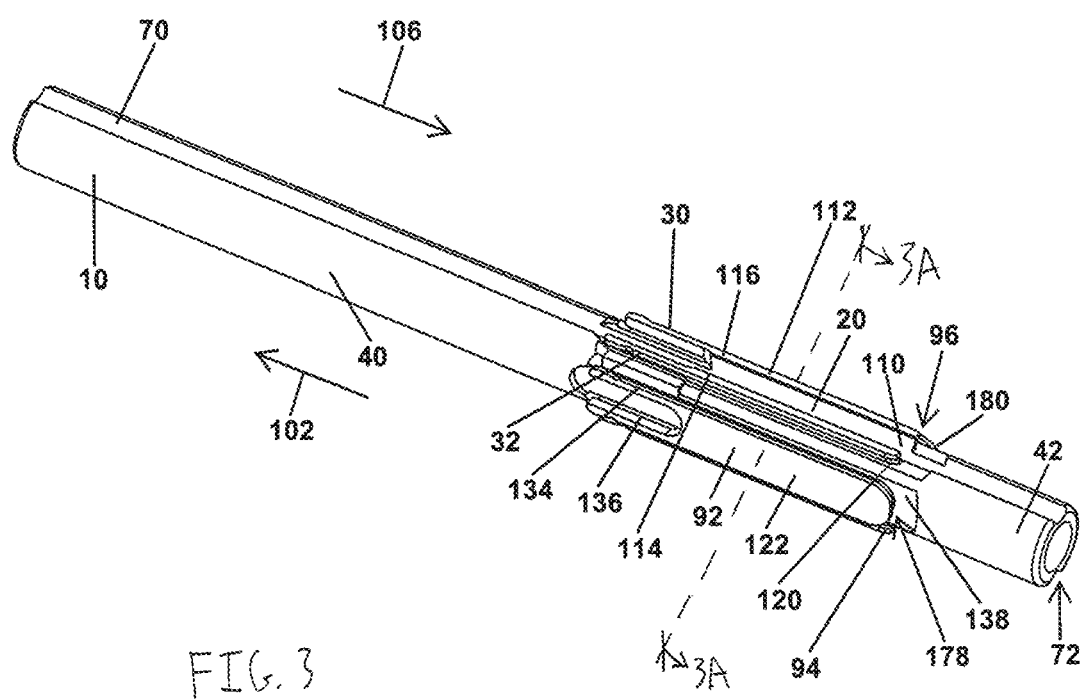
FIG. 3 is a perspective view of the guide dilator of FIG. 1 showing mounting rails of the guide dilator for slidably engaging in slots of the retractor blades of FIG. 1.

The guide dilator 10 and connected retractor blades 12, 14, 16, and 18 provide additional functionality once the guide dilator 10 reaches the surgical site. For example, the retractor blades 12, 16 are cannulated blades having cylindrical portions 64, 66 extending radially inward into grooves 70, 72 which extend along the length of the guide dilator 10, as shown in FIGS. 2, 3, and 5. The cylindrical portions 64, 66 have throughbores or cannulas 74, 76 that are unobstructed even when the blades 12, 16 are connected to the mounting rails 20, 94. A fixation pin, nerve monitoring probe, or other tool may be inserted along the grooves 70, 72 and into either one of the cannulas 74, 76 once the guide dilator and retractor blades 12 have been advanced to the surgical site. The presence of the unobstructed cannulas 74, 76 also provides a visual window for a surgeon to observe the tissues and bones directly beneath the blades 12, 16 without having to remove the retractor blades 12, 16 from the guide dilator 10. In one approach, a surgeon can visually check whether one of the cannulas 74, 76 is above a vertebra by looking through the cannula 74, 76 before driving a fixation pin through the cannula 74, 76 and into the vertebra to secure the associated blade 12, 16 to the vertebra.

Figure 3A:
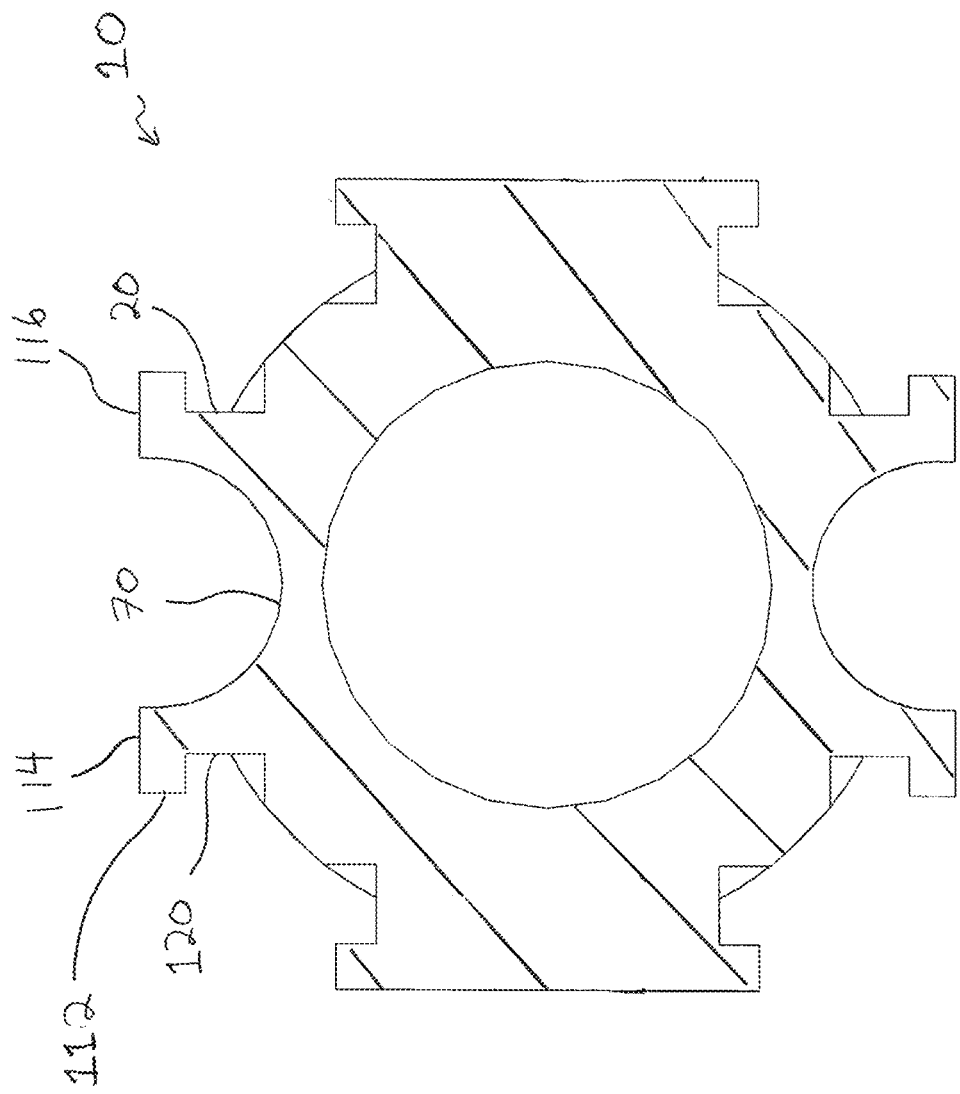
FIG. 3A is a cross sectional view of the guide dilator taken across line 3A-3A in FIG. 3 showing flanges of the mounting rails which engage cooperating slots on the retractor blades.

The mounting rails 20, 92, 94, 96 have features for rapidly engaging and disengaging the retractor blades 12, as shown in FIGS. 3 and 3A. For example, the mounting rail 20 has a lower base 110 and an upper flange 112, the flange 112 having two elongate sections 114, 116 separated by the elongate groove 70 therebetween. The elongate sections 114, 116 have integral resilient arms 30, 32 that frictionally engage inner slot surfaces 193, 195 (see FIG. 5) of the retractor blade 12 to resist removal of the blade 12 from the guide dilator 10. The guide dilator 10 also has mounting rails 92, 96 that are substantially similar to the mounting rails 20, 92 with the exception that the mounting rails 92, 96 are not intersected or divided by the grooves 70, 72. Instead, the mounting rail 92 has a lower base 120 and an upper flange 122 with resilient arms 134, 136 substantially similar to the arms 30, 32. Surrounding the lower base 120 of the mounting rail 92 is a recessed surface 138 that provides additional clearance for the retractor blade 14 to slide onto the mounting rail 92.

Figure 4:
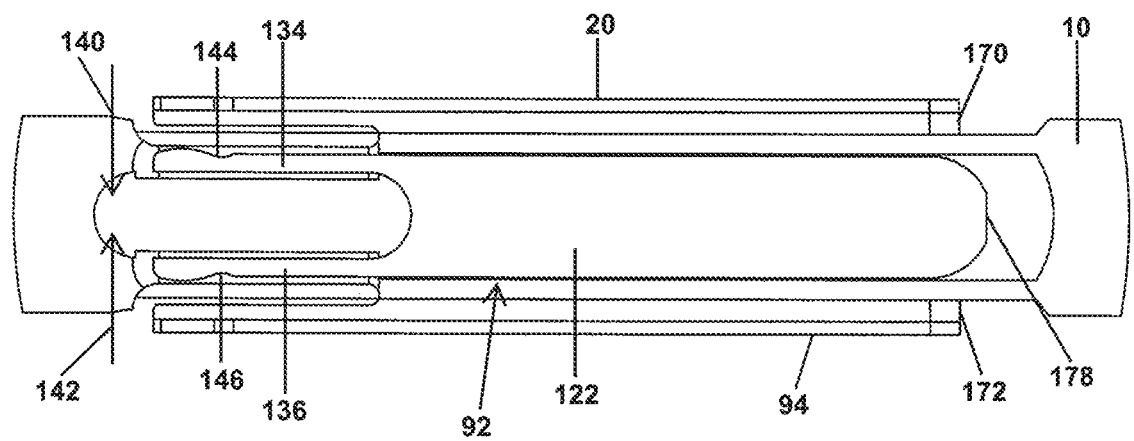
FIG. 4 is an enlarged, side elevational view of the mounting rails of the guide dilator of FIG. 1 showing resilient members of the mounting rails.
Figure 6:
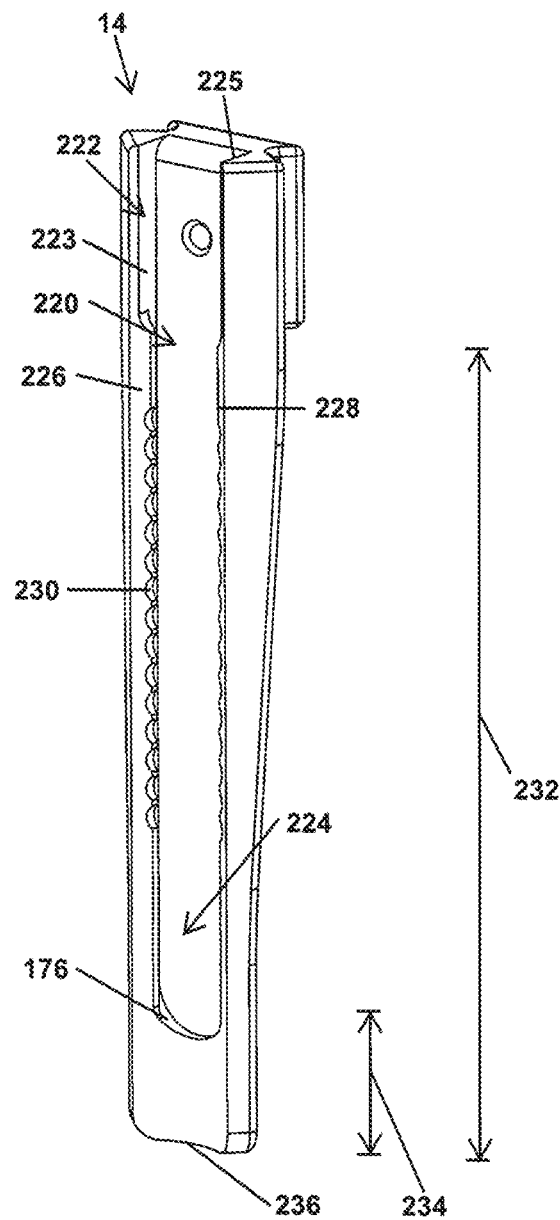
FIG. 6 is a perspective view of another one of the retractor blades of FIG. 1 showing a slot of the blade for slidably receiving a mounting rail of the guide dilator, the retractor blade of FIG. 6 lacking a cannula similar to the retractor blade of FIG. 5.

With reference to FIGS. 4 and 6, the resilient arms 134, 136 engage the slot 220 of the blade 14. The resilient arms 134, 136 have tapered surfaces 144, 146 that frictionally engage slot surfaces 223, 225 of the blade 14 and resist removal of the blade 14 from the mounting rail 92. When the blade 14 is connected to the mounting rail 92, the resilient arms 134, 136 are resiliently deflected toward each other in directions 140, 142 such that the resilient arms 134, 136 bias the tapered surfaces 144, 146 into frictional engagement with the slot surfaces 223, 225.

The guide dilator 10 and the retractor blades 12, 14, 16, 18 preferably have cooperating stop portions which limit sliding of the retractor blades beyond a position where the retractor blades 12, 14, 16, 18 are fully engaged with the mounting rails 20, 92, 94, 96. For example, with reference to FIG. 4, the mounting rails 20, 94 have lower end walls 170, 172 which abut stop surfaces on the blades 12, 16, such as the stop surface 174 of the blade 12 (see FIG. 5). The lower end walls 170, 172 have curvatures that are complimentary to the stop surfaces of the blades 12, 16 which permits the surfaces to firmly engage the end walls 170, 172. The mounting rails 92, 96 have similar lower end walls 178, 180 for engaging stop surfaces on the retractor blades 80, 82, such as a stop surface 176 of the blade 14 (see FIG. 6).

Figure 5A:
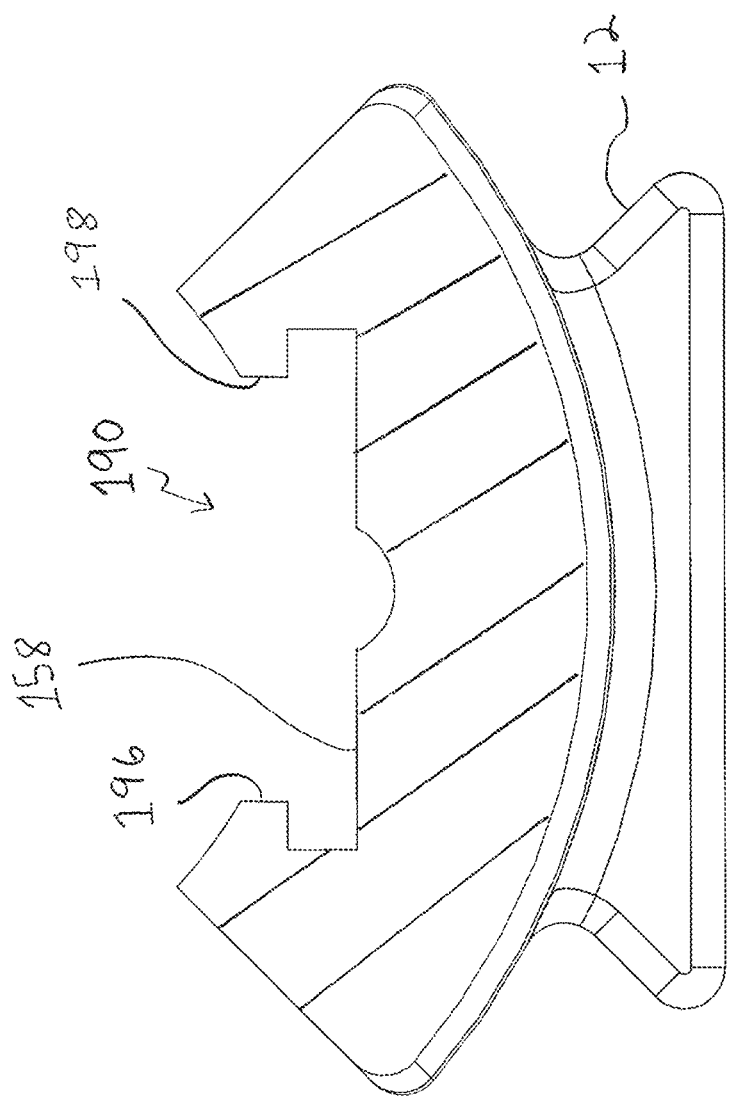
FIG. 5A is a cross-sectional view taken across the line 5A-5A in FIG. 5A

As shown in FIGS. 5 and 5A, a cannulated blade, such as the blade 12, has a slot 190 for receiving the flange 112 of the mounting rail 20. The slot 190 comprises an open end 192 and a closed end 194, the mounting rail 20 being inserted into the open end 192 of the slot 190 and slid along the blade 12 until reaching the closed end 194 of the slot 190. The blade 12 has inwardly extending walls 196, 198 which slide beneath the flange 112 and interlock therewith to restrict movement of the blade 12 radially outward from the guide dilator 10. In one form, axially extending surfaces of the flange 112 and the walls 196, 198 extend from a midline 199 of the blade 12 toward the distal end 36 of the blade 12 a distance that is at least a quarter of a blade length 210 (see FIG. 5) when the blade 12 is connected to the guide dilator 10. The walls 196, 198 have serrations 200, 202 for engaging ratchet arms 203, 205 of a docking anchor 201 (see FIG. 31) which may be inserted into the open end 192 of the slot 190 and slid down toward the closed end 194 with the ratchet arms 203, 205 resiliently biased into engagement with the serrations 200, 202 to releasably fix the depth of the docking anchor 201 within the blade 12.

Further, even if the retractor blades 12, 14, 16, 18 have varying straightness along their lengths, sliding the blades 12, 14, 16, 18 fully onto the mounting rails 20, 92, 94, 96 (see FIG. 1) holds distal ends 34, 35, 37, 39 of the blades 12, 14, 16, 18 to the guide dilator 10. The interlocking engagement between the flanges of the mounting rails, such as the flange 112 of the mounting rail 20, and the inwardly extending walls of the associated blade, such as walls 196, 198 of the blade 12, ensures that the walls 196, 198 are held below the flange 112 when the stop surface 174 is slid into engagement with the lower end wall 170 of the mounting rail 20. With the walls 196, 198 held firmly adjacent the lower base 110 of the mounting rail 20, the blade distal end 34 extends from the lower end wall 170 of the mounting rail 20 along the leading end portion 42 of the guide dilator 10. In this manner, the guide dilator 10 compensates for variation in the straightness of the retractor blades 12, 14, 16, 18 by ensuring the retractor blade distal ends 34, 35, 37, 39 are evenly spaced about the guide dilator 10 and spaced from each other.

The blade length 210 is chosen for a particular operation and typically is in the range of 80 mm-180 mm for lateral approach surgery. As shown in FIG. 5, the blade 12 also has a tip distance 216 extending between the stop surface 174 and the distal end 34. When the blade 12 is slid onto the mounting rail 20 and the lower end wall 170 of the mounting rail 20 abuts the stop surface 174 of the blade 12, the blade 12 generally extends the tip distance 216 along the leading end portion 42 of the guide dilator 10 beyond the stop surface 174 (see FIG. 3).

The blade 14 is substantially similar to the blade 12 with the exception of the cylindrical portion 64 and the cannula 74 thereof. Like the blade 12, the blade 80 has a slot 220 with an open end 222, a closed end 224, and inwardly extending walls 226, 228 with serrations 230. The blade 14 has a length 232 and a tip distance 234 extending between the stop surface 176 and a distal end 236 of the blade 14. The guide dilator 10 may be provided with sets of blades 12, 14, 16, 18 having different blade lengths 210 or 232, although the tip distance 216 or 234 remains similar for the different blade lengths. In this manner, the amount of leading end portion 42 covered by the blades 12, 14, 16, 18 is fixed for different sets of blades having different lengths.

Figure 7:
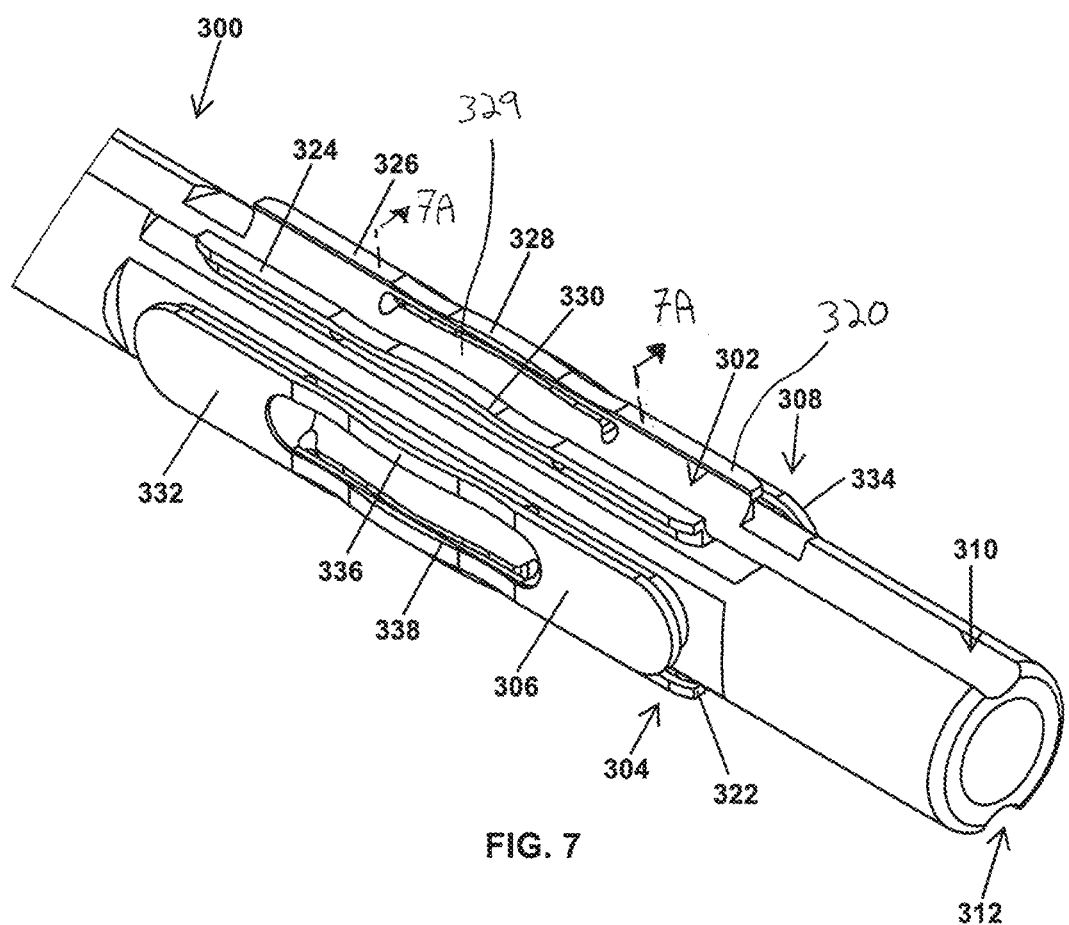
FIG. 7 is an enlarged, perspective view of a leading end of a guide dilator in accordance with another form of the present invention showing mounting rails of the guide dilator.

A guide dilator 300 in accordance with another form of the present invention is illustrated in FIG. 7. The guide dilator 300 is substantially similar to the guide dilator 10 previously discussed, with the exception that the guide dilator 300 has mounting rails 302, 304, 306, 308 with different mechanisms for retaining the respective retractor blades than the guide dilator 10. More specifically, the mounting rails 302, 304, which are intersected by grooves 310, 312, have flanges 320, 322 with elongate sections 324, 326 and resilient members 328, 330 disposed in the middle of the elongate sections 324, 326. The resilient members 328, 330 are resiliently biased radially outward into engagement with associated retractor blades to provide a frictional engagement therebetween in a manner similar to the resilient arms 30, 32. Likewise, the mounting rails 306, 308 have flanges 332, 334 with resilient members 336, 338 for creating frictional engagement with associated retractor blades.

As shown in FIG. 7A, the resilient member 328 of the mounting rail 302 is spaced from a lower portion 329 of the rail 302 by a gap 331 when a retractor blade is not connected to the mounting rail 302. Sliding a retractor blade onto the rail 302, such as blade 12, deflects the resilient member 328 radially inward in direction 333 and decreases the size of the gap 331, as shown in FIG. 7B. With the retractor blade 12 connected to the rail 302, the resilient member 328 biases against a surface 335 thereof radially outward in direction 337 into frictional engagement with a surface 158 of the blade 12 (see FIG. 5). In one approach, the guide dilator 300 is made of stainless steel or aluminum and the member 328 may resiliently flex due to the elongate gap spacing 331 machined into the mounting rail 302. The retractor blade 12 may be made of, for example, aluminum or polyether ether ketone (PEEK).

Figure 8:
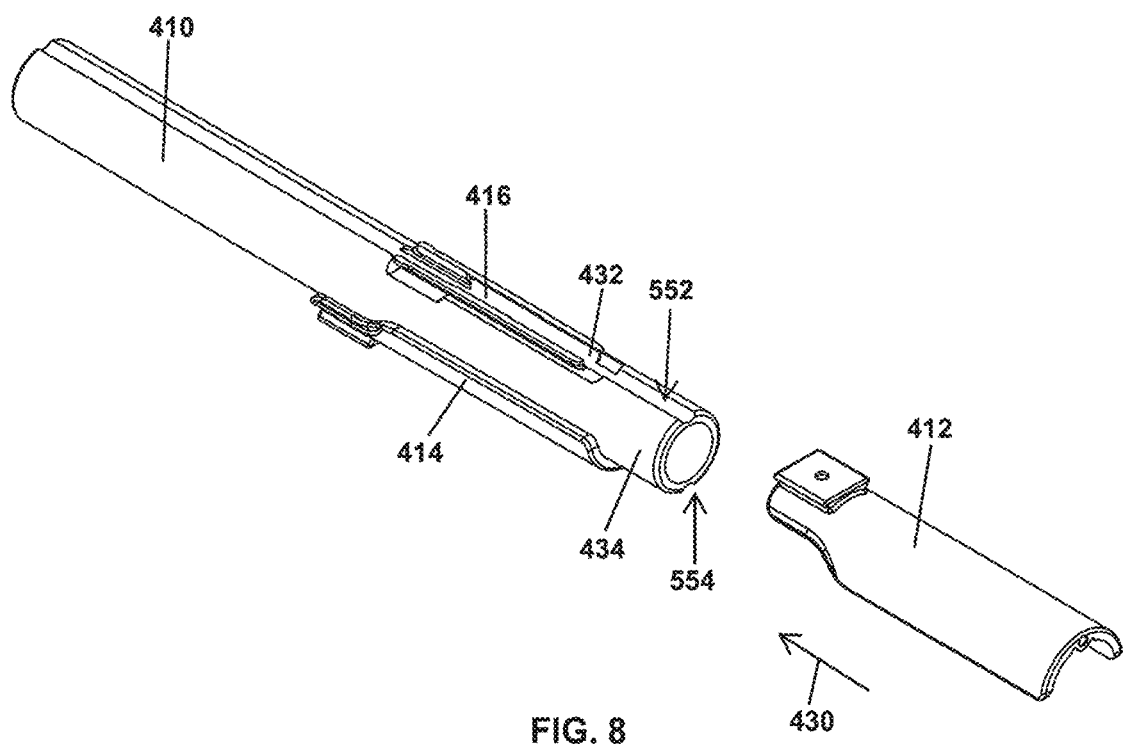
FIG. 8 is a perspective view of a guide dilator and retractor blades in accordance with another form of the present invention showing one of the retractor blades slid off of the guide dilator.
Figure 9:
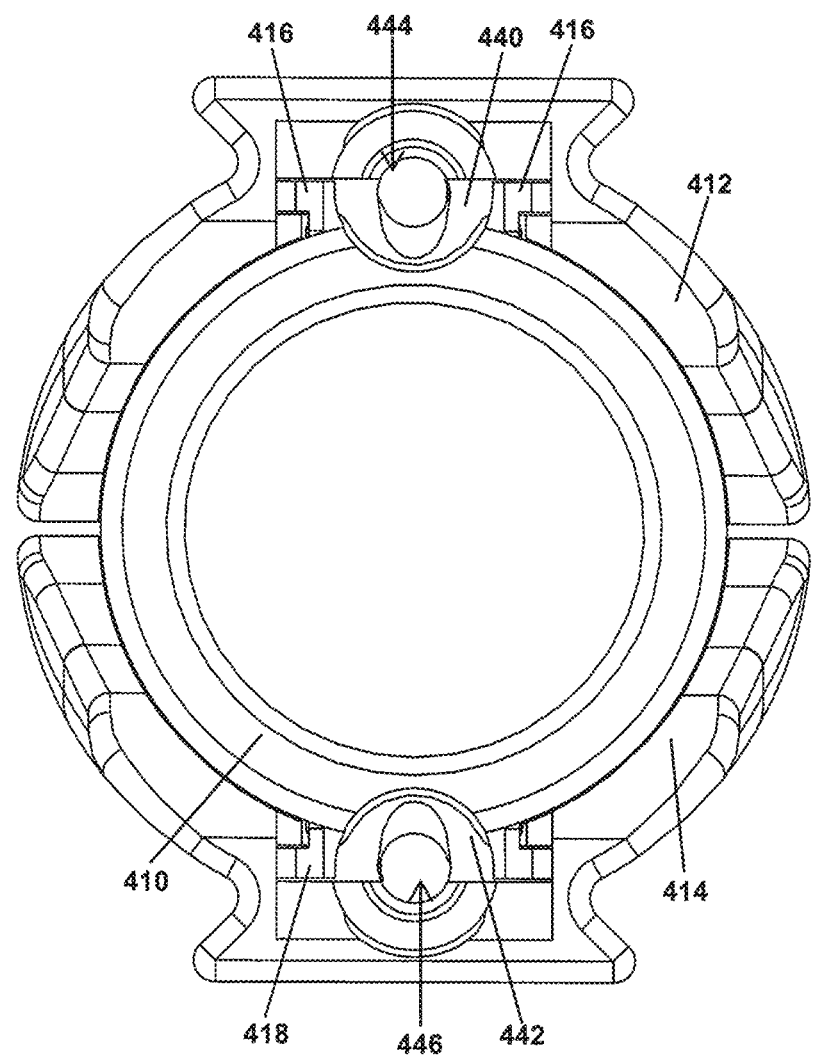
FIG. 9 is an enlarged, end view of the guide dilator of FIG. 8 with both retractor blades connected to the guide dilator showing an outer profile of the retractor blades.
Figure 10:
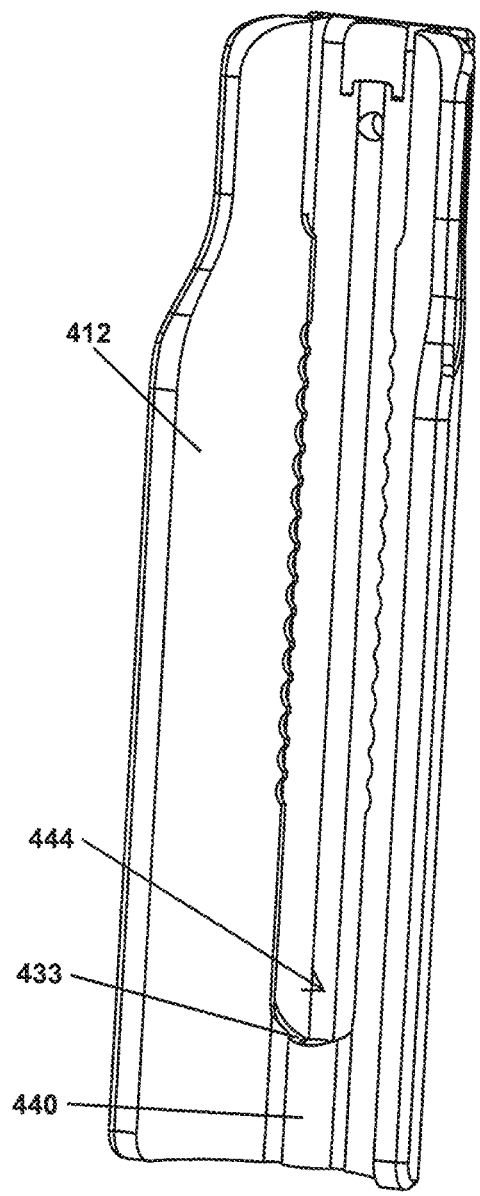
FIG. 10 is a perspective view of one of the retractor blades of FIG. 8 showing a slot of the blade for slidably receiving a mounting rail of the guide dilator.
Figure 11:
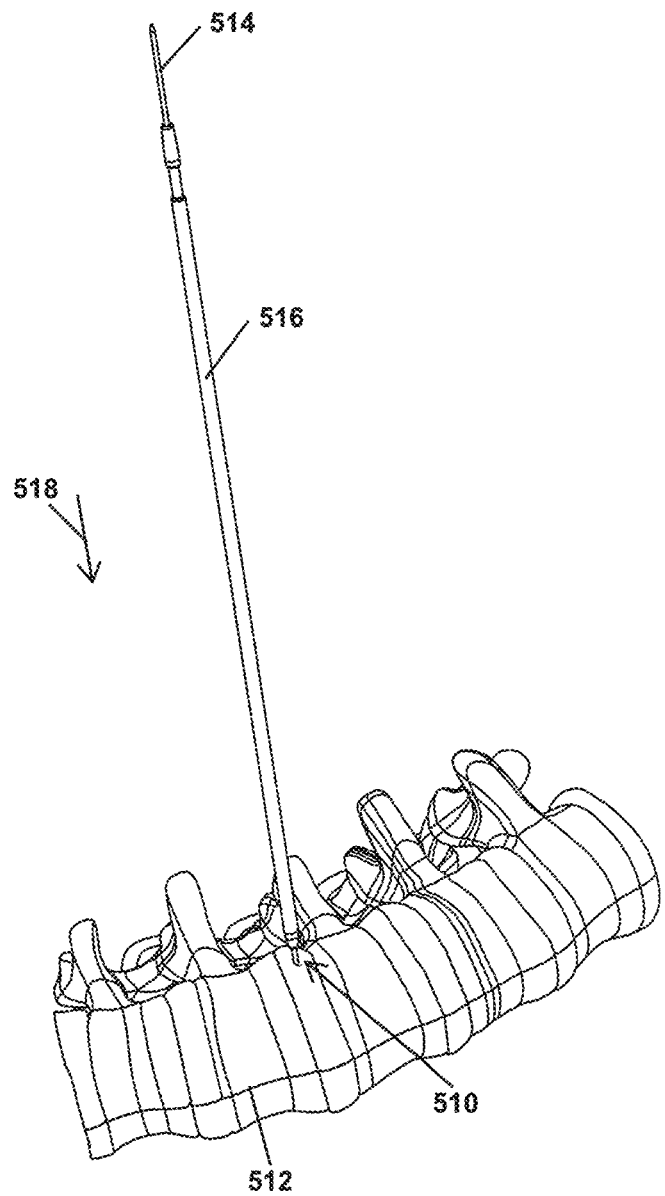
FIGS. 11-24 illustrate an exemplary method of enlarging an incision during a lateral approach surgery using the guide dilator and retractor blades of FIG. 8.

A guide dilator 410 and retractor blades 412, 414 in accordance with another form of the present invention are shown in FIGS. 8-10. The guide dilator 410 is similar to the guide dilator 10 and has mounting rails 416, 418 (see FIG. 9) for slidably engaging the blades 412, 414. Specifically, the blades 412, 414 slide onto the mounting rails 416, 418 in direction 430, as shown in FIG. 8. For example, blade 412 slides in direction 430 into engagement with mounting rail 416 and may slide in direction 430 until a stop surface 433 (see FIG. 10) engages a lower end wall 432 of the mounting rail 416. The blades 412, 414 may be easily and rapidly slid onto or off of the guide dilator 10 along a leading end portion 434 thereof.

Turning to FIG. 9, the blades 412, 414 form a generally circular profile when engaged with the guide dilator 410. One difference between the guide dilator 410 and the guide dilator 10 is that the guide dilator 410 has only two mounting rails 416, 418 to accommodate blades 412, 414 which each extend around the guide dilator 410 approximately 180 degrees. Another difference is that the blades 412, 414 are both cannulated with a cylindrical portion 440, 442 and cannulas 444, 446 sized to receive a fixation pin, nerve probe, or other instrument as will be discussed in greater detail below.

Figure 12:
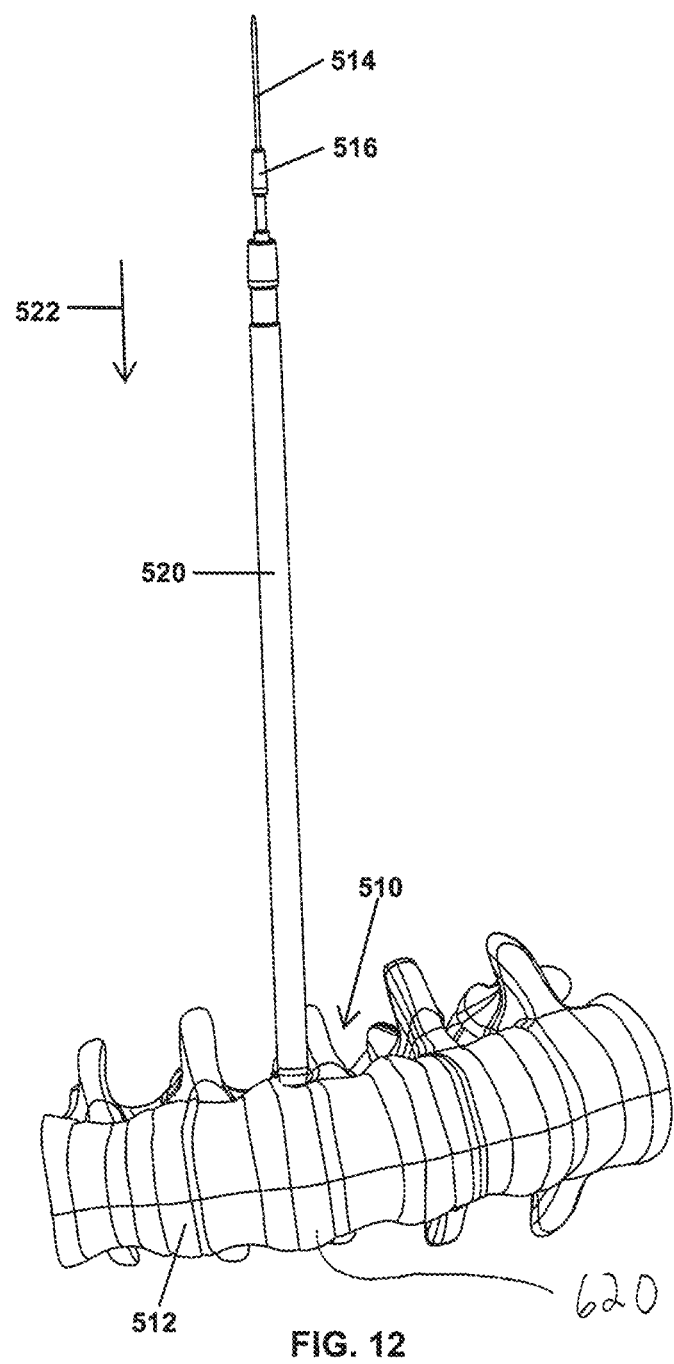
Figure 13:
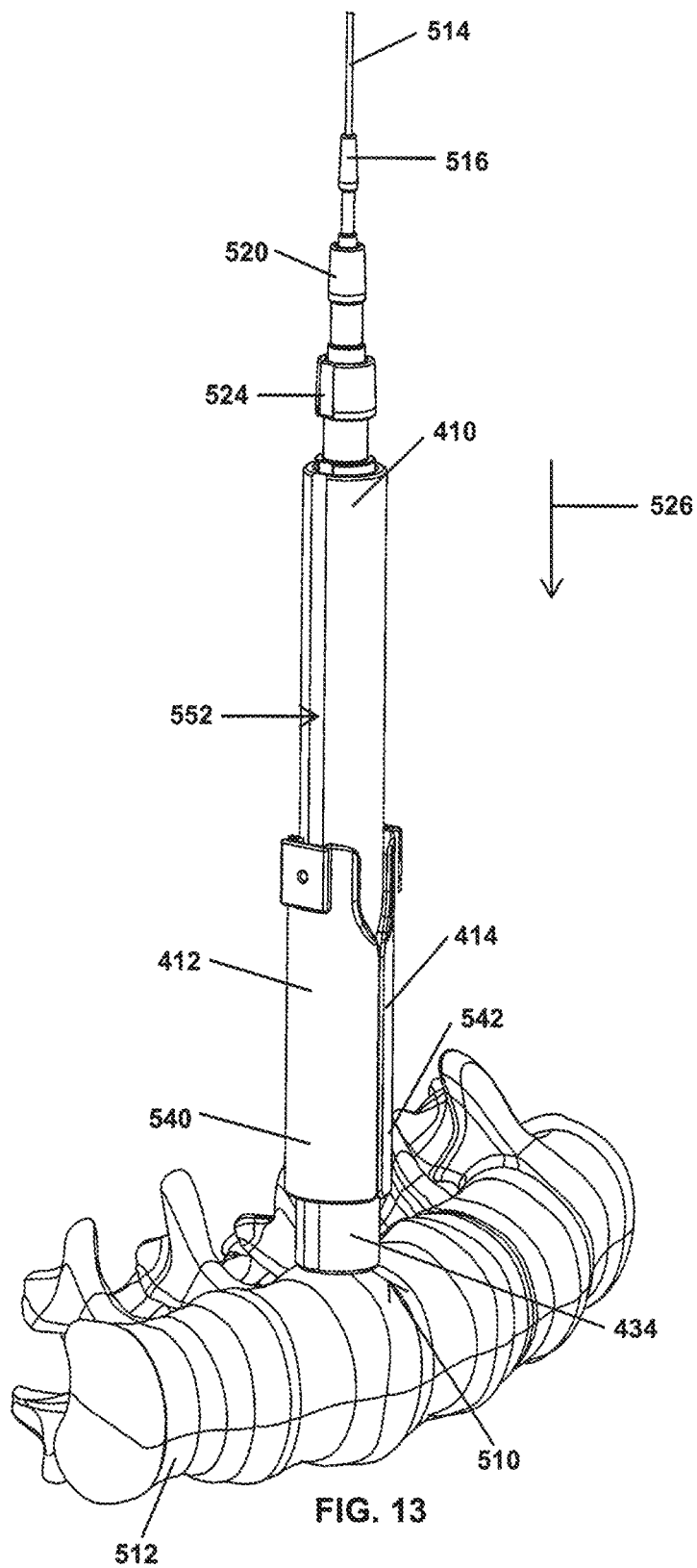
Figure 14:
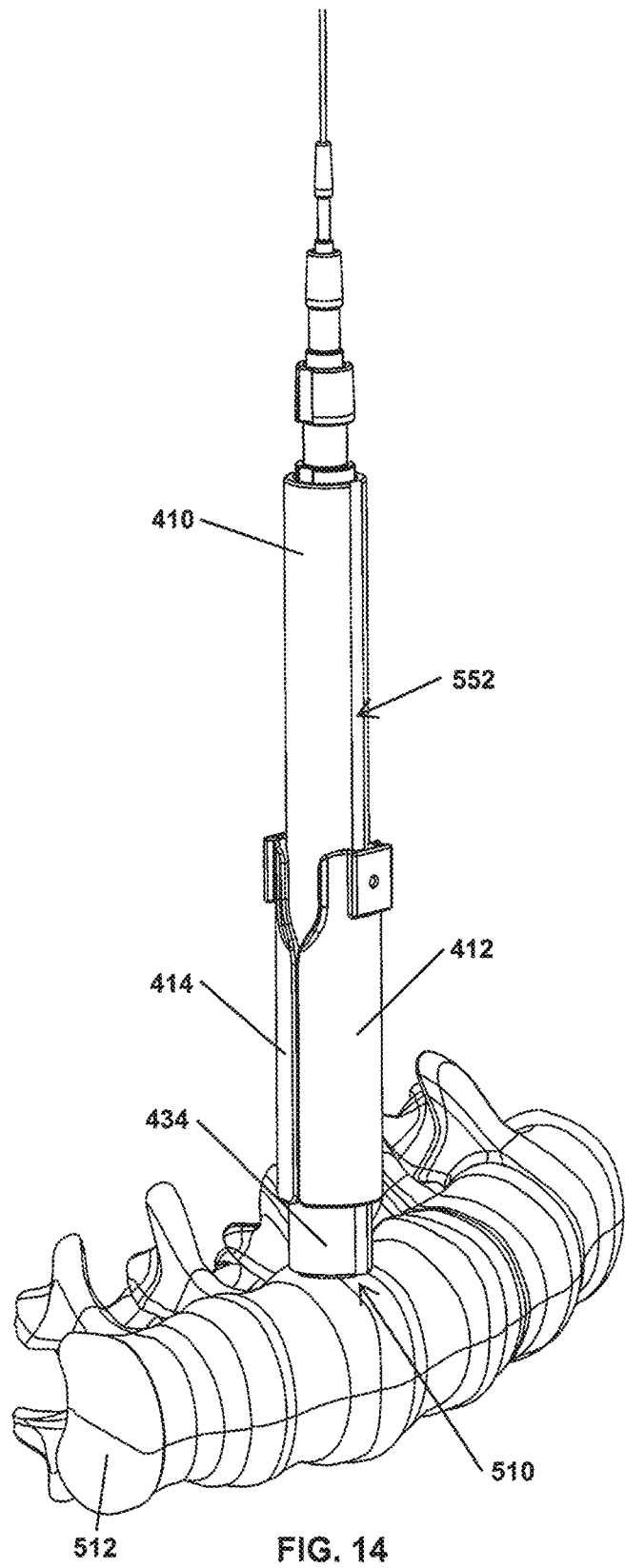
Figure 15:
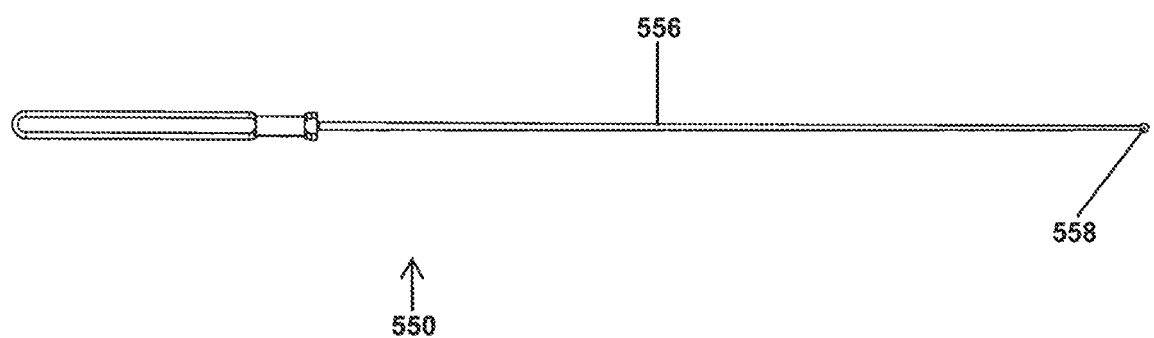
Figure 16:
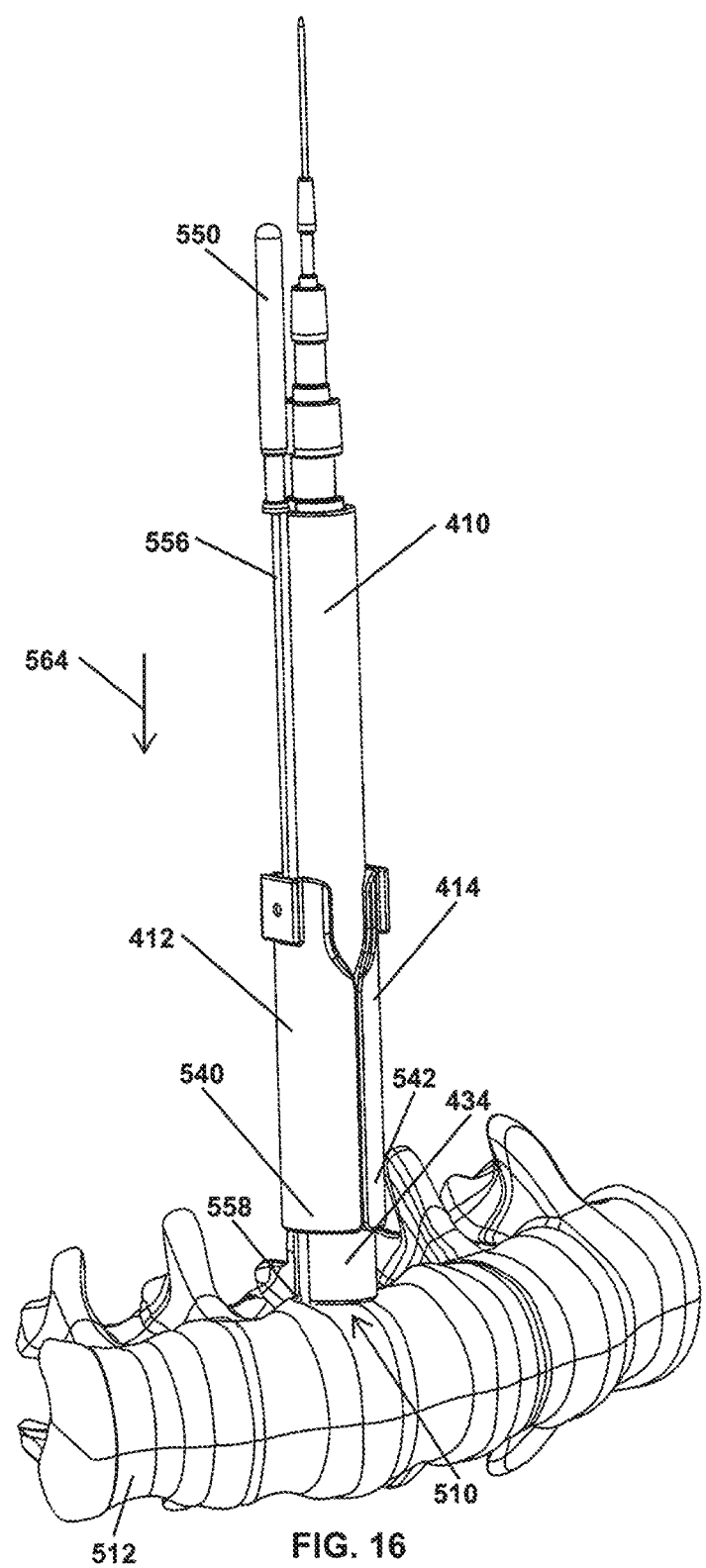

Referring next to FIGS. 11-24, a retraction procedure using the guide dilator 410 and the blades 412, 414 is illustrated. Initially, an incision is made adjacent a desired surgical site 510 of a spine 512. A dilator 516 is inserted in the incision into position at a surgical site 510, such as into contact with the intervertebral disc 620. A guide wire 514 is inserted into the cannula of the dilator 516 in direction 518 until the guide wire pierces into the intervertebral disc 620, securing the position of the dilator 516. As shown in FIG. 12, a second dilator 520 is slid downward along the first dilator 516 in direction 522 to further dilate the tissues surrounding the surgical site 510. A third dilator 524 may be slid over the second dilator 520 to further expand the tissues, as shown in FIG. 13. Once the dilators 516, 520, 524 have initially enlarged the incision, the assembled guide dilator 410 and the retractor blades 412, 414 may be slid along the dilator 524 in direction 526 into the incision. As is apparent, the leading end portion 434 of the guide dilator 410 enlarges the tissues surrounding the incision as the leading end portion 434 is advanced toward the surgical site 510. Further, distal ends 540, 542 of the retractor blades 412, 414 also dilate the tissues as the distal ends 540, 542 are advanced into the incision. In some approaches, it may be desirable to insert the guide dilator 410 and connected blades 412, 414 as shown in FIG. 14 to permit retraction of the blades 412, 414 in directions generally perpendicular to the length of the spine 512.

Figure 17:
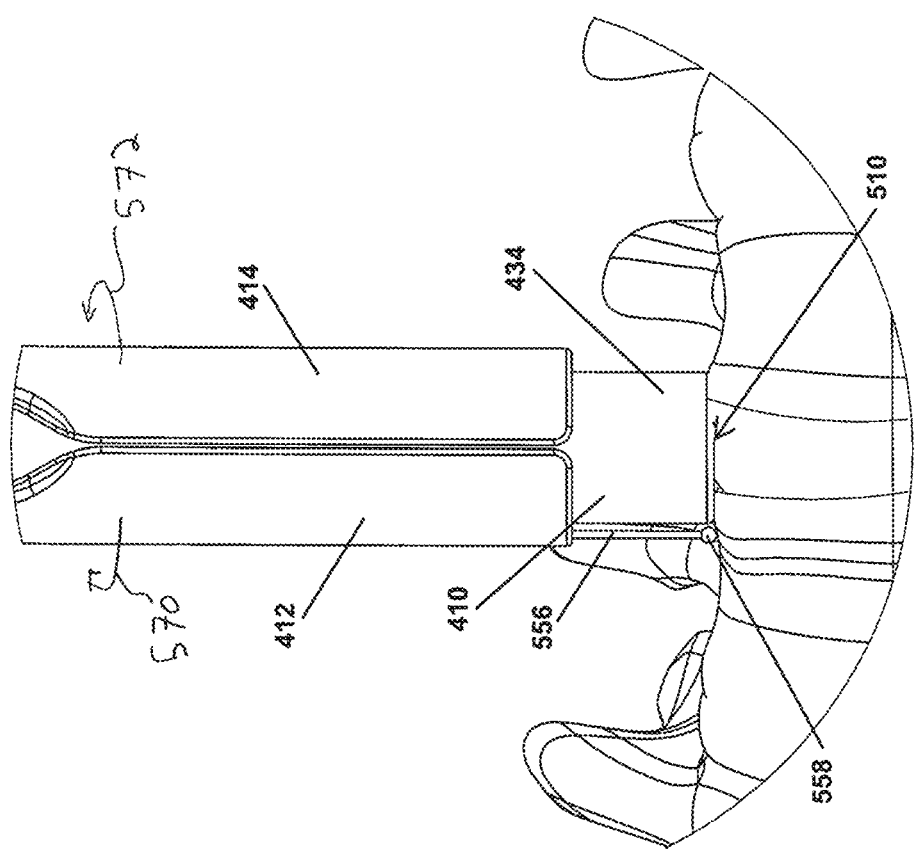

Once the leading end portion 434 of the guide dilator 410 reaches the surgical site 510, the surgeon may want to monitor for the presence of adjacent nerves before the retractor blades 412, 414 are slid downward along the leading end portion 434 into position adjacent the surgical site 510 would further dilate the tissues adjacent the surgical site 510. One approach to nerve monitoring involves advancing a nerve monitoring probe 550 (see FIG. 15) along one of the grooves 552, 554 extending along the length of the guide dilator 410 and into one of the cannulas 444, 446 (see FIG. 9) of the blades 412, 414. The nerve monitoring probe 550 has a shaft 556 ending at a bulbous tip 558 sized to fit into cannulas 444, 446 of the blades 412, 414. In the illustrated approach, the nerve monitoring probe 550 was inserted downward in direction 564 into the cannula 444 until the bulbous tip 558 extends downward beyond the tip 540 of the retractor blade 412. As shown in FIG. 17, the guide dilator 410 and the connected blades 412, 414 and nerve monitoring probe 550 may be rotated in directions 570, 572 to maneuver the tip 558 of the nerve monitoring probe 550 in a path around the surgical site 510. In this manner, the surgeon can monitor for the presence of nerves around the entirety of the leading end portion 434 before continuing the surgical procedure.

Figure 18:
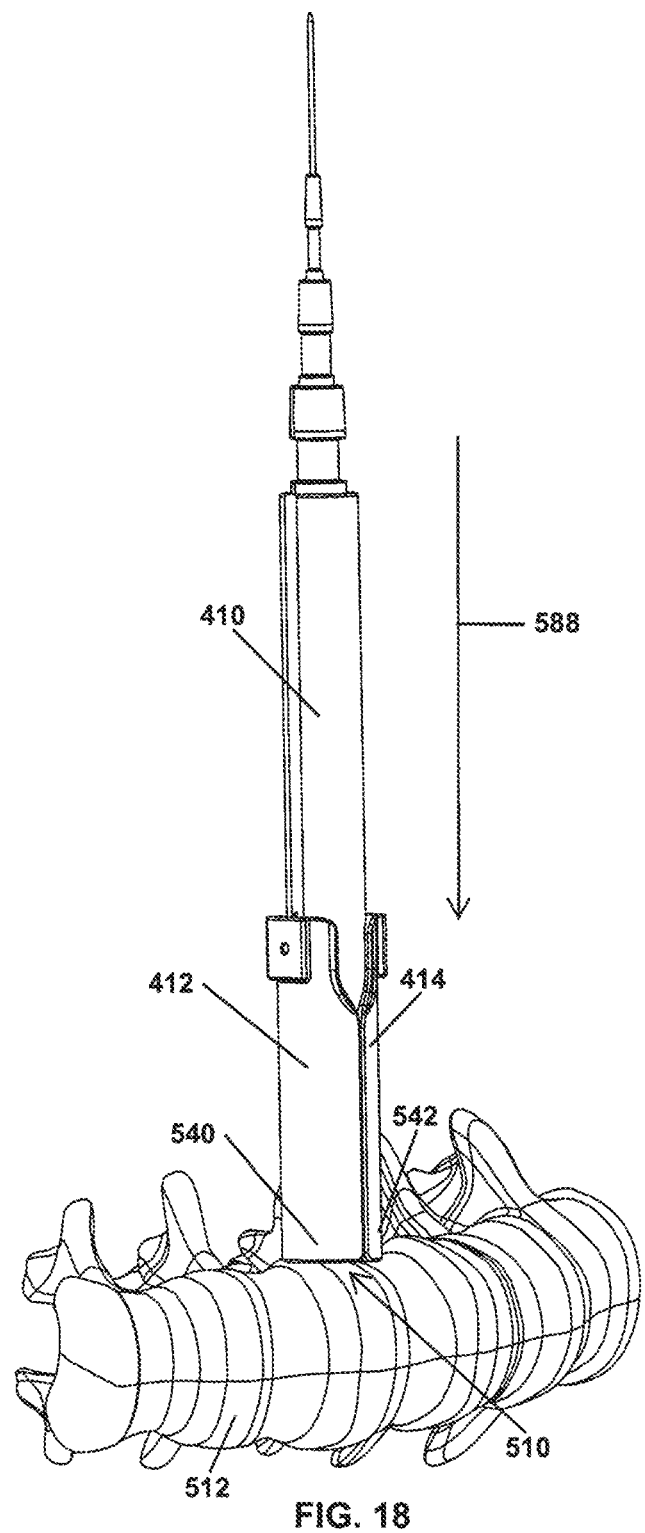
Figure 19:
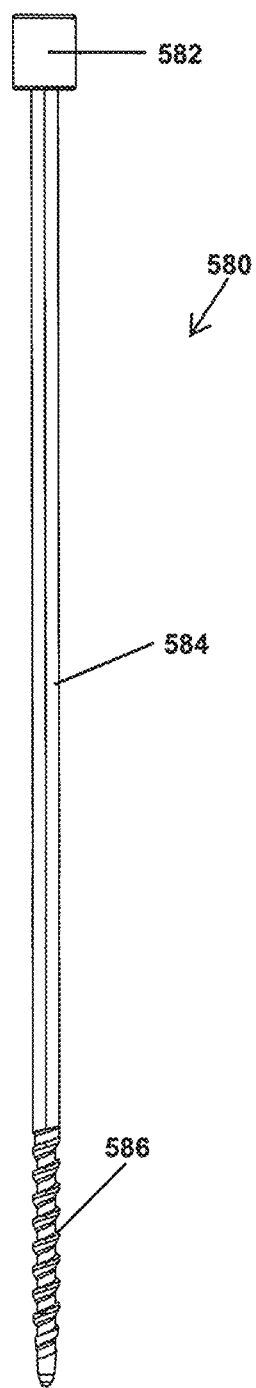
Figure 20:
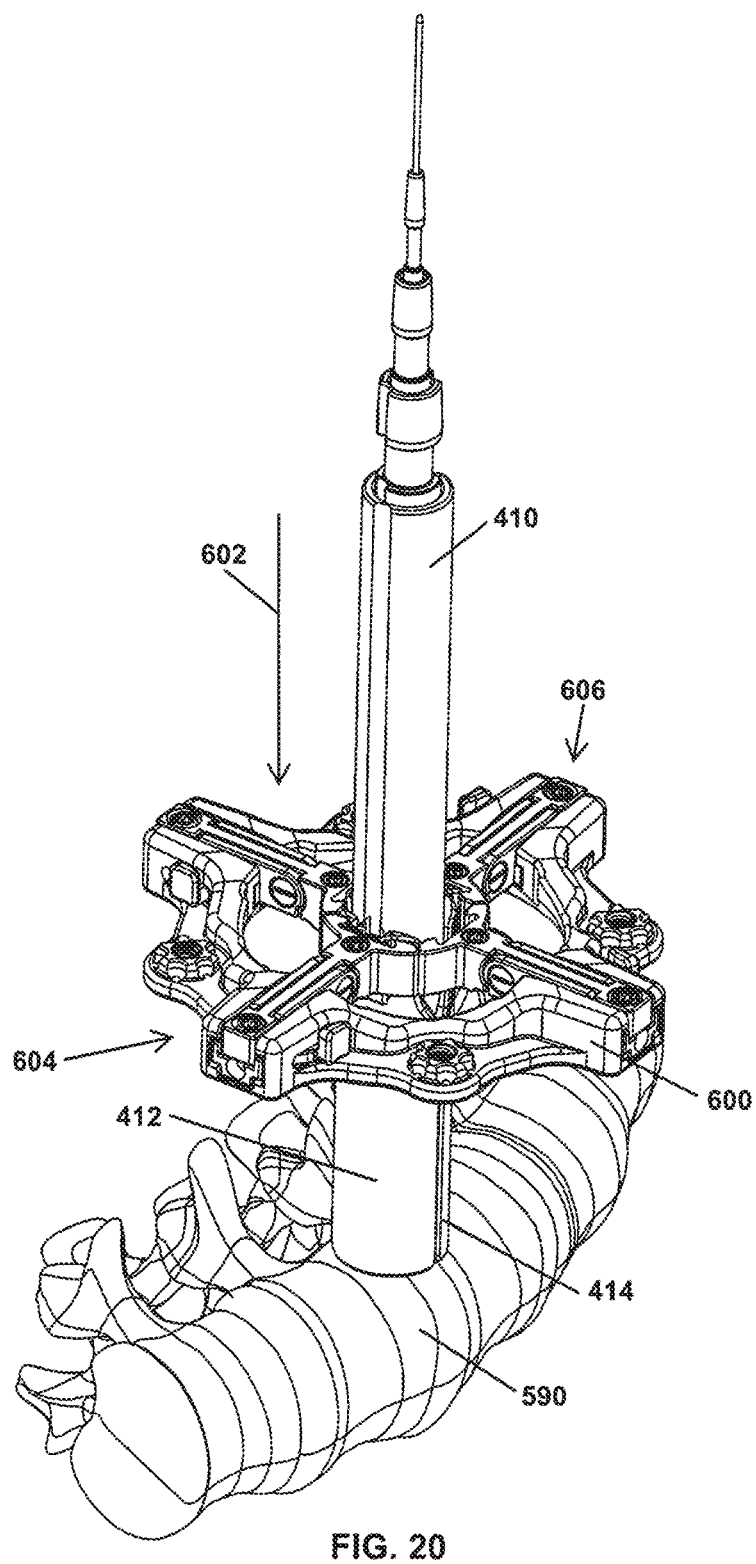

If the results of the nerve monitoring are satisfactory, the retractor blades 412, 414 are slid downwardly down the guide dilator 410 in direction 588 until distal ends 540, 542 are positioned adjacent the surgical site 510, as shown in FIG. 18. The retractor blades 412, 414 remain engaged with the mounting rails 416, 418 as the retractor blades 412, 414 slide along the leading end portion 434 of the guide dilator 410. At this point, the surgeon may want to secure the retractor blade 412 to a vertebra 590 (see FIG. 22) to stabilize the blade 412 relative to the patient during subsequent steps of the retraction procedure. In the illustrated approach, a fixation pin 580 having a head 582, a shank 584, and a tip 586 (see FIG. 19) is driven in direction 588 into the cannula 444 of the blade 412 after the nerve monitoring probe 550 has been removed from the cannula 444. With the blade 412 secured to the vertebra 590, as shown in FIG. 20, a retractor 600 is moved along the guide dilator 410 in direction 602 until operating mechanisms 604, 606 reach the blades 412, 414. As will be discussed in greater detail below, the operating mechanisms 604, 606 may be secured with the blades 412, 414 by engaging dovetail connections between the operating mechanisms 604, 606 and the blades 412, 414 and fixing the operating mechanisms 604, 606 to the blades 412, 414.

Figure 21:
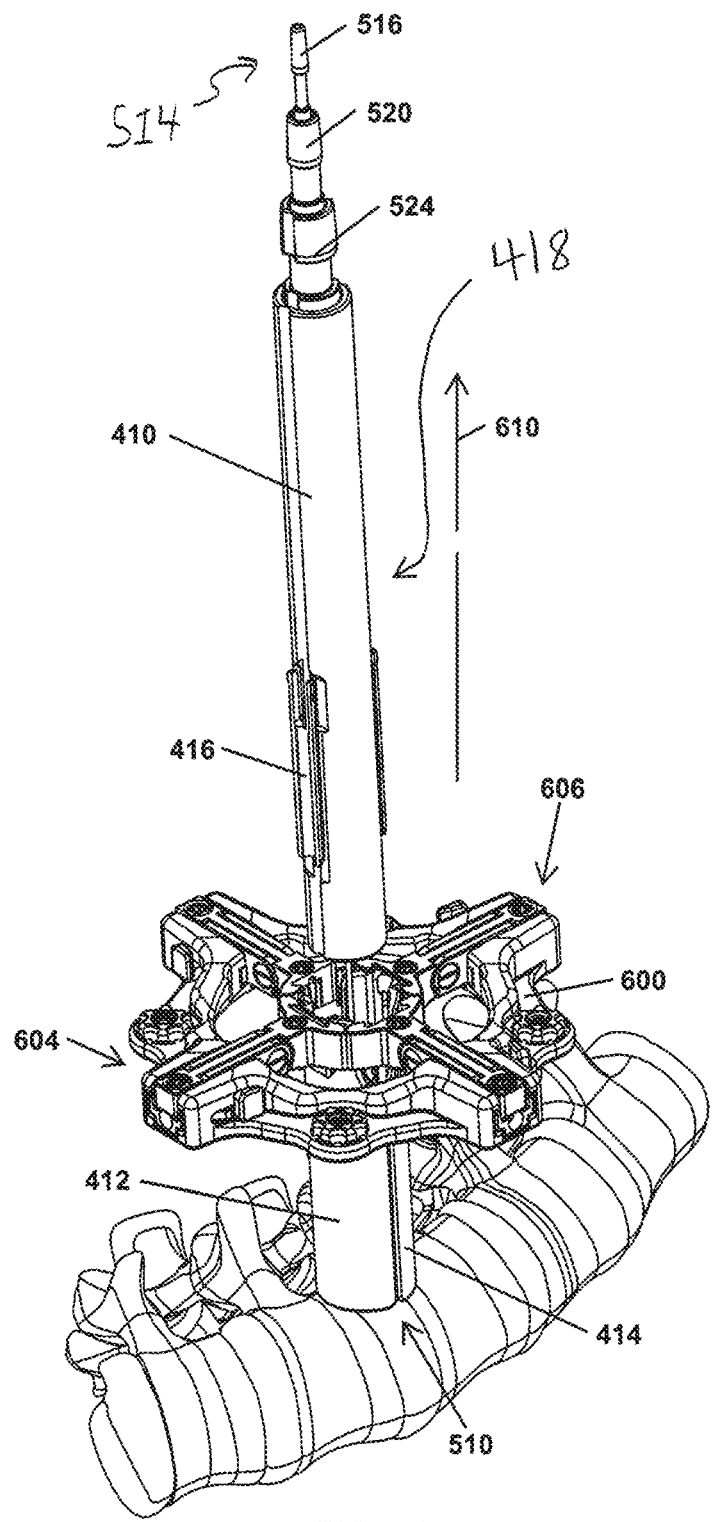

As shown in FIG. 21, the guide dilator 410, the guide wire 514, and the dilators 516, 520, 524 may be withdrawn from the incision in direction 610. With the operating mechanisms 604, 606 of the retractor 600 engaged with the blades 412, 414, the blades 412, 414 are held against movement while the guide dilator 410 is withdrawn in direction 610 outward from the incision. The relative movement between the guide dilator 410 and the retractor blades 412, 414 draws the mounting rails 416, 418 of the guide dilator 410 out of respective slots on the blades 412, 414 and disengages the connections therebetween. In this manner, withdrawing the guide dilator 410 simultaneously disengages the blades 412, 414 from the guide dilator 410 and removes the guide dilator 410 from a working channel 640 between the retractor blades 412, 414, as shown in FIG. 22.

Figure 22:
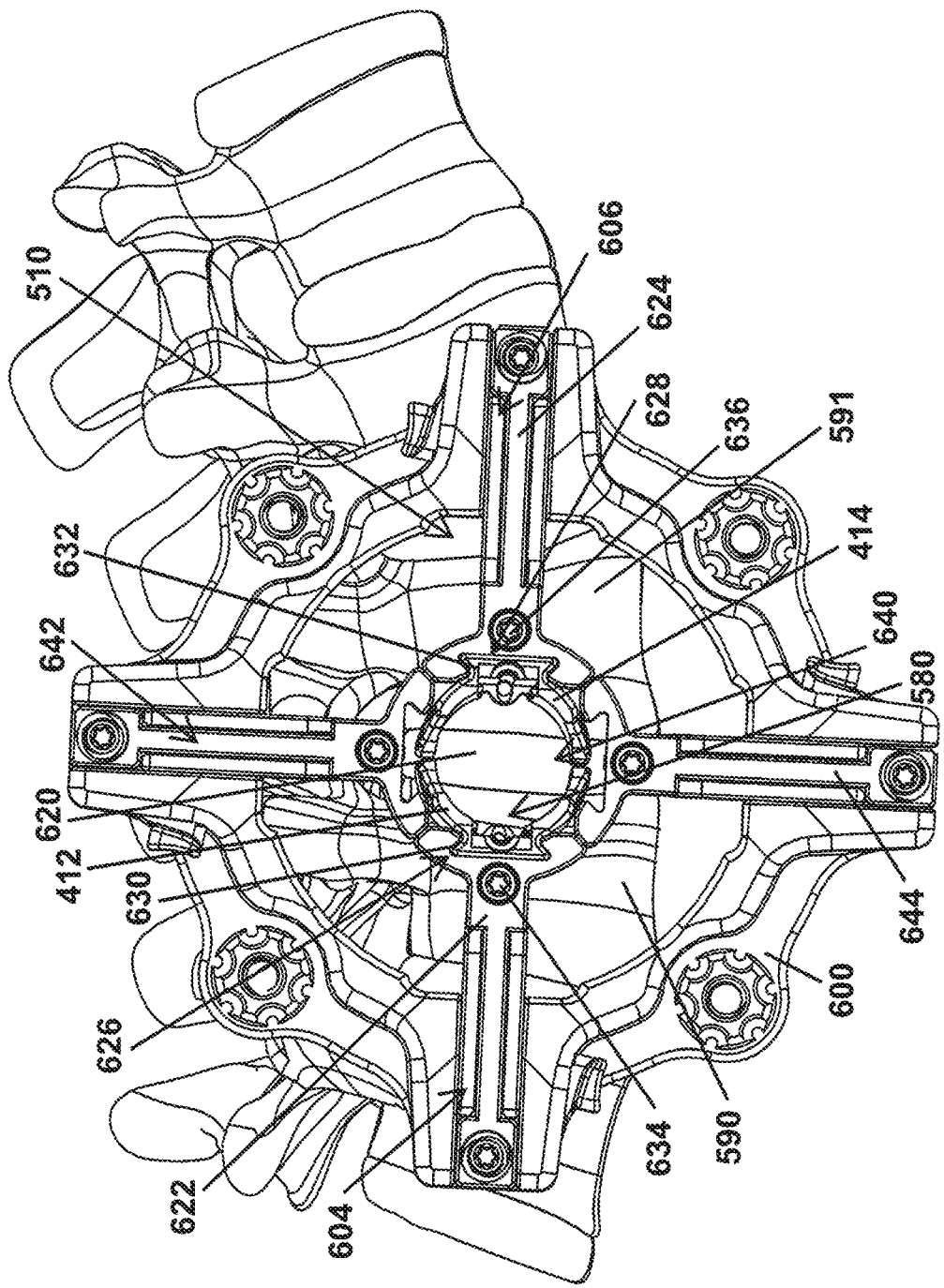
Figure 23:
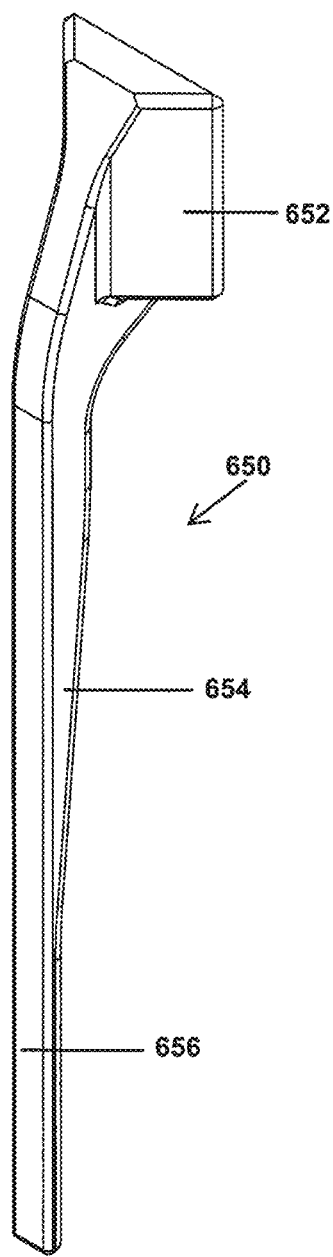
Figure 24:
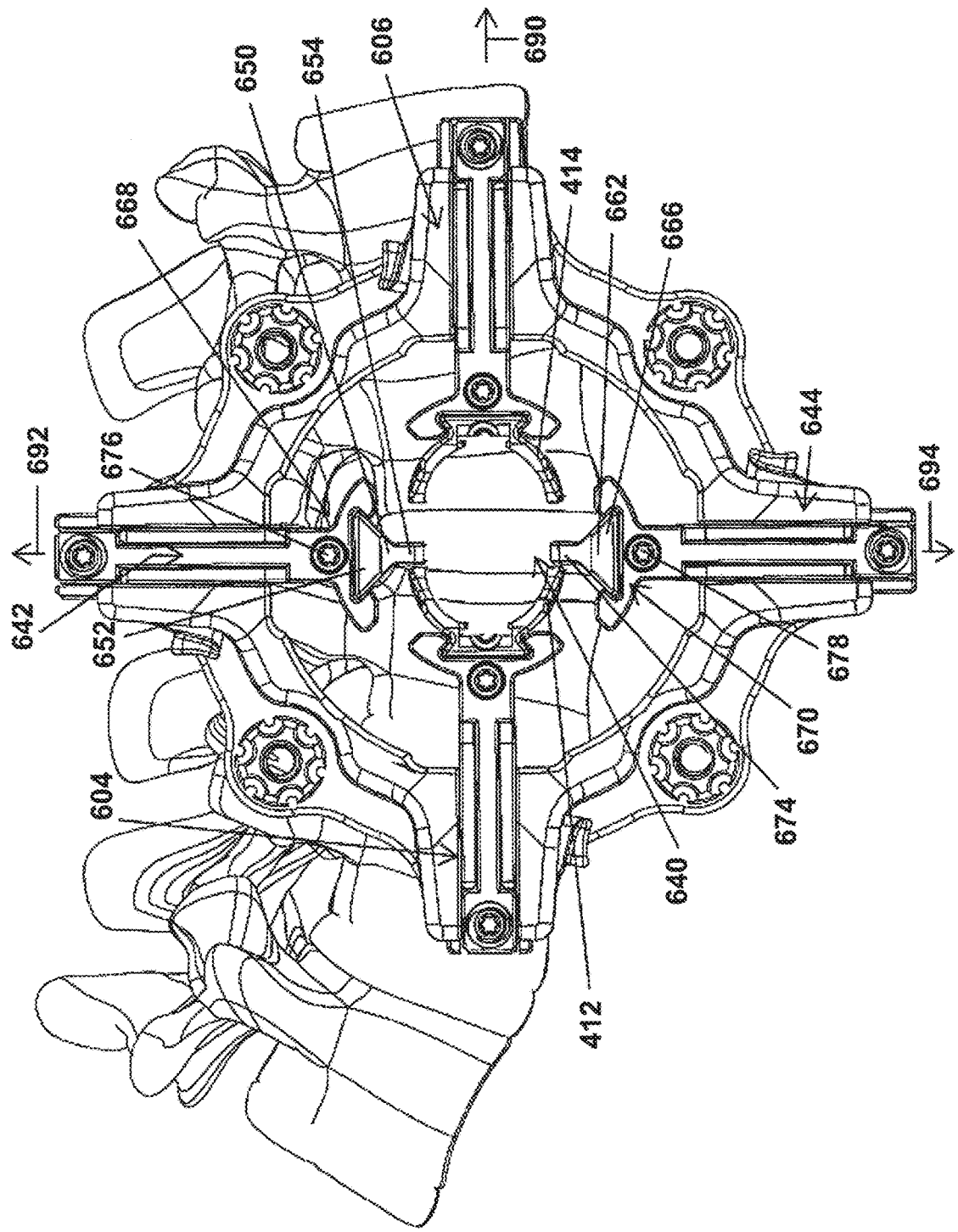

With reference to FIG. 22, the retractor 600 and the blades 412, 414 are shown positioned above the intervertebral disc 620 between vertebrae 590, 591. The operating mechanisms 604, 606 include sliders 622, 624 having dovetail recesses 626, 628 that slide over and into engagement with dovetail projections 630, 632 of the retractor blades 412, 414. The operating mechanisms 604, 606 have fixation screws 634, 636 that releasably fix the blades 412, 414 to the sliders 622, 624. As shown in FIG. 22, the retractor blades 412, 414 define an initial size of the working channel 640 to the intervertebral disc 620. To retract tissues in directions transverse to the operating mechanisms 604, 606, the retractor 600 has operating mechanisms 642, 644 that receive another pair of retractor blades such as a narrow retractor blade 650, as shown in FIG. 23. The narrow retractor blade 650 has a dovetail projection 652 and a body 654 extending from the dovetail projection 652 and ending at a tip 656. With reference to FIG. 24, narrow retractor blades 650, 662 have dovetail projections 652, 666 that are slid downward and engaged with the dovetail recesses 668, 670 with bodies 654, 674 advancing into gaps between the blades 412, 414. Fixation screws 676, 678 are tightened to engage the blades 660, 662 with the operating mechanisms 642, 644. The operating mechanisms 606, 642, and 644 are then retracted in directions 690, 692, 694 to enlarge the working channel 640 to a desired size to accommodate tools for operating on the intervertebral disc 620.

Figure 25:
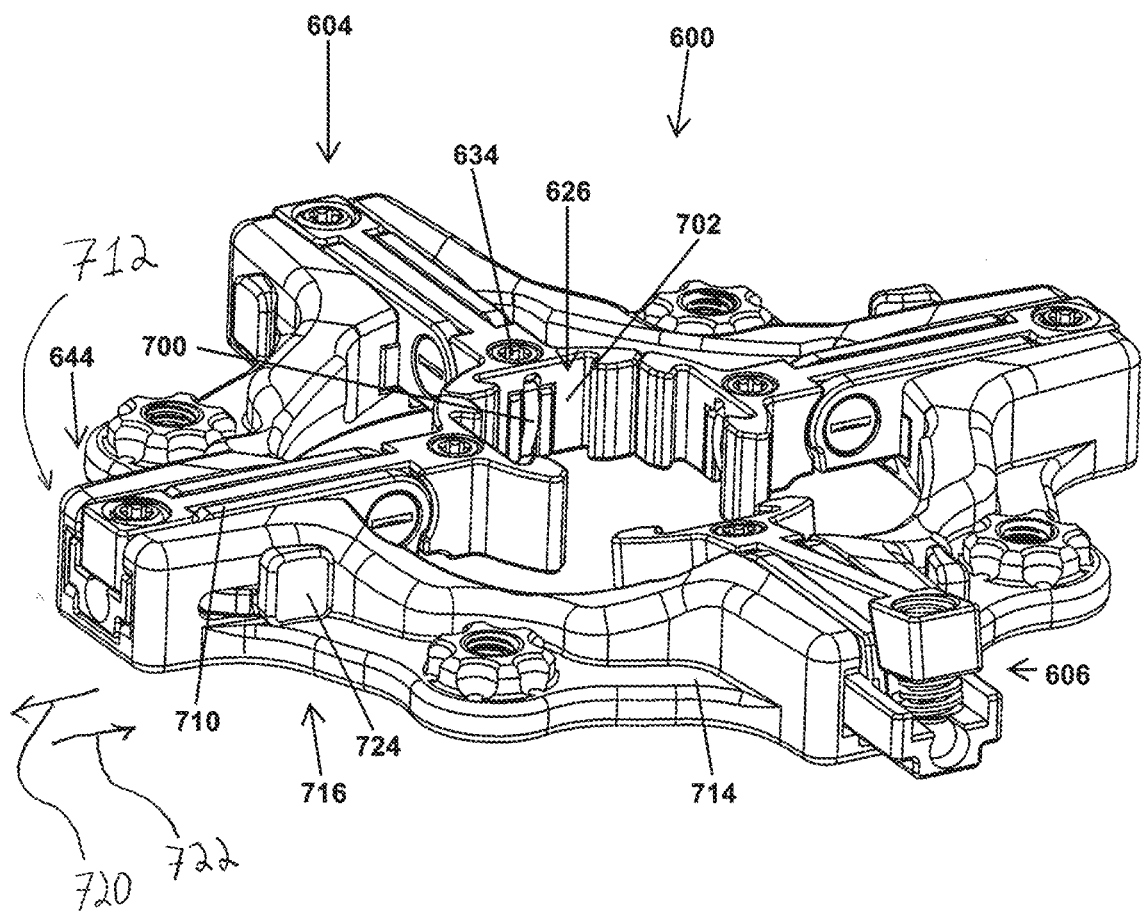
FIG. 25 is a perspective view of a retractor in accordance with one form of the present invention showing one of the sliders of the retractor in a retracted, pivoted position.
Figure 26:
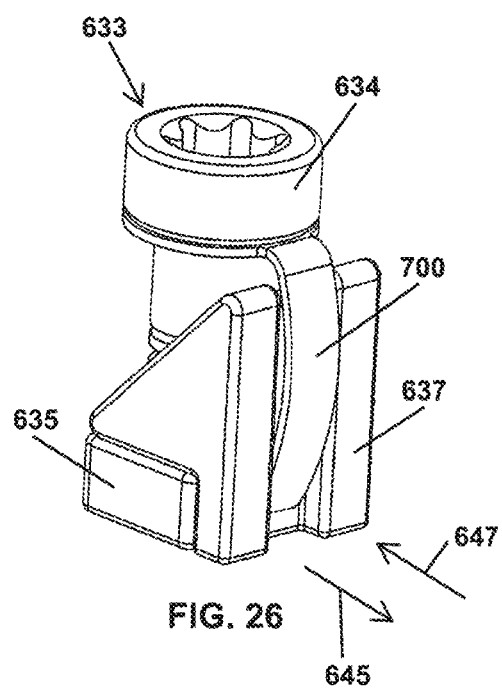
FIG. 26 is a perspective view of a wedge lock of a slider of the retractor of FIG. 25 showing the wedge lock removed from the slider.
Figure 27:
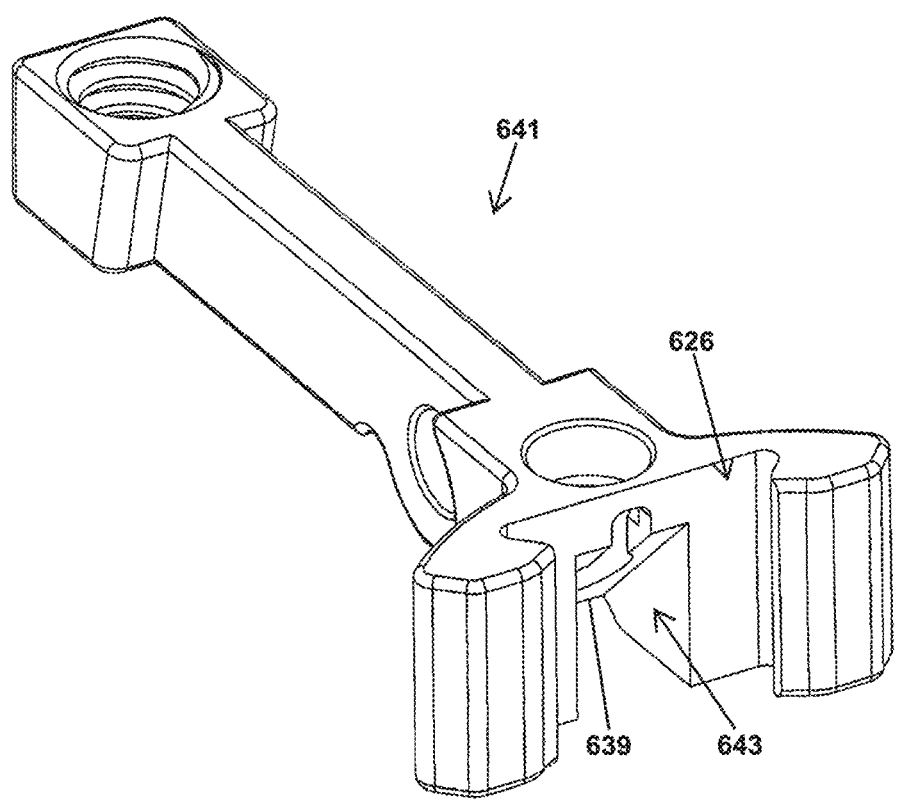
FIG. 27 is a perspective view of a slider inner member of the retractor of FIG. 25 showing the inner member removed from the retractor.

With reference to FIG. 25, the operating mechanism 604 has a resilient element 700 disposed in the dovetail recess 626 which aids in releasably securing the blade 630 to the operating mechanism 604. More specifically, the operating mechanism 604 includes a wedge lock 633 having a fixation screw 634 threadingly engaged with a nut 635, as shown in FIG. 26. The wedge lock 633 is disposed in a recess 643 of a slider inner member 641 of the operating mechanism 604, as shown in FIG. 27. Tightening the fixation screw 634 draws the nut 635 upward along the fixation screw 634 and engages wedge 637 with an inclined surface 639 of an inner member 641. Drawing the wedge 637 upward along the inclined surface 639 shifts the wedge outward in direction 645 which applies pressure against the dovetail projection 630 of the retractor blade 412 received in the dovetail recess 626 and fixes the blade 412 to the slider inner member 641. Loosening the fixation screw 634 shifts the nut 635 downward along the screw 634 and the resilient element 700 biases the wedge 637 downward and radially inward in direction 647 to return the wedge 637 to an initial, unlocked position shown in FIG. 26.

Figure 28:
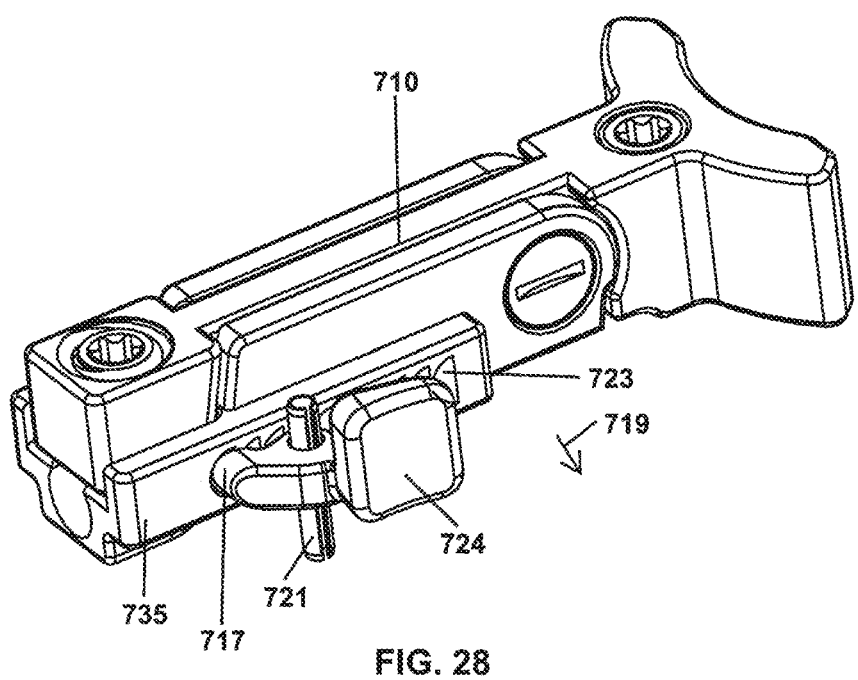
FIG. 28 is an enlarged, perspective view of a slider and portions of a ratchet mechanism of the retractor of FIG. 25 showing the slider and the ratchet mechanism portions removed from the retractor.

As shown in FIG. 25, the operating mechanism 644 includes a slider 710 disposed in a slot 712 of the retractor frame 714. The operating mechanism 644 further comprises a ratchet mechanism 716 that permits the slider 710 to retract in direction 720 but restricts return movement of the slider 710 until a button 724 of the ratchet mechanism 10 is pressed to disengage the ratchet mechanism 716 from the slider 710. With reference to FIG. 28, the slider 710 and portions of the ratchet mechanism 716 are shown removed from the frame 714 of the retractor 600. The ratchet mechanism 716 includes an integral tooth 717 of the button 724 and a spring (not shown) that biases the button 724 in direction 719 around shaft 721 and the tooth 717 into engagement with depressions 723 on a base 735 of the slider 710. Pressing the button 724 overcomes the biasing force of the spring and disengages the tooth 717 from the depressions 723 on the base 735.

Figure 29:
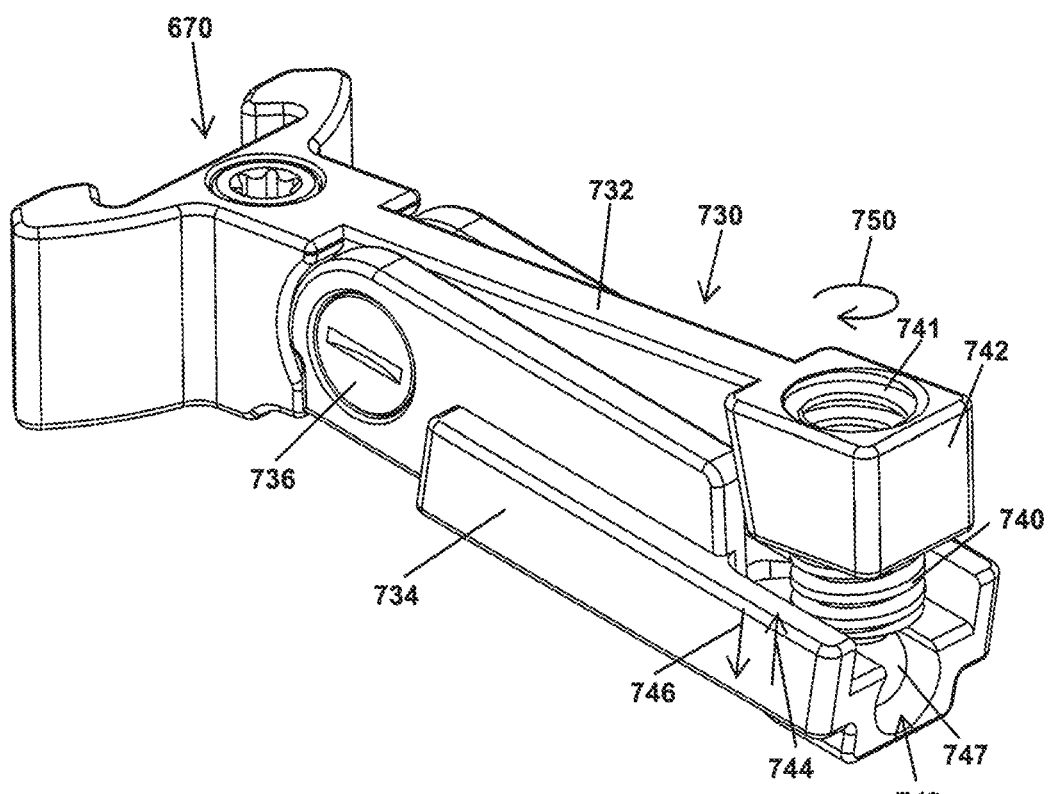
FIG. 29 is an enlarged, perspective view of a slider of the retractor of FIG. 25 showing an inner member of the slider having its rear end portion pivoted upward.

With reference to FIG. 29, the slider 730 is shown removed from the retractor frame 714. The slider 730 comprises an inner member 732 pivotally connected with a base 734 at a pivot pin 736. The slider 730 includes an elevation screw 740 engaged with threads 741 of the inner member 732. The elevation screw 740 has a ball 747 at one end thereof engaged with a socket 748 of the base 734. Rotating the elevation screw 740 in direction 750 elevates an end 742 of the inner member 732 in direction 744 and rotation of the elevation screw 740 in an opposite direction lowers the end 742 in direction 746. The connection between the ball 747 and the socket 748 permits the elevation screw 740 to rotate and elevate/lower the inner member 732 while pivoting relative to the base 734 as the inner member 732 elevates/lowers.

Figure 30:
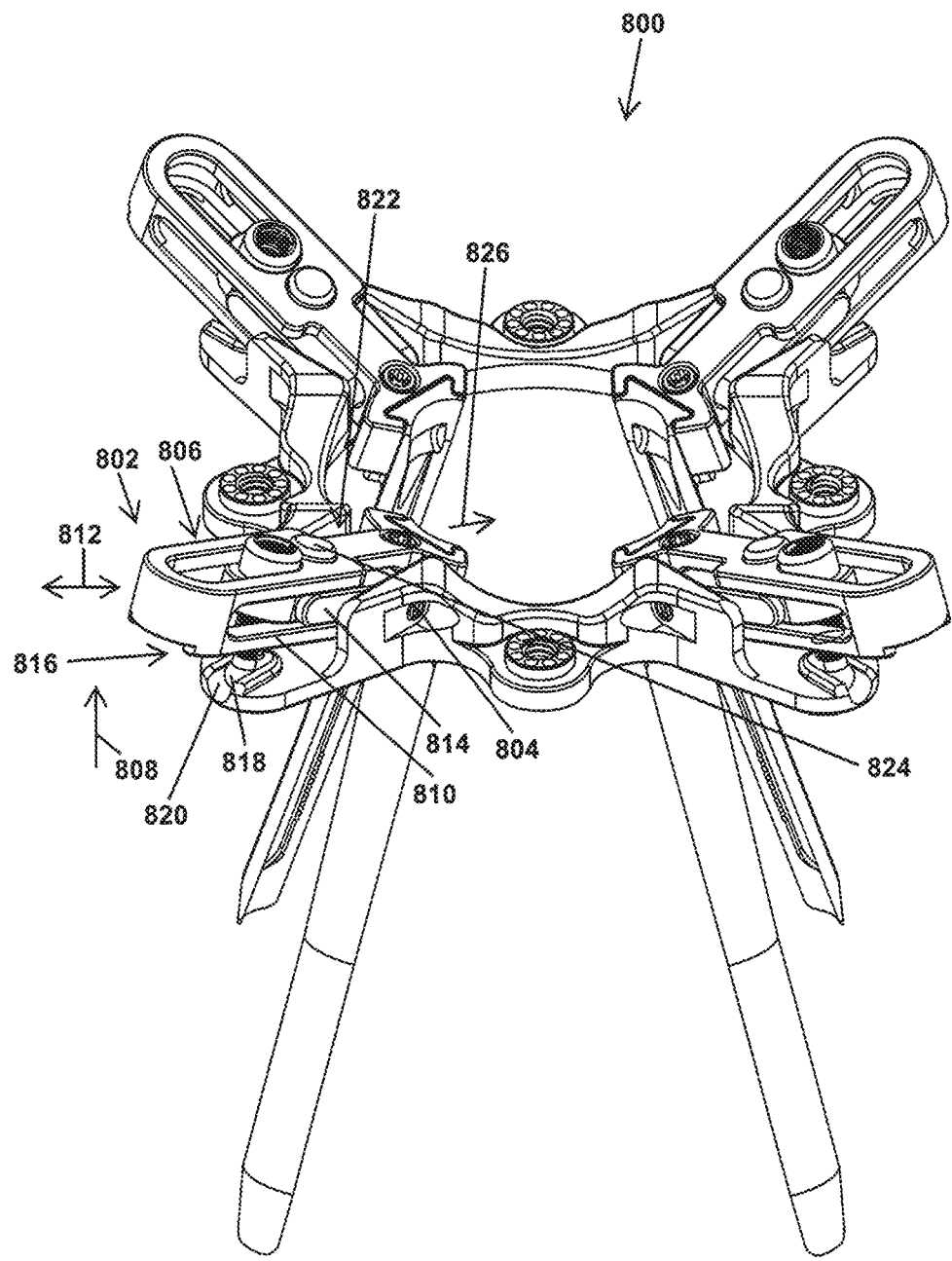
FIG. 30 is a perspective view of a retractor in accordance with another form of the present invention showing retractor blades connected to sliders which are retracted and pivoted.

With reference to FIG. 30, a retractor 800 in accordance with another form of the present invention is shown. The retractor 800 is substantially similar to the retractor 600, except for operating mechanisms 802 that have a fixed pivot pin 804 about which a slider 806 of the operating mechanism 802 pivots in direction 808. By contrast, the pivot pin 736 of the slider 750 (see FIG. 29) retracts with retraction of the slider 730. Another difference is that the slider 806 has a slider outer body 810 which slides along axis 812 relative to a slider inner body 814. Like the retractor 600, the retractor 800 has an elevation screw 816 with a ball 818 and socket 820 for accommodating pivoting of the slider 806. Further, the operating mechanism 802 includes a ratchet mechanism 822 that permits retraction of the slider 806 but restricts movement of the slider 806 in direction 826 in a manner similar to the operating mechanism 644. The ratchet mechanism 822 includes a button 824 that is pressed to disengage the ratchet mechanism 822 and permit the slider 806 to move in direction 826.

Figure 31:
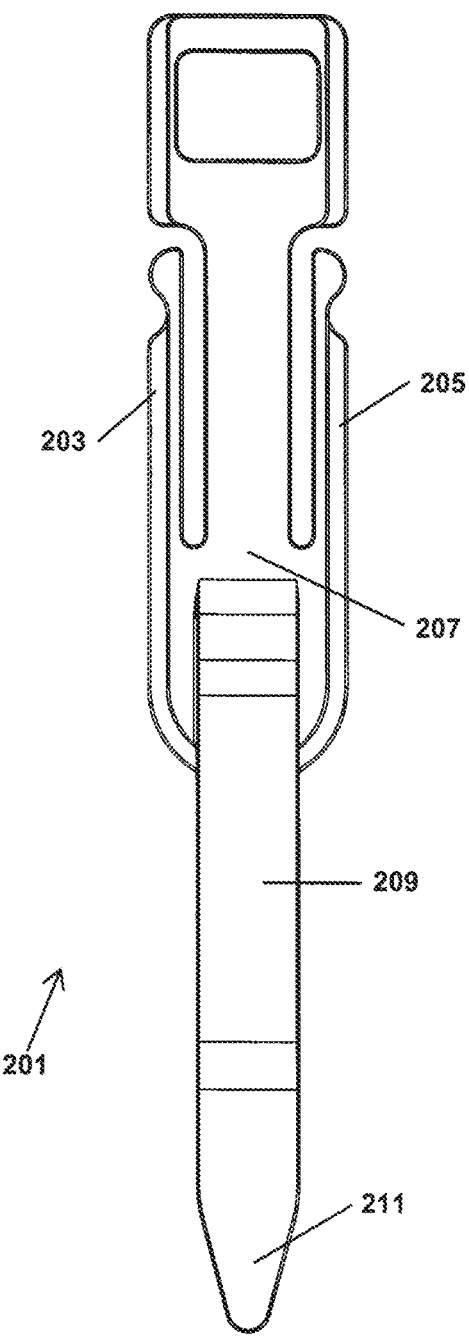
FIG. 31 is an elevational view of a retractor blade docking anchor showing a pointed tip of the docking anchor for penetrating an intervertebral disc.

With reference to FIG. 31, the docking anchor 201 has a body 207 sized to fit within a slot of a retractor blade, such as a slot 190 of the blade 12 (see FIG. 5). The body 207 is advanced into the open end 192 of the slot 190 and slid therein until reaching the closed end 194 of the slot. At this position, a blade 209 of the docking anchor 201 extends beyond the distal end 34 of the blade 12 such that a tip 211 of the blade 209 can penetrate a surface of an intervertebal disc during surgery. Further, the ratchet arms 203, 205 of the docking anchor 201 are resiliently biased apart to engage serrations 200, 202 of the blade to secure the docking anchor 201 to the blade 12 at a desired position.

Figure 32:
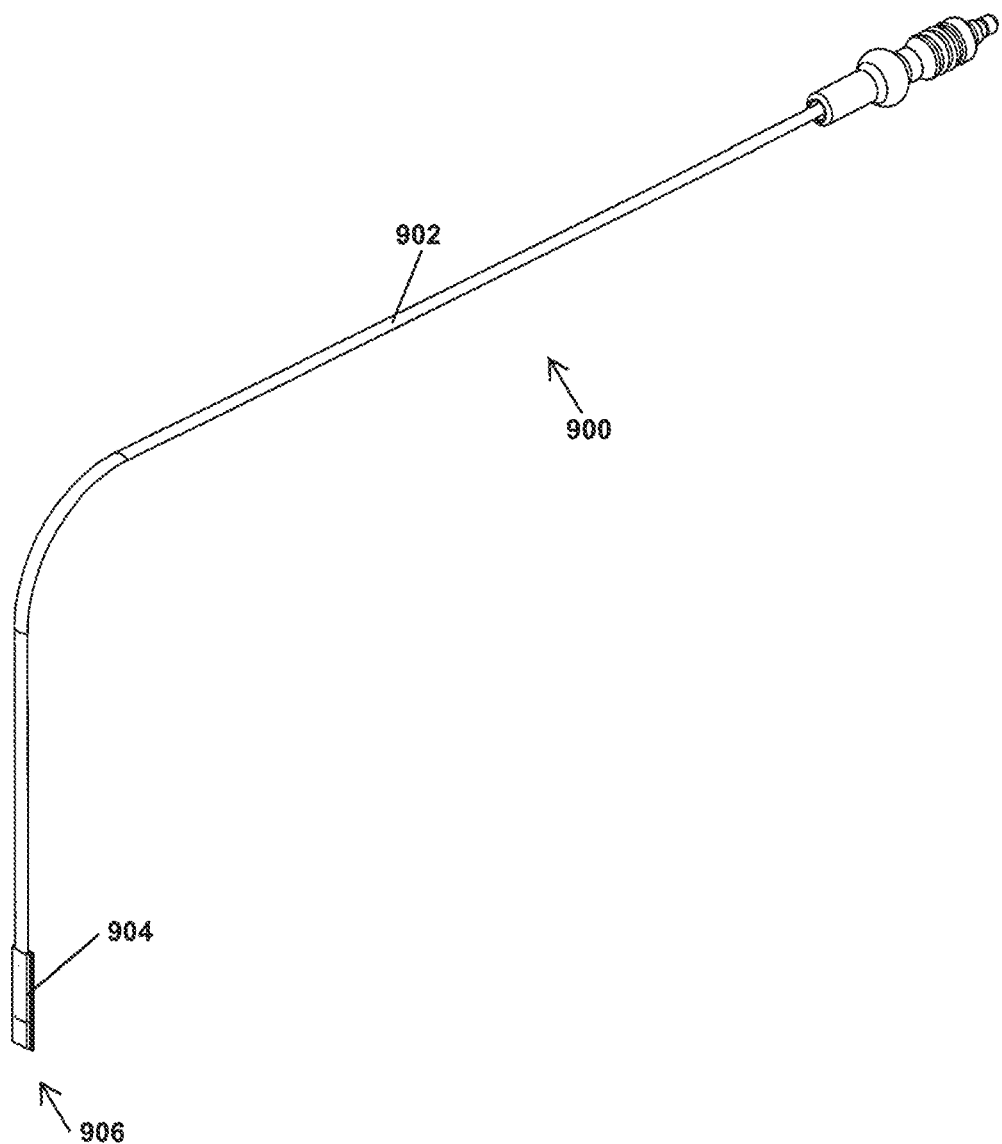
FIG. 32 is a perspective view of a light source showing a flexible fiber optic cable.

As shown in FIG. 32, a disposable light source 900 for use with the retractor 600 is shown. The disposable light source 900 has a flexible fiber optic cable 902 and an anodized aluminum tip 904 sized to fit within a slot of a retractor blade, such as the slot 190 of retractor blade 60 shown in FIG. 5. The tip 904 includes a light source 906 for illuminating a retracted incision, such as the working channel 640 shown in FIG. 22.

Figure 33:
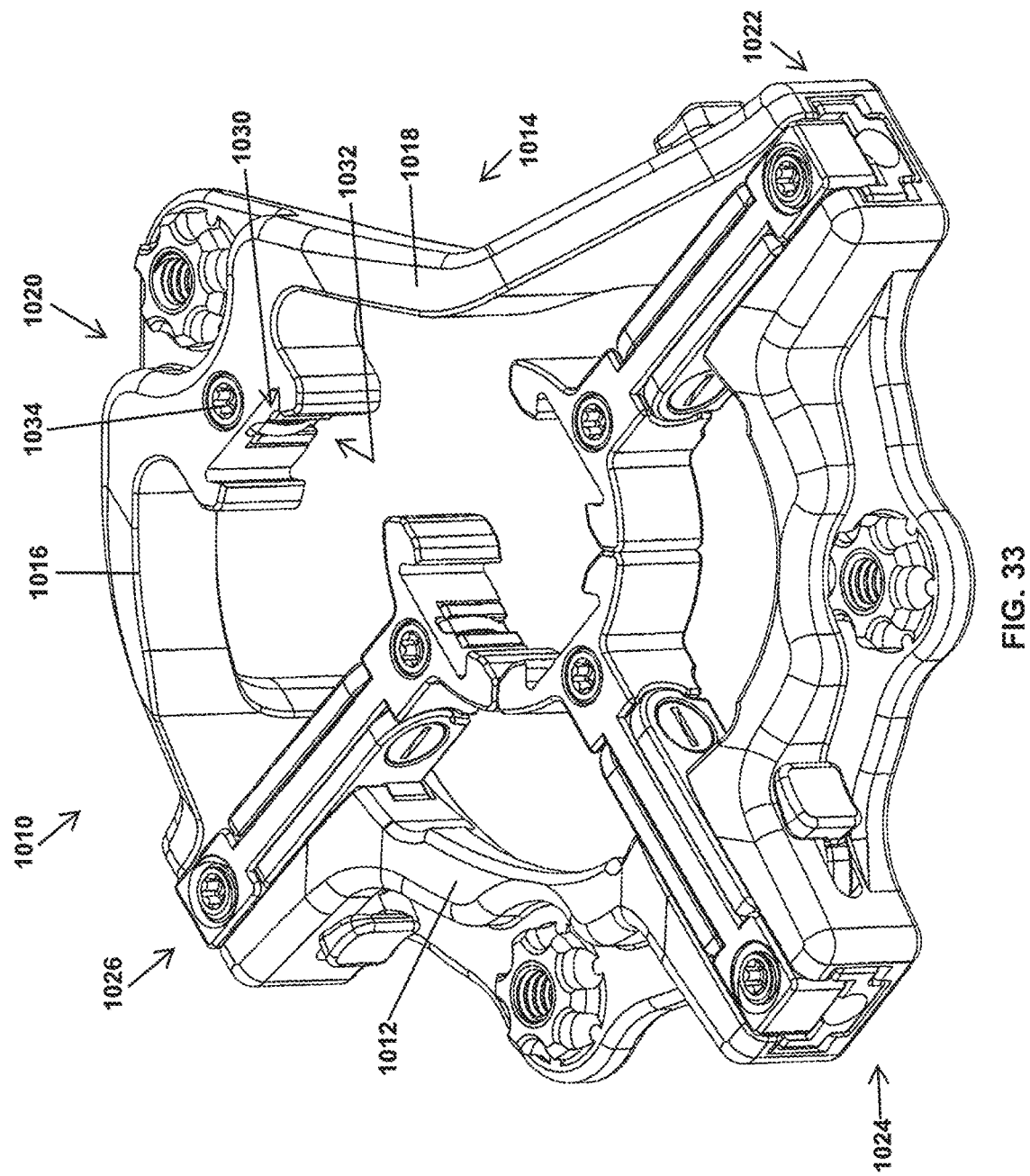
FIG. 33 is a perspective view of a retractor in accordance with another form of the present invention showing an elevated portion of the retractor frame.

With reference to FIG. 33, a retractor 1010 in accordance with another aspect of the present invention is illustrated. The retractor 1010 is substantially similar to the retractor 600 such that the differences therebetween will be highlighted. The retractor 1010 has a frame 1012 including a raised portion 1014 that accommodates placement of the retractor 1010 adjacent a patient's iliac crest. The raised portion 1014 includes a pair of arms 1016, 1018 supporting an operating mechanism 1020 disposed above the plane of the other operating mechanisms 1022, 1024, 1026. The operating mechanism 1020 has a dovetail recess 1030 and a wedge lock 1032 operable via a screw 1034 similar to operating mechanism 604 discussed above; however, the operating mechanism 1010 lacks a slider to retract the associated retractor blade.

Figure 34:
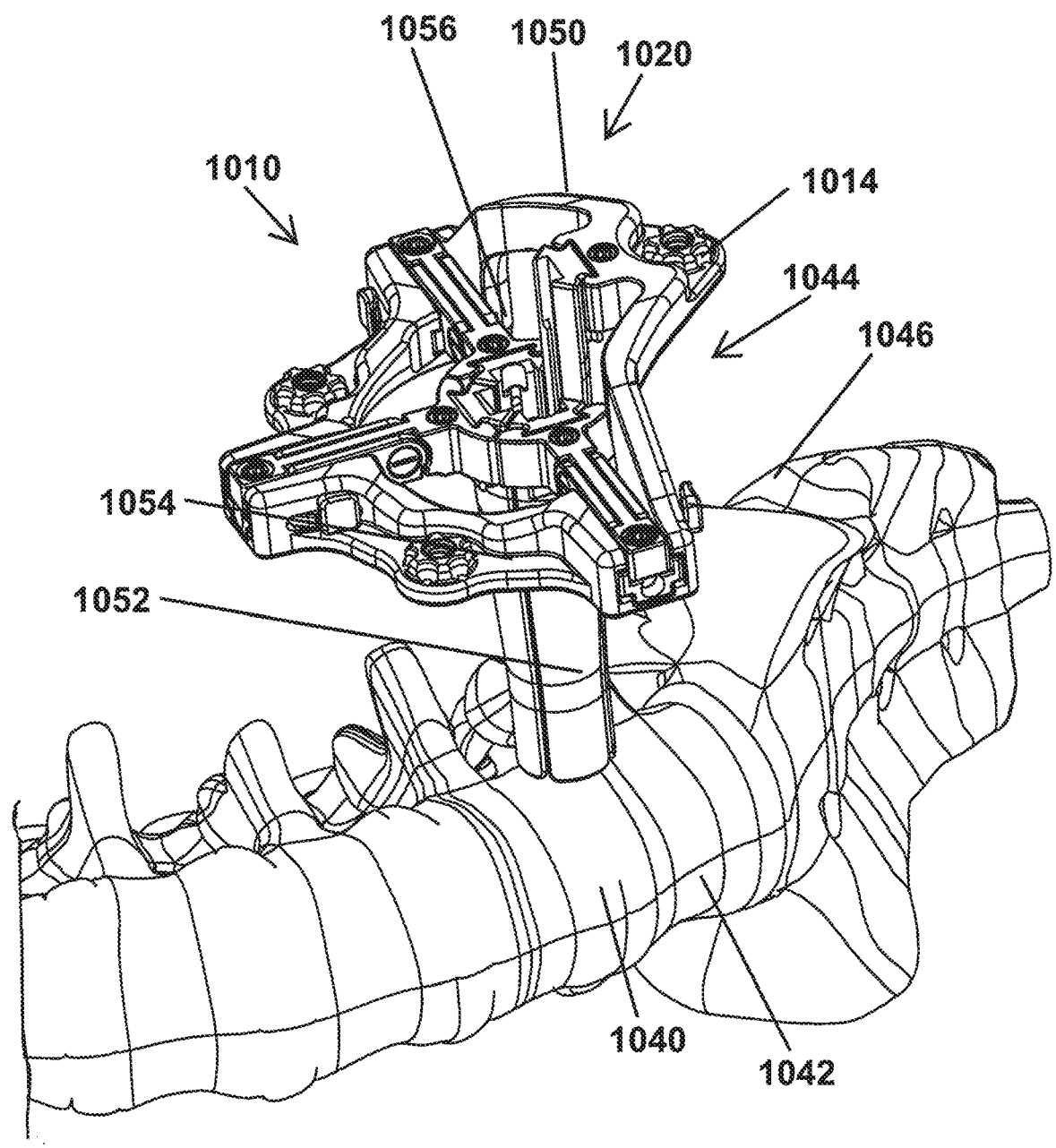
FIG. 34 is a perspective view of the retractor of FIG. 33 showing blades mounted on the retractor and disposed adjacent an intervertebral disc between L4 and L5 vertebrae.
Figure 35:
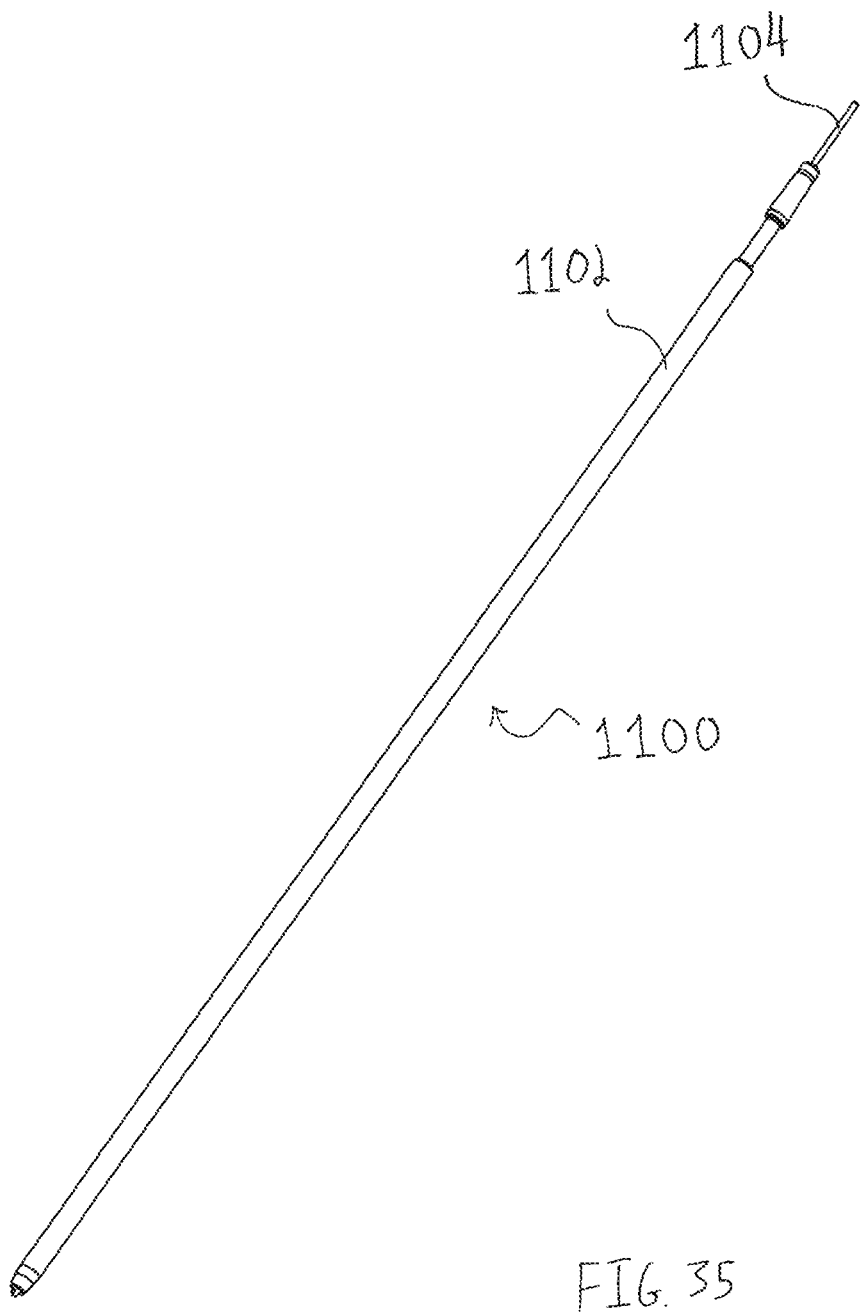
FIG. 35 is a perspective view of a pin dilator that may be used with the guide dilators of FIGS. 1, 7, and 8 in place of a separate guide wire and a first dilator.

As shown in FIG. 34, the retractor 1010 may be used to retract tissues adjacent lumbar vertebra 1040, 1042. The raised portion 1014 of the retractor 1010 provides spacing 1044 between the operating mechanism 1020 and an iliac crest 1046 of the patient. In this manner, a surgeon can position the raised portion 1014 upon a patient's hip while keeping the retractor 1010 relatively flush with the skin of the patient. The operating mechanism 1020 utilizes a longer blade 1050 to compensate for the distance the operating mechanism 1020 is elevated above the other operating mechanisms. Although blade 1050 is longer than the remaining blades 1052, 1054, 1056, the blades 1050, 1052, 1054, 1056 may all be inserted using a single guide dilator, such as guide dilator 10, in a manner substantially similar to the processes described above. The blade 1050 has a longer slot than the blades 1052, 1054, 1056 so that the distal ends of the blades 1050, 1052, 1054, 1056 will be disposed evenly at the leading end portion 46 of the guide dilator 10.

A pin dilator 1100 may also be used with the guide dilators 10, 300, 410 and surgical techniques described above. The pin dilator 1100 includes a dilator 1102 and a guide wire 1104 fixed in the dilator 1102. The pin dilator 1100 is an easy-to-handle tool that may be used in place of a conventional guidewire 514 and first dilator 516 (see FIG. 11).

Figure 36:
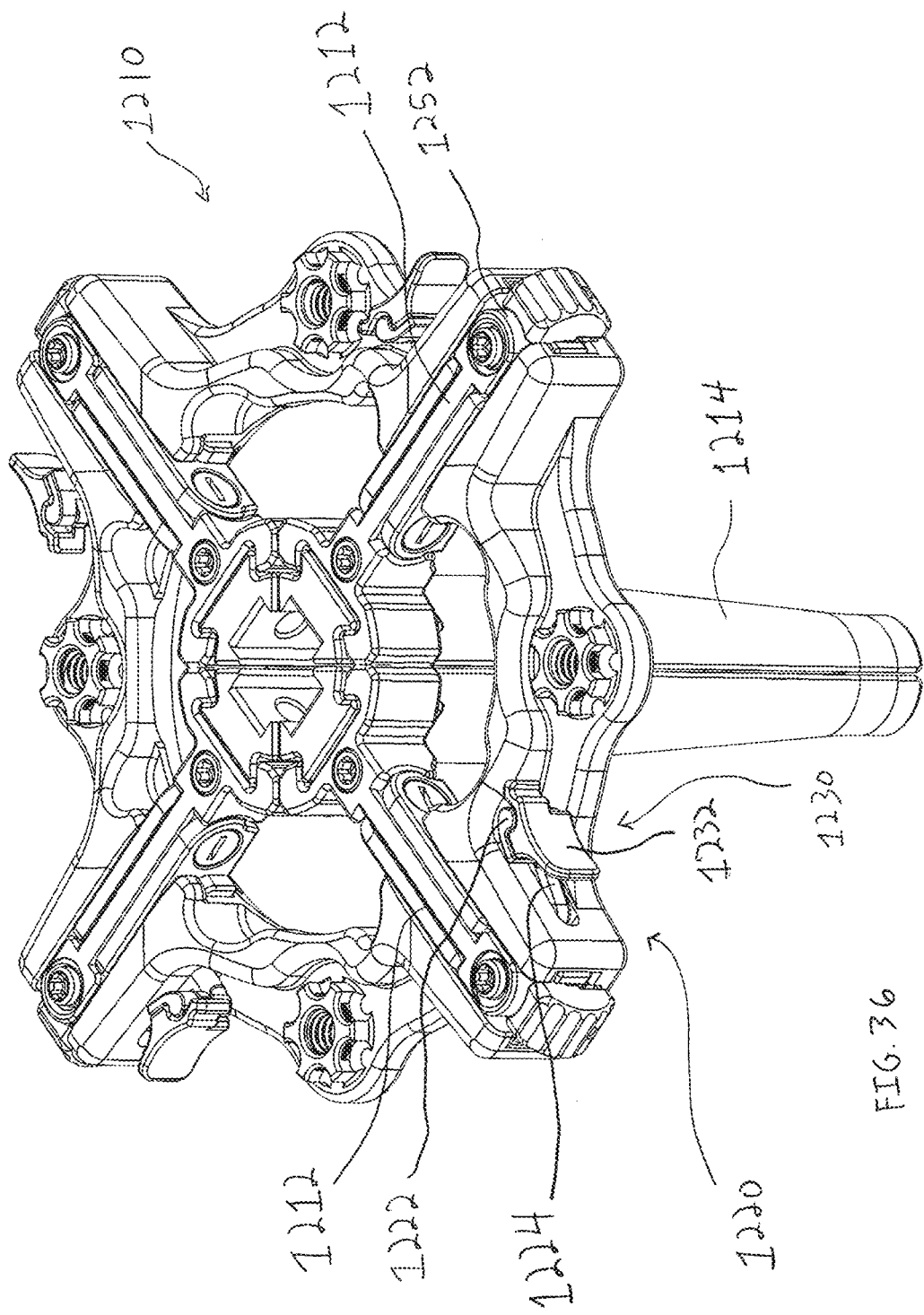
FIG. 36 is a perspective view of a retractor in accordance with another form of the present invention that includes locking mechanisms for locking sliders of the retractor.
Figure 37:
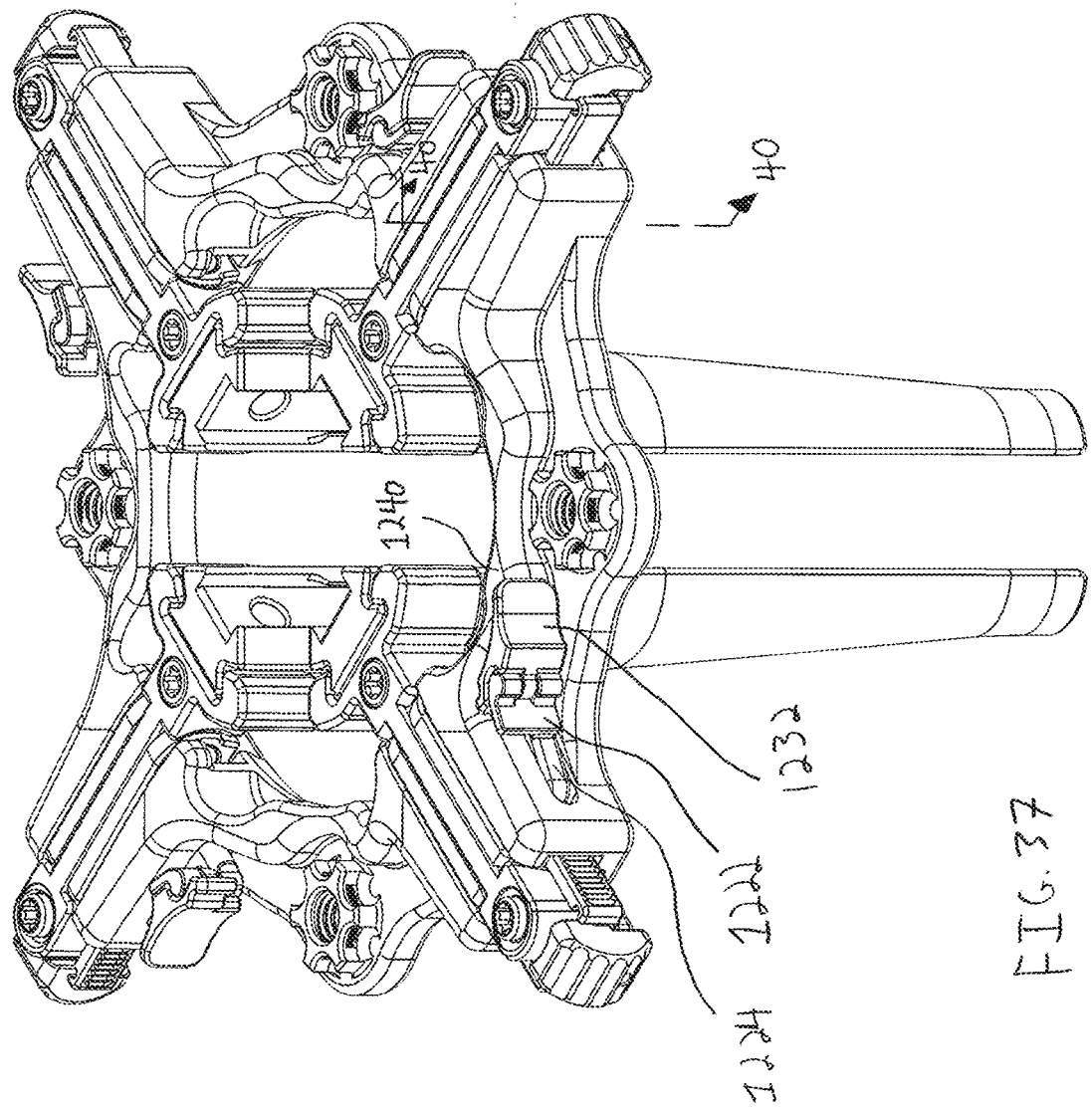
FIG. 37 is a perspective view of the retractor of FIG. 36 showing sliders and attached retractor blades of the retractor in a retracted configuration which generally forms a working channel between the blades.

Turning to FIGS. 36-41, a retractor 1210 in accordance with the present invention is shown. The retractor 1200 is similar in a number of ways to retractors 600 and 1010 and includes sliders 1212 connected to retractor blades 1214 which retract radially outward to enlarge an incision. The retractor 1200 includes a ratchet mechanism 1220 comprising a button 1222 and an integral tooth 1224 similar to the button 724 and tooth 717 (see FIG. 28) for selectively engaging the associated slider 1212, as shown in FIG. 36. The retractor 1200 further includes a slider lock mechanism 1230 comprising a lock latch 1232 that is pivotally connected to the button 1222. The slider lock mechanism 1230 fixes the tooth 1224 with the slider 1212 and reduces the chance that the ratchet mechanism 1220 may be accidentally disengaged during operation, which would permit the slider 1212 and associated retractor blade 1214 to shift radially inward. More specifically, when the slider 1212 as been retracted, a surgeon may pivot the lock latch 1232 toward a frame 1240 of the retractor 1200 such that the latch 1232 abuts the frame 1240 and restricts the button 1222 and integral tooth 1224 thereof from moving out of engagement with the slider 1212, as shown in FIG. 37.

Figure 38:
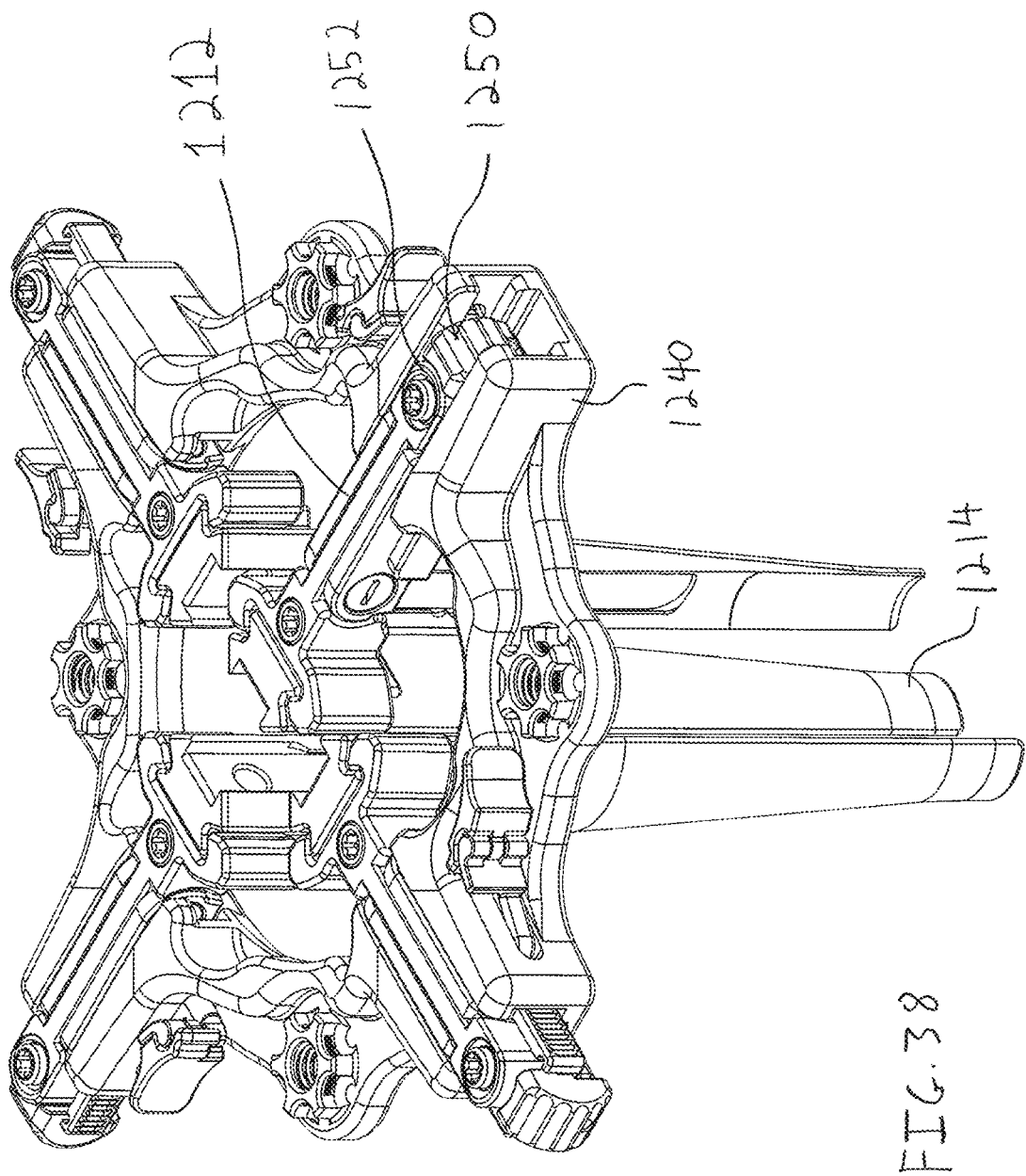
FIG. 38 is a perspective view of the retractor of FIG. 36 showing one of the sliders in a beyond center position where the retractor blade connected to the slider has been moved radially inward to a point beyond a center of the working channel.
Figure 39:
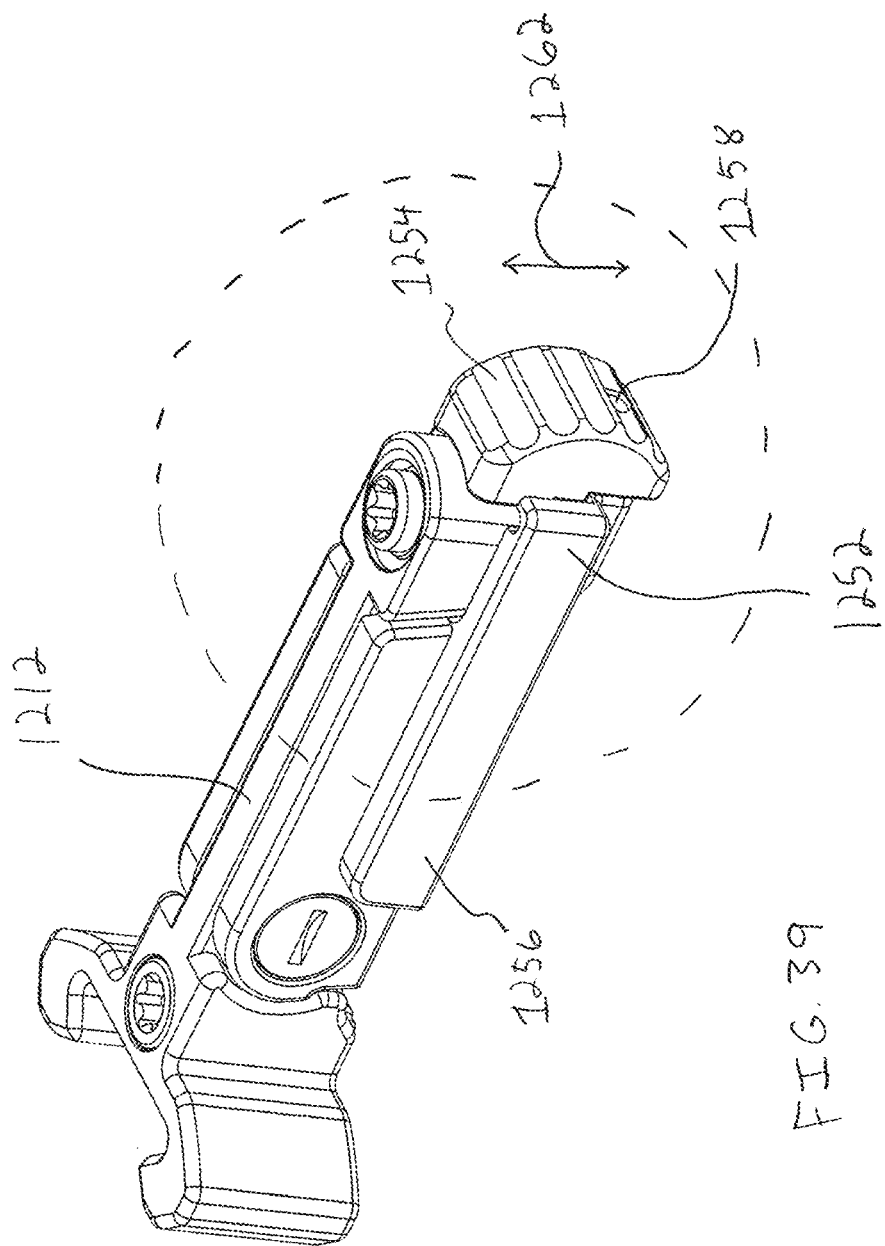
FIG. 39 is a perspective view of the slider shown in the beyond center position in FIG. 38 showing the slider removed from the retractor frame and a dashed circle extending about a locking mechanism of the slider.
Figure 40:
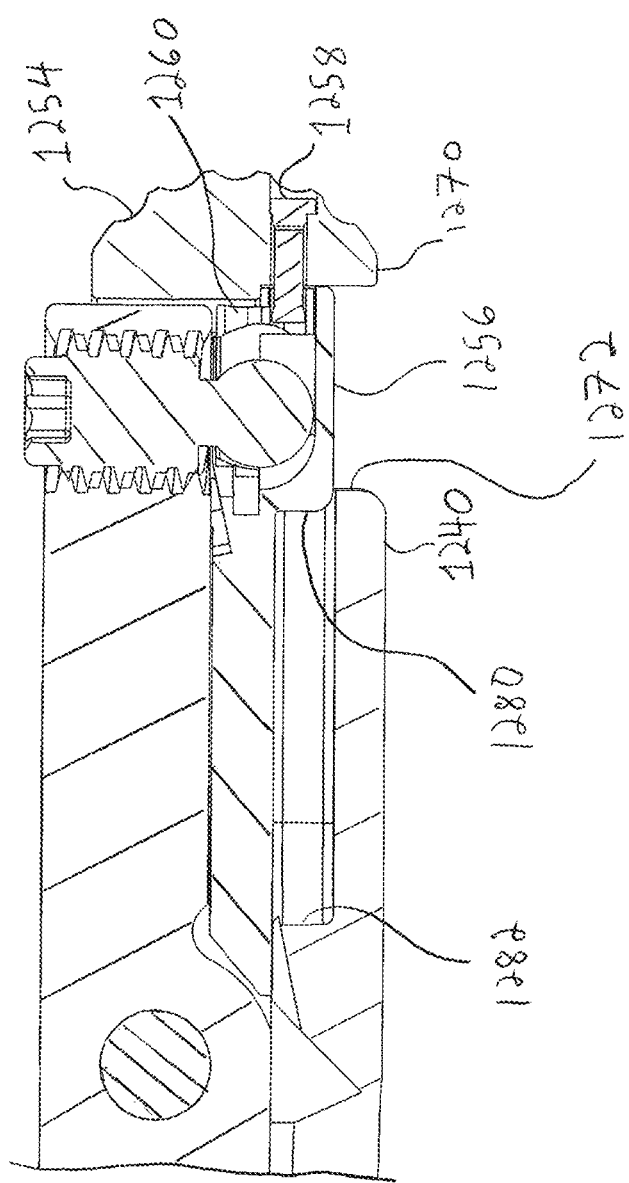
FIG. 40 is a cross sectional view taken across line 40-40 in FIG. 37 showing the slider in a retracted position and a lock button of the locking mechanism in a lowered locked position.

The retractor 1200 also permits a surgeon to move the sliders 1212 radially inward to a beyond center position where the associated retractor blade 1214 connected to the slider 1212 is beyond a center of a working channel defined by the retracted retractor blades 1214, as shown in FIG. 38. The retractor 1200 has a beyond center locking mechanism 1250 that controls whether a radially outer end 1252 of the slider 1212 may pass radially inward beyond the retractor frame 1240. The beyond center locking mechanism 1250 includes a lock button 1254 shiftably connected to a base 1256 of the slider 1212 by a pin 1258, as shown in FIGS. 39 and 40. The pin 1258 travels in a slot 1260 of the base 1256 and permits the lock button 1254 to shift up and down as shown by arrow 1262 in FIG. 39.

Figure 41:
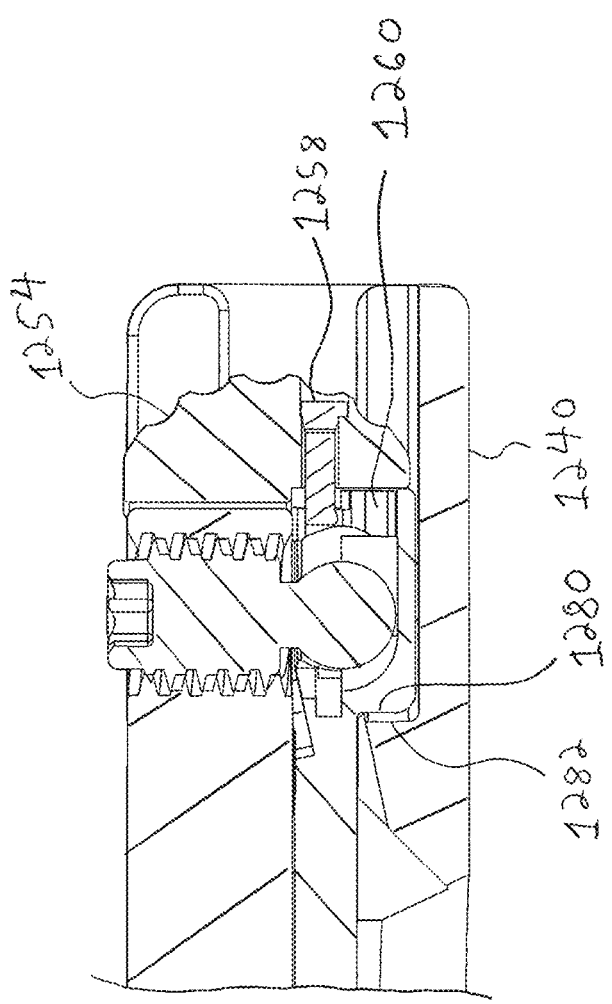
FIG. 41 is a cross sectional view similar to FIG. 40 showing the slider in the beyond center position and the lock button in a raised unlocked position.

For example, while retracting an incision, stray tissues may extend into the working channel between blades 1214. In prior approaches, a surgeon would need to insert a tool into the surgical field and tuck the stray tissues behind the nearby retractor blades 1214 to remove the stray tissues from the working channel. By contrast, a surgeon utilizing the retractor 1200 who encounters stray tissues in the working channel, may simply shift the button 1254 upward so that a lower end 1270 is in clearance with a radially outer wall 1272 of the retractor frame 1240, as shown in FIGS. 40 and 41. The surgeon then may move the slider 1212 and retractor blade 1214 radially inward to the beyond center position, as shown in FIG. 38. The slider 1212 and retractor frame 1240 include confronting surfaces 1280, 1282 that abut and limit movement of the slider 1212 radially inward to a predetermined position along the retractor frame 1240.

Figure 42:
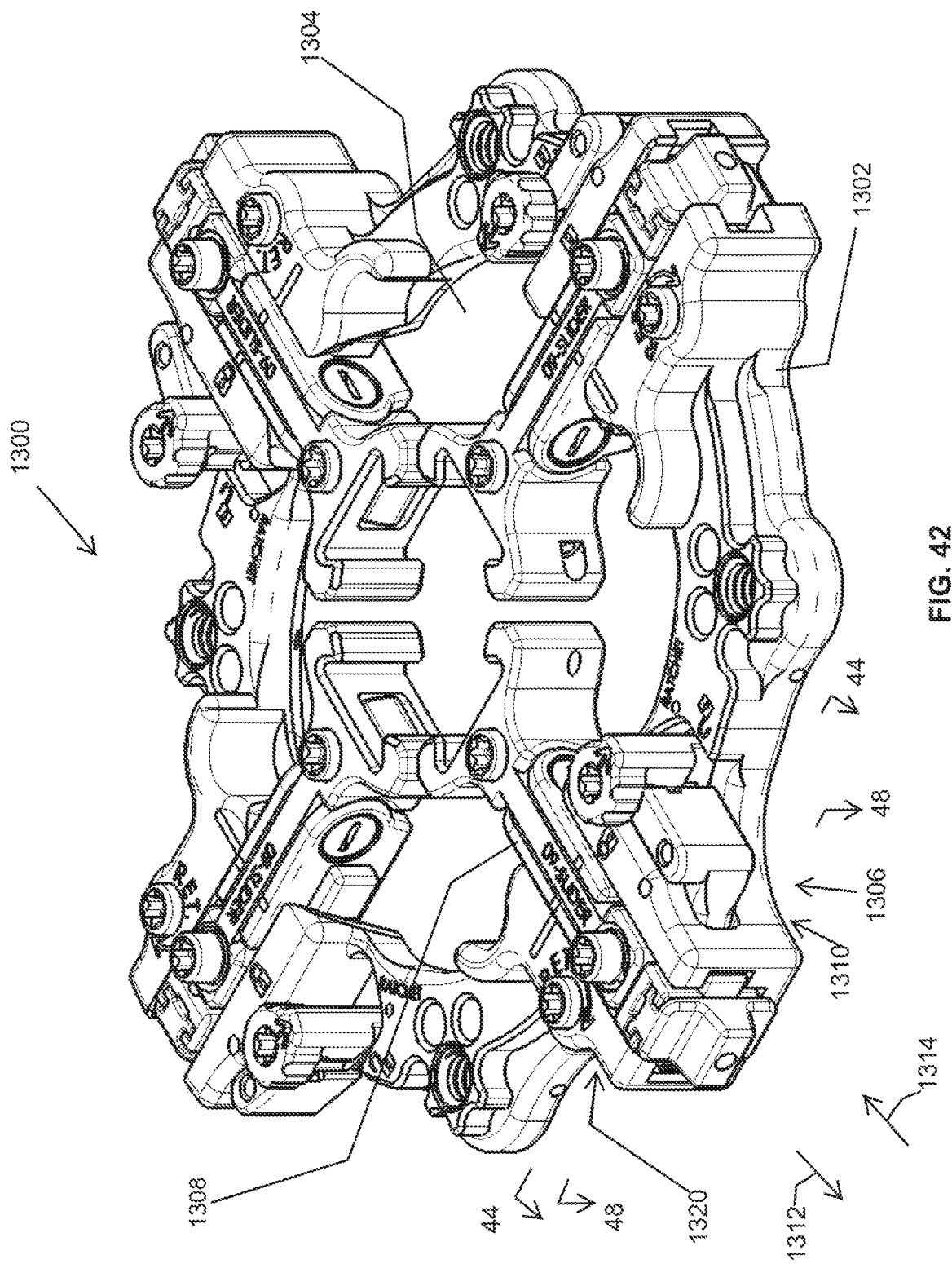
FIG. 42 is a perspective view of a retractor in accordance with another form of the present invention showing sliders of the retractor in extended positions thereof.

With reference to FIG. 42, a retractor 1300 is provided that is similar in many respects to the retractors discussed above. The retractor 1300 has a frame 1302 extending about a central opening 1304 and operating mechanisms 1306 for connecting tissue engaging members, such as retractor blades, to the frame 1302. The operating mechanisms 1306 each include a slider 1308 to which a blade is connected and a ratchet mechanism 1310 for selectively resisting movement of the slider 1308 in direction 1314 toward an extended position thereof.

The operating mechanism 1306 further includes a slider linear drive 1320 for driving the slider 1308 in direction 1312 opposite direction 1314 toward a retracted position thereof. Each operating mechanism 1306 may include an associated slider linear drive 1320, which permits a surgeon to retract all of the sliders 1308 and blades connected thereto apart using the slider linear drives 1320 to enlarge an incision. The slider linear drive 1320 provides for ease in controlling retraction of the slider 1308 by using a tool engaged with the slider linear drive 1320 versus other systems that require use of tools that engage the blades directly for spreading the blades apart. These prior tools may be undesirable in some procedures because they are inserted between the blades and used to spread the blades apart, which involves positioning a portion of the tool in the working channel created by the retractor. It will be appreciated that although the slider linear drive 1320 provides advantages over tools that engage the blades directly for spreading the blades apart, the retractor 1300 may also be used with these prior tools in addition to or in place of the linear drive mechanism 1320 for retracting the blades.

Figure 43:
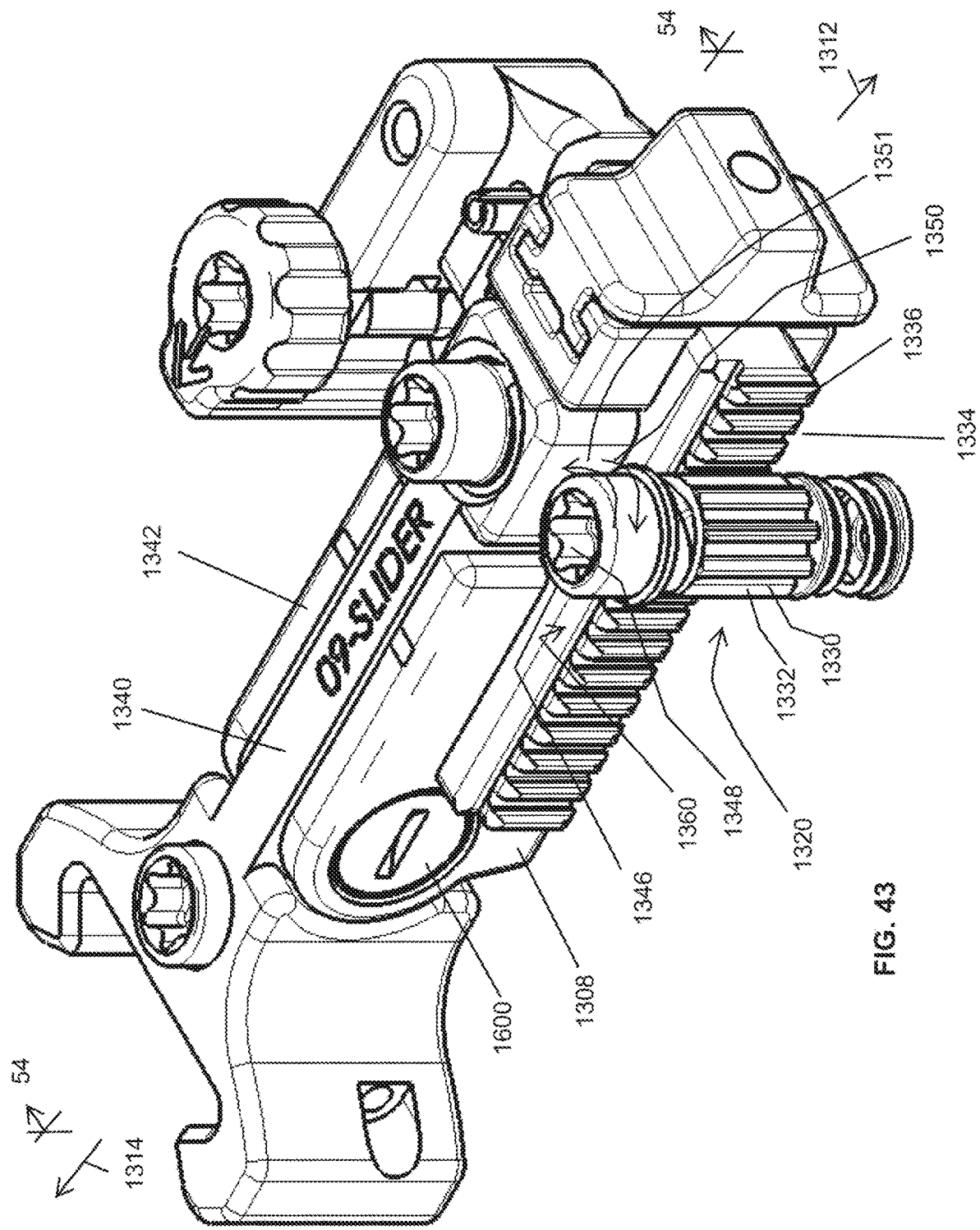
FIG. 43 is a perspective view of one of the sliders of the retractor of FIG. 42 showing a slider linear drive and a ratchet mechanism engaged on opposite sides of the slider.

With reference to FIG. 43, the slider linear drive 1320 includes a pinion 1330 with teeth 1332 that engage teeth 1334 of a rack 1336 of the slider 1308. In one form, the slider 1308 has an inner member 1340 and an outer member 1342. The inner member 1340 is pivotally connected to the outer member 1342 via a pivot member such as a pivot pin 1600. The outer member 1342 includes the rack 1336 such that operation of the slider linear drive 1320 drives the outer member 1342 and inner member 1340 connected thereto in direction 1312 toward the retracted position thereof. The slider linear drive 1320 further includes a drive cap 1346 connected to the pinion 1330 at the upper end thereof as described hereinafter. The drive cap 1346 has a tool engaging portion, such as a socket 1348 configured to receive a hexalobular driver. In use, a surgeon may insert the hexalobular driver into the socket 1348 and turn the drive cap 1346 in a drive direction 1350. This causes rotation of the pinion 1330 in drive direction 1350 and, by way of the engagement of the pinion teeth 1332 and the rack teeth 1334, generates sliding movement of the slider 1308 in direction 1312 relative to the frame 1302 such that the slider 1308 slides toward the retracted position thereof.

Figure 44:
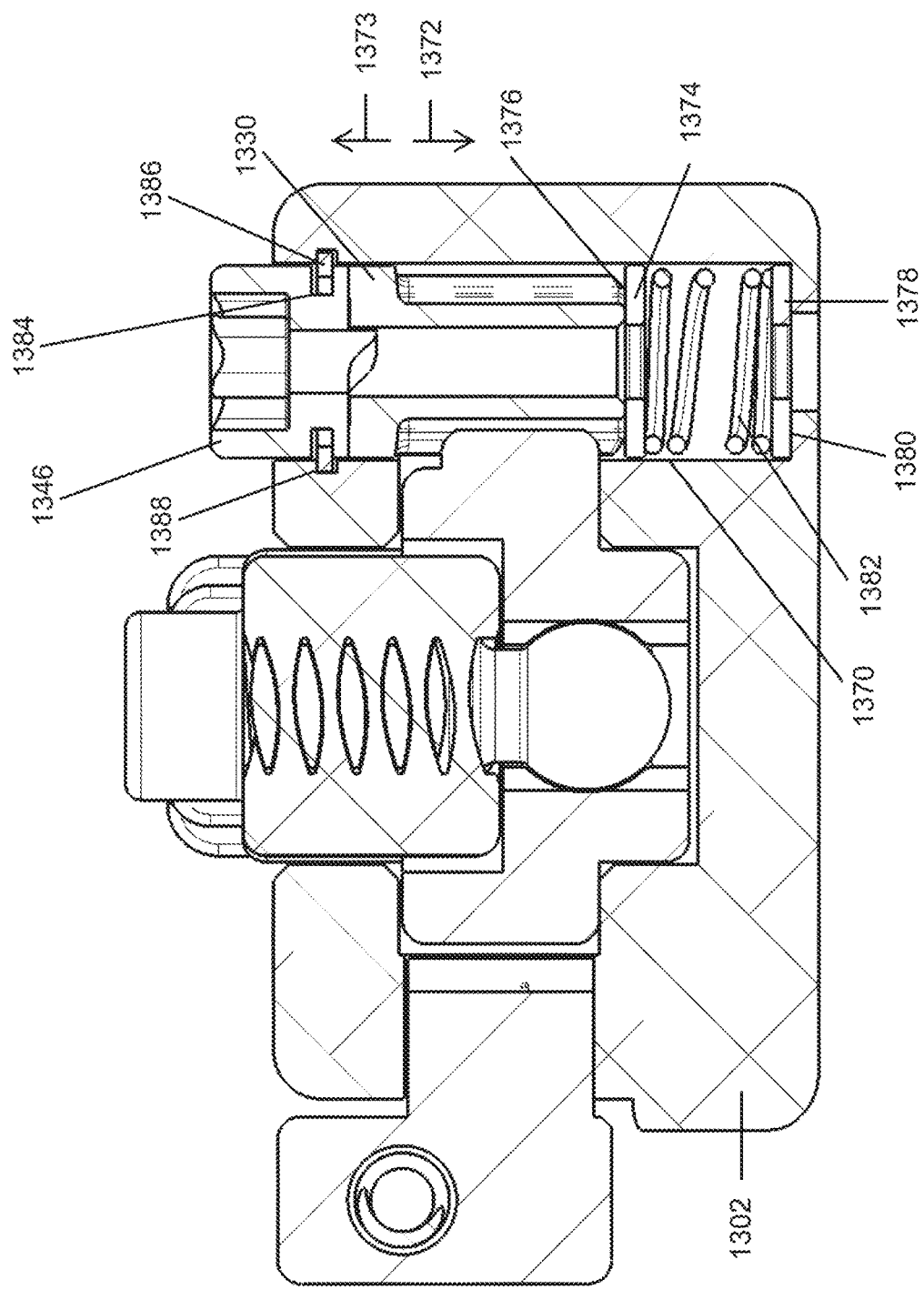
FIG. 44 is a cross-sectional view taken across line 44-44 in FIG. 42 showing a drive cap and a pinion of the slider linear drive received in a bore hole of the frame.

With reference to FIGS. 43 and 44, the slider linear drive 1320 includes an anti-reverse device 1360 that limits rotation of the pinion 1330 to rotation in drive direction 1350. By limiting rotation of the pinion 1330 to rotation in the drive direction 1350, the retractor 1300 limits the likelihood of a surgeon using the hexalobular driver and the drive cap 1346 to unintentionally move the slider 1308 in direction 1314 and collapsing the working channel formed by the retracted blades.

With reference to FIG. 44, the drive cap 1346 and pinion 1330 are received in a bore hole 1370 of the frame 1302. Both the drive cap 1346 and the pinion 1330 can rotate in drive direction 1350 within the bore hole 1370. The drive cap 1346 has a groove 1384 extending thereabout that receives a split ring 1386. The split ring 1386 extends into an annular recess 1388 extending about the bore hole 1370. The split ring 1386 thereby retains the drive cap 1346 at a predetermined vertical position at an upper end of the bore hole 1370 while permitting the drive cap 1346 to rotate within the bore hole 1370.

In addition to being rotatable within the bore hole 1370, the pinion 1330 can shift vertically in direction 1372 and disengage from the drive cap 1346 in response to a surgeon turning the drive cap 1346 in a reverse direction 1351 (see FIG. 43). This disengagement inhibits the pinion 1330 from driving the slider 1308 in direction 1314 toward the extended position thereof even though the surgeon is rotating the drive cap 1346 in the reverse direction 1351. More specifically, the anti-reverse device 1360 includes a washer 1374 abutting a lower end 1376 of the pinion 1330 and a washer 1378 abutting a seat 1380 of the frame 1302, as shown in FIG. 44. There is a biasing member, such as a spring 1382, positioned between the washers 1374, 1378. The spring 1382 biases the washer 1374 upward and, in turn, biases the pinion 1330 upward in direction 1373 against the drive cap 1346. The spring 1382 may be partially compressed when the drive cap 1346, pinion 1330, spring 1382, and washers 1374, 1378 are assembled within the bore hole 1370 which causes the spring 1382 to press the pinion 1330 against the underside of the drive cap 1346.

If the drive cap 1346 is rotated in reverse direction 1351, the pinion 1330 is shifted downwardly in direction 1372 (see FIG. 44) and disengages from the drive cap 1346 due to camming engagement between surfaces of the drive cap 1346 and pinion 1330, as discussed in greater detail below. When the pinion 1330 shifts downwardly in direction 1372, the pinion 1330 urges the washer 1374 toward the washer 1378 and further compresses the spring 1382. The spring 1382 resiliently urges the pinion 1330 upwardly in direction 1373 in response to this compression.

Because the surgeon's rotation of the drive cap 1346 in the reverse direction 1351 does not produce any movement of the slider 1308, the surgeon should readily appreciate that the drive cap 1346 is being rotated in an incorrect direction and can then rotate the drive cap 1346 in the drive direction 1350. As the surgeon rotates the drive cap 1346 in drive direction 1350, the spring 1382 urges the pinion 1330 against the drive cap 1346. The rotating drive cap 1346 eventually reaches the correct orientation relative to the pinion 1330 where the surfaces of the drive cap 1346 and pinion 1330 can mate and fully engage as discussed in greater detail below. The spring 1382 thereby helps return the drive cap 1346 and the pinion 1330 into mating engagement as the drive cap 1346 is rotated in the drive direction 1350 after the drive cap 1346 was rotated in the reverse direction 1351.

With reference to FIGS. 45 and 46, the anti-reverse device 1360 includes cooperating protrusions of 1400, 1402 of the pinion 1330 and protrusions 1404, 1406 of the drive cap 1346. When the drive cap 1346 is turned in drive direction 1350, the protrusions 1400, 1404 and 1402, 1406 mate and fully engage which causes turning of the pinion 1330 in drive direction 1350. When the drive cap 1346 is turned in the reverse direction 1351, the protrusions 1404, 1406 disengage from the protrusions 1400, 1402 and ride along the protrusions 1400, 1402. Even though the drive cap 1346 may be turned in the reverse direction 1351, this turning does not translate into turning of the pinion 1330 in the reverse direction 1351 due to the disengagement of the protrusions 1404, 1406 from the protrusions 1400, 1402.

More specifically and with reference to FIG. 45, the protrusions 1400, 1402 of the pinion 1330 include generally vertically extending drive surfaces 1410, 1412 and cam surfaces 1418, 1420 that ramp up to upper ends of the drive surfaces 1410, 1412. The pinion 1330 includes lands 1414, 1416 extending circumferentially away from the drive surfaces 1410 and which lead into the cam surfaces 1418, 1420.

With reference to FIG. 46, the protrusions 1404, 1406 of the drive cap 1346 likewise have generally vertically extending drive surfaces 1422, 1424 and cam surfaces 1430, 1434 that ramp downwardly to lower ends of the drive surfaces 1422, 1424. The drive cap 1346 has lands 1426, 1428 extending circumferentially away from the drive surfaces 1422, 1424 and which lead into the cam surfaces 1430, 1434. It is noted that FIG. 46 shows the drive cap 1346 in an upside-down orientation such that the cam surfaces 1430, 1434 are shown ramping upward toward the drive surfaces 1422, 1424, but the cam surfaces 1430, 1434 would be oriented to ramp downward toward the drive surfaces 1422, 1424 when the drive cap 1346 and pinion 1330 are assembled.

When the drive cap 1346 and the pinion 1330 are positioned in the frame bore hole 1370, the protrusions 1404, 1406 of the drive cap 1346 are positioned adjacent the lands 1414, 1416 of the pinion 1330. When the surgeon inserts the hexalobular driver into the socket 1348 of the drive cap 1346 and turns the drive cap 1346 in drive direction 1350, this causes the drive surface 1422 of the drive cap 1346 to abut the drive surface 1410 of the pinion 1330 and causes the drive surface 1424 of the drive cap 1346 to abut the drive surface 1412 of the pinion 1330. Because of the abutting drive surfaces 1410, 1422 and 1412, 1424, turning of the drive cap 1346 in the drive direction 1350 produces corresponding turning of the pinion 1330 in drive direction 1350 and causes retraction of the slider in direction 1312.

Conversely, if the surgeon rotates the hexalobular driver engaged with the drive cap 1346 in the reverse direction 1351, the cam surface 1430 of the drive cap 1346 cammingly engages the cam surface 1418 of the pinion 1330 and the cam surface 1434 of the drive cap 1346 cammingly engages the cam surface 1420 of the pinion 1330. This camming engagement between the surfaces 1430, 1418 and 1434, 1420 shifts the pinion 1330 downward in direction 1372 (see FIG. 44) within the bore hole 1370 and compresses the spring 1382. The downward movement of the pinion 1330 permits the projections 1404, 1406 of the drive cap 1346 to snap past the projections 1400, 1404 of the pinion 1330 as the drive cap 1346 is turned in the reverse direction 1351 thereby inhibiting the drive cap 1346 from causing similar turning of the pinion 1330 in reverse direction 1351. In effect, turning the drive cap 1346 in reverse direction 1351 moves the drive surfaces 1422, 1424 of the drive cap 1346 away from the drive surfaces 1410, 1412 of the pinion 1330 whereas turning the drive cap 1346 in drive direction 1350 brings the drive surfaces 1422, 1424 into engagement with the drive surfaces 1410, 1412. Because the drive surfaces 1410, 1422 and 1412, 1424 do not engage when the drive cap 1346 is turned in reverse direction 1351, the drive cap 1346 is unable to cause rotation of the pinion 1330 in the reverse direction 1351.

With reference to FIGS. 47-50, the ratchet mechanism 1310 includes an actuator, such as the actuator button 1450, which is similar to the actuator buttons 724, 824, 1222 discussed above. The button 1450 includes a projection, such as an integral projection tooth 1452, which is similar to the projection teeth 717, 1224 discussed above. The tooth 1452 engages recesses, such as depressions 1454, between adjacent teeth 1454A on a side of the slider outer member 1342 opposite the rack 1336. The depressions 1454 are similar to the depressions 723 discussed above and both recesses receive a cooperating tooth 1452, 717. The button 1450 has a through opening 1456 that receives a shaft 1458 rotatably mounted at its ends to the frame 1302 for pivotally mounting the button 1450 to the frame 1302. The ratchet mechanism 1310 further includes a slider lock mechanism 1460 that reduces the chance of the ratchet mechanism 1310 being accidentally disengaged during operation which would permit the slider 1308 and associated retractor blade to shift radially inward. The slider lock mechanism 1460 includes a lock latch 1462 pivotally connected to the button 1450 by a pin 1464.

With reference to FIGS. 49, 51, and 53 the lock latch 1462 may be pivoted between an unlocked position (see FIG. 49), a ratchet position (see FIG. 51), and a locked position (see FIG. 53) for limiting operation of the button 1450 as discussed in greater detail below. The lock latch 1462 has an orientation indicia 1470 that may be used to provide visual or tactile feedback to the surgeon regarding the position of the lock latch 1462. Further, the frame 1302 may have corresponding indicia, such as an unlocked indicia 1472 (see FIG. 49), a ratchet indicia 1474 (see FIG. 51), and a locked indicia 1476 (see FIG. 51) which indicate that the lock latch 1462 is in a desired position once the orientation indicia 1470 is aligned with the respective indicia 1472, 1474, 1476.

Returning to FIG. 47, the button 1450 and the lock latch 1462 include interdigitated loops 1480, 1482 extending about the pin 1464. The loops 1480, 1482 and pin 1464 form a hinge that permits pivoting of the lock latch 1462 relative to the button 1450. The lock latch 1462 includes a handle portion 1484 that may include a scalloped outer surface to aid gripping by the surgeon and a tool receiving portion 1486. As an example, the tool receiving portion 1486 may have a socket for receiving a hexalobular driver so that the surgeon may pivot the lock latch 1462 using the hexalobular driver. The hexalobular driver may be used when tissue pressure against the blades requires more persuasion to unlock the slider 1308 than the surgeon can apply with her finger tip(s).

Figure 47:
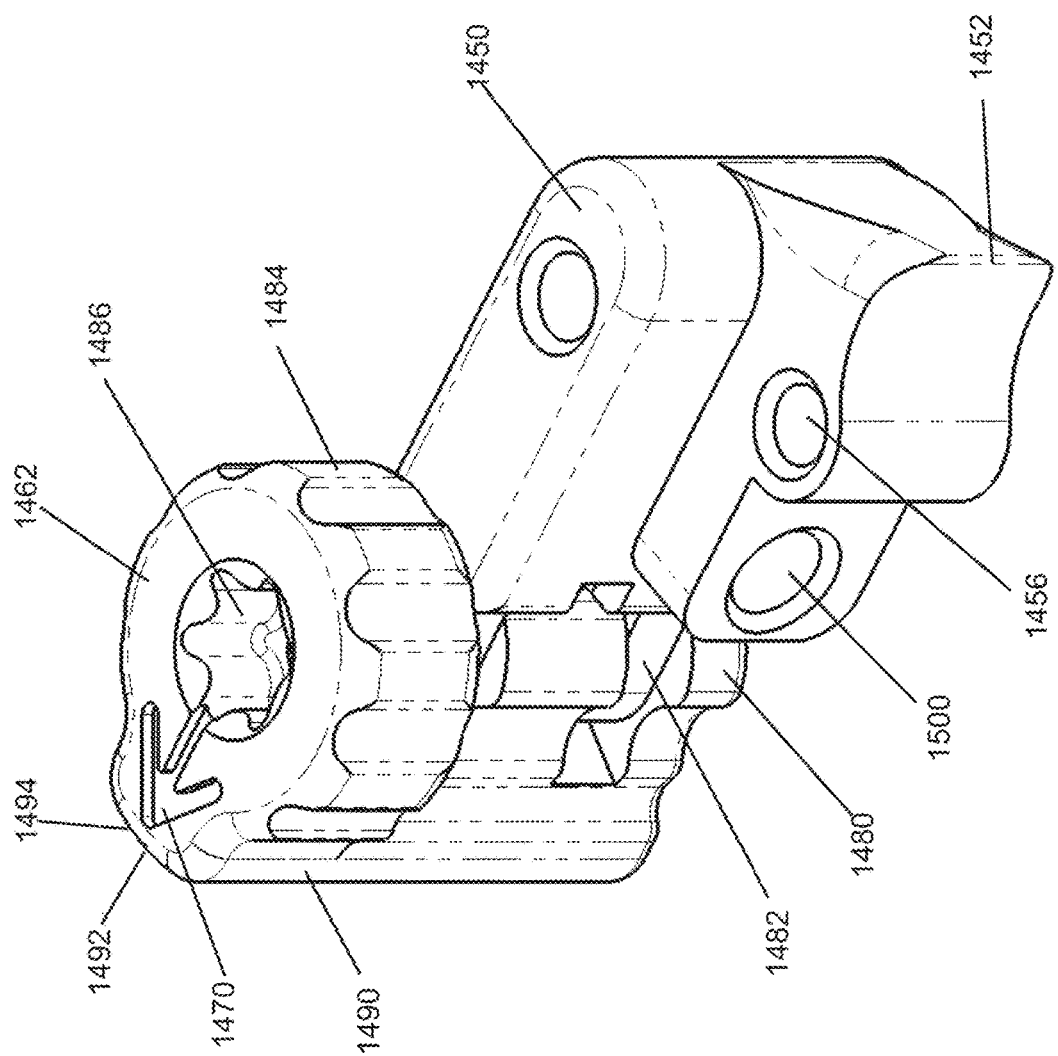
FIG. 47 is a perspective view of a button and a lock latch of the ratchet mechanism of FIG. 43 showing a tooth of the button for engaging the slider.

The lock latch 1462 further includes a projection, such as a tab portion 1490, extending from the handle portion 1484 that includes an end 1492. The lock latch surface 1494 abuts against surfaces of the frame 1302 when the lock latch 1462 is in the unlocked and locked positions, as discussed in greater detail below. With reference to FIGS. 47 and 48, the button 1450 includes a blind bore 1500 for receiving one end of a spring 1502. The other end of the spring 1502 is received in a recess 1504 of the frame 1302. With reference to FIG. 48, the spring biases the button 1450 in direction 1506 about the shaft 1458 and urges the tooth 1452 of the button 1450 into engagement with the depressions 1454 of the slider outer member 1342. As with the ratchet mechanisms described above, the movement of the slider in direction 1312 toward the retracted position thereof causes the tooth 1452 to ratchet over the teeth 1454A of the slider 1308 and permits the slider 1308 to retract. Conversely, the spring 1458 urges the tooth 1452 into engagement with the depressions 1454 and the contact between the tooth 1452 of the button 1450 and the tooth 1454A of the slider 1308 adjacent the depression 1454 resists movement of the slider 1308 in direction 1314 toward the extended position thereof.

Figure 47A:
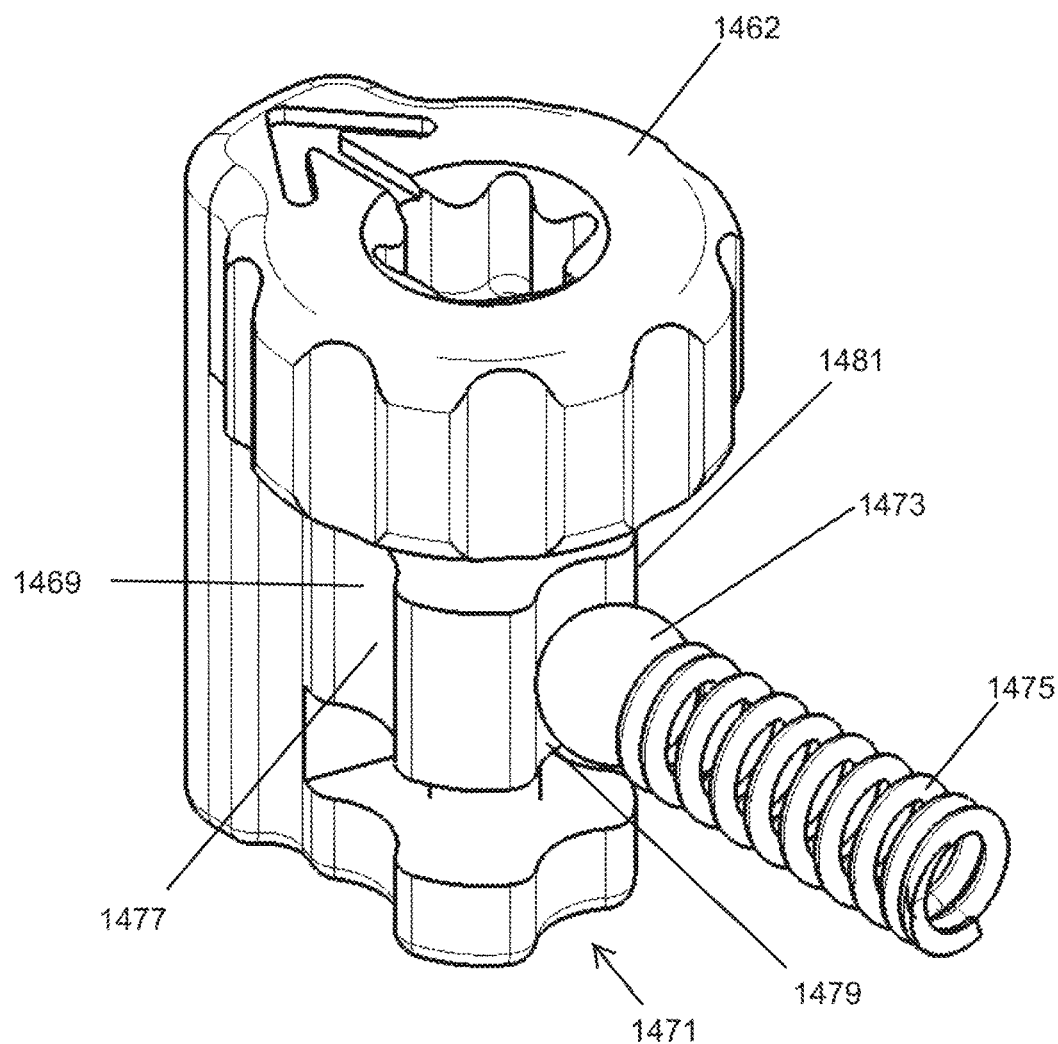
FIG. 47A is a perspective view of the lock latch of FIG. 47 and an internal detent mechanism of the button showing a ball of the detent mechanism engaging a recess of the lock latch to resist movement of the lock latch away from a selected orientation thereof.

Turning to FIG. 47A, the button 1450 includes a detent mechanism 1471 for holding the lock latch 1462 in the unlocked, ratchet, or locked positions thereof and resisting unintentional pivoting of the lock latch 1462 out of the selected position. The detent mechanism includes a ball 1473 and a spring 1475 received in a blind bore of the button 1450. The spring 1475 resiliently urges the ball 1473 partially outward from the blind bore and into engagement with an indexing surface 1469 of the lock latch 1462. The indexing surface 1469 includes grooves 1477, 1479, and 1481 that correspond, respectively, to the locked, ratchet, and unlocked positions of the lock latch 1462. For example, once the lock latch 1462 has been pivoted to the ratchet position thereof, the ball 1473 snaps into the groove 1479. To turn the lock latch 1462 to the locked position thereof, the surgeon applies sufficient force to overcome the biasing force from the spring 1475 and cam the ball 1473 out of the groove 1479. Once the lock latch 1462 reaches the locked position, the spring 1475 urges the ball 1473 into the groove 1477.

With reference to FIGS. 48 and 49, the operation of the lock latch 1462 will be discussed in greater detail. The frame 1302 includes a slot 1520 that receives the slider 1308. The slot 1520 is formed by a pair of spaced walls 1522, 1524 on opposite sides of the slider 1308 that guide the slider 1308 as the slider 1308 shifts in directions 1312, 1314. The wall 1522 has an opening 1525 in communication with the bore hole 1370 through which the teeth 1332 of the pinion 1330 extend and engage the teeth 1334 of the slider rack 1336. The other wall 1524 includes a through opening 1526 and the tooth 1452 extends therethrough to engage the depressions 1454 of the slider 1308. The frame 1302 includes a cavity 1530 near the wall 1524 with a flat floor surface 1532 and walls 1534 upstanding from the floor surface 1532 that are arranged in a generally U-shaped configuration. The lower end of the lock latch tab portion 1490 is received in the cavity 1530 and pivots therein with pivoting of the lock latch 1462 between the unlocked, ratchet, and locked positions thereof.

With reference to FIG. 49, the lock latch 1462 has been pivoted to the unlocked position with the orientation indicia 1470 of the lock latch 1462 aligned with unlocked indicia 1472 of the frame 1302. Pivoting the lock latch 1462 to the unlocked configuration brings the end 1492 of the lock latch 1462 into abutting contact with a surface 1540 of the walls 1534 of the cavity 1530 and pivots the button 1450 in direction 1560. This causes the button 1450 to compress the spring 1502 and hold the tooth 1452 out of engagement with the depressions 1454 of the slider 1308. Further, the lock latch 1462 resists pivoting of the button 1450 in direction 1506 about the shaft 1458 and continues to cause the button 1450 to hold the tooth 1452 out of engagement with the depressions 1454 until the lock latch 1462 is pivoted away from the unlocked position. Thus, with the lock latch 1462 in the unlocked position, the surgeon can shift the slider 1308 in direction 1312 or 1314 as desired without the tooth 1452 resisting movement of the slider 1308.

With reference to FIGS. 50 and 51, the lock latch 1462 has been pivoted to the ratchet position thereof such that the orientation indicia 1470 of the lock latch 1462 is aligned with the ratchet indicia 1474 of the frame 1302. Because the end 1492 of the lock latch 1462 no longer abuts the cavity surface 1540, the spring 1502 can pivot the button 1450 in direction 1506 about the shaft 1458 and cause the tooth 1452 to engage the depressions 1454 of the slider outer member 1342. The engaged tooth 1452 and depressions 1454 are configured to permit the slider 1308 to slide in direction 1312. When the slider 1308 slides in direction 1312, the tooth 1452 received in one depression 1454 cams over and past the adjacent tooth 1454A, ratchets into the next depression 1454, cams over and past the next tooth 1454A, ratchets into the next depression 1454, cams over the next tooth 1454A, etc. However, the tooth 1452 can abut flat surfaces 1454B of the teeth 1454A and resist movement of the slider 1308 in direction 1314.

To move the slider 1308 in direction 1314 when the lock latch 1462 is in the ratchet position, the surgeon presses on a side 1511 (see FIG. 51) of the button 1450 and pivots the button 1450 in direction 1560. This compresses the spring 1502 and withdraws the tooth 1452 out of engagement with the depressions 1454. With the tooth 1452 disengaged from the depressions 1454, the slider 1308 may be slid in direction 1314 toward the extended position thereof.

With the lock latch 1462 in the ratchet position of FIGS. 50 and 51, the lock latch 1462 can move back-and-forth within the cavity 1530 in directions 1560, 1506 with the button 1450. Specifically, the lock latch 1462 pivots in direction 1560 as the button 1450 pivots in direction 1560 about the shaft 1458 due to the tooth 1452 being cammed out of the way by the inclined surface of one of the teeth 1454A as the slider 1308 shifts in direction 1312. For example, a surgeon may insert a hexalobular driver into the socket 1348 of the drive cap 1346 and turn the drive cap 1346 and pinion 1330 in drive direction 1350. This causes the slider 1308 to shift in direction 1312 toward the retracted position thereof and the inclined surface of the one tooth 1454A cams the tooth 1452 outward and out of engagement with the depression 1454. This camming action causes the button 1450 to pivot in direction 1560 and the lock latch 1462 likewise pivots with the button 1450 in direction 1560 within the cavity 1530.

Once the tooth 1452 has been cammed out of the way of the one tooth 1454A, the button 1450 can pivot back in direction 1506 and advance the tooth 1452 into engagement with the next depression 1454 as the slider 1308 slides in direction 1312. The lock latch 1462 likewise pivots with the button 1450 in direction 1506 within the cavity 1530. Thus, the lock latch 1462 moves back-and-forth in directions 1560, 1506 as the slider 1308 is shifted in direction 1312 and the tooth 1452 ratchets in and out of engagement with the depressions 1454. The cavity 1530 provides clearance for this back-and-forth movement of the lock latch 1462.

Upon the slider 1308 reaching the desired retracted position, the surgeon may pivot the lock latch 1462 to the locked orientation shown in FIGS. 52 and 53. With the lock latch 1462 pivoted to the locked orientation, the orientation indicia 1470 of the lock latch 1462 is aligned with the lock indicia 1476 of the frame 1302 and the end 1492 of the lock latch tab portion 1490 abuts a surface 1570 of the wall 1524. Due to the lock latch end 1492 abutting the wall surface 1570, the tab portion 1490 rigidly resists pivoting of the button 1450 in direction 1560 which would disengage the tooth 1452 from the depressions 1454. Thus, with the lock latch 1462 in the locked position, the lock latch 1462 maintains the tooth 1452 engaged with one of the depressions 1454 of the slider outer member 1342. The lock latch 1462 thereby resists contact against the button 1450 causing the button 1450 to withdraw the tooth 1452 from the depression 1454 and permitting the slider 1308 to shift in direction 1314 toward its extended position. Thus, even if the surgeon were to press against the side 1511 and attempt to pivot the button 1450 in direction 1560, the lock latch 1462 would rigidly resist the pivoting of the button 1450 and would thereby keep the tooth 1452 engaged with one of the depressions 1454.

When the surgeon wants to shift the slider 1308 in direction 1314, the surgeon simply pivots the lock latch 1462 back to the ratchet orientation (see FIG. 51) and presses against the side 1511 of the button 1450 to disengage the tooth 1452 from the depression 1454. Alternatively, the surgeon may pivot the lock latch 1462 to the unlocked orientation (see FIG. 49) which automatically pivots the button 1450 in direction 1560 and withdraws the tooth 1452 from the depression 1454.

With reference to FIGS. 54 and 55, the inner member 1340 is pivotally connected to the outer member 1342 at the pivot pin 1600. The slider 1308 includes an elevation screw 1602 having a threaded shank 1604 engaged with a threaded recess 1606 of the inner member 1340. The elevation screw 1602 has a distal ball 1608 that is received in a socket 1610 of the outer member 1342. The socket 1610 holds the ball 1608 and permits pivoting of the ball 1608 relative to the outer member 1342. As the elevation screw 1602 is turned, the engagement between the elevation screw 1602 and the inner member 1340 pivots the inner member 1340 about the pivot pin 1600 to an inclined orientation as shown in FIG. 55. The pocket 1610 may be elongated along the slider outer member 1342 and include a pocket surface 1620 engaged with the ball 1608 that permits the ball 1608 to shift in directions 1622 as the inner member 1340 pivots relative to the outer member 1342.

The slider 1308 also includes a wedge lock 1630 for releasably securing a blade within a dovetail recess 1632 of the inner member 1340. The wedge lock 1630 includes a wedge member 1634 pivotally mounted on a pin 1636 within a recess 1640 of the inner member 1340. The wedge lock 1630 further includes a fixation screw 1642 having a head 1644 for receiving an adjustment tool and a shank 1646 threadingly engaged with a nut 1648. The nut 1648 is connected to the wedge 1348 and configured to transfer vertical movement of the nut 1648 along the shank 1646 into pivoting of the wedge 1634. For example, the nut 1648 may have a pair of pins extending outward therefrom that are received in elongated slots of the wedge member 1634. The slots of the wedge member 1634 are configured to cammingly engage the pins of the nut 1648 and transfer linear movement of the nut 1648 into pivoting of the wedge member 1634.

To secure a blade within the dovetail recess 1632 of the inner member 1340, a surgeon may rotate the fixation screw 1642 in a clockwise direction (when viewed from above) and cause the fixation screw 1642 to draw the nut 1648 upward in direction 1650 and pivots the wedge member 1634 in direction 1652. Pivoting the wedge member 1634 in direction 1652 causes an outer surface 1654 of the wedge member 1634 to press against the blade and lock the blade within the dovetail recess 1632. Conversely, the surgeon may rotate the fixation screw 1642 in a counter-clockwise direction (when viewed from above) and cause the nut 1648 to travel downwardly in direction 1660 and pivot the wedge member 1634 in direction 1662 to disengage the wedge member outer surface 1654 from the blade.

The slide 1308 also includes a beyond center locking mechanism 1670 including a lock button 1672 having a lower end 1674 for interfering with the retractor frame 1302 and limiting movement of the slider 1308 in direction 1314 to a predetermined extended position. The beyond center locking mechanism 1670 further includes a pin 1676 received in a recess 1678 of the slider outer member 1342 to connect the lock button 1672 to the outer member 1342. The recess 1678 is elongated and permits the surgeon to shift the lock button 1672 in direction 1680 to raise the button lower end 1674 out of interference with the frame 1302 and permit the slider 1308 to shift further in direction 1314 toward a beyond center position thereof.

The components of the retractor 1300 may be made from a variety of materials. As but some examples in this regard, the frame 1302 may be made from a metallic or plastic material, such as aluminum or carbon fiber. The material of the frame 1302 may be selected such that the frame 1302 is radiolucent. The slider 1308 may be made from a metallic material, such as stainless steel, aluminum, or titanium. The button tooth 1452 may be made from a metallic material such as stainless steel. The lock latch 1462 may be made from a plastic material, such as an instrument grade polyaryletherketone.

Figure 56:
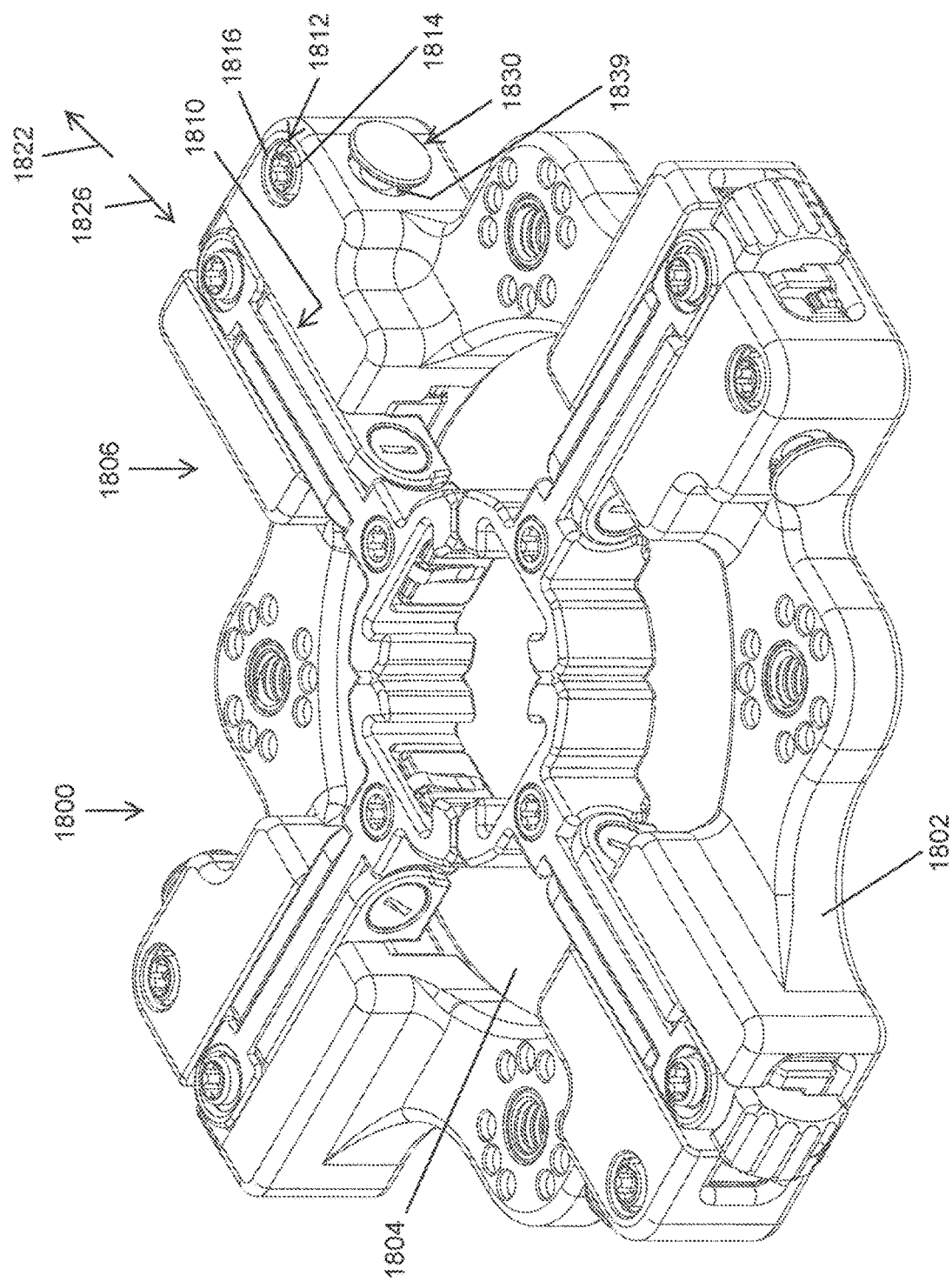
FIG. 56 is a perspective view of a retractor having operating mechanisms that receive tissue engaging members and permit retraction of the tissue engaging members to retract tissues.

With reference to FIG. 56, a retractor 1800 is provided that is similar in many respects to the retractors 600, 1010, 1210, 1300 discussed above. The retractor 1800 includes a frame 1802 extending about a central opening 1804 and having one or more operating mechanisms 1806 that connect tissue engaging members such as retractor blades 1214 to the frame 1802. Each operating mechanism 1806 includes a slider 1810 and a slider linear drive 1812 for shifting the slider 1810 between extended and retracted positions relative to the frame 1802. The slider linear drive 1812 includes a tool-receiving member, such as a worm screw 1814, disposed in a bore hole 1816 of the frame 1802. Regarding FIG. 57, turning the worm screw 1814 in a clockwise direction 1820 causes the slider 1810 to retract in direction 1822. Conversely, turning the worm screw 1814 in a counterclockwise direction 1824 causes the slider 1810 to shift in direction 1826.

Figure 57:
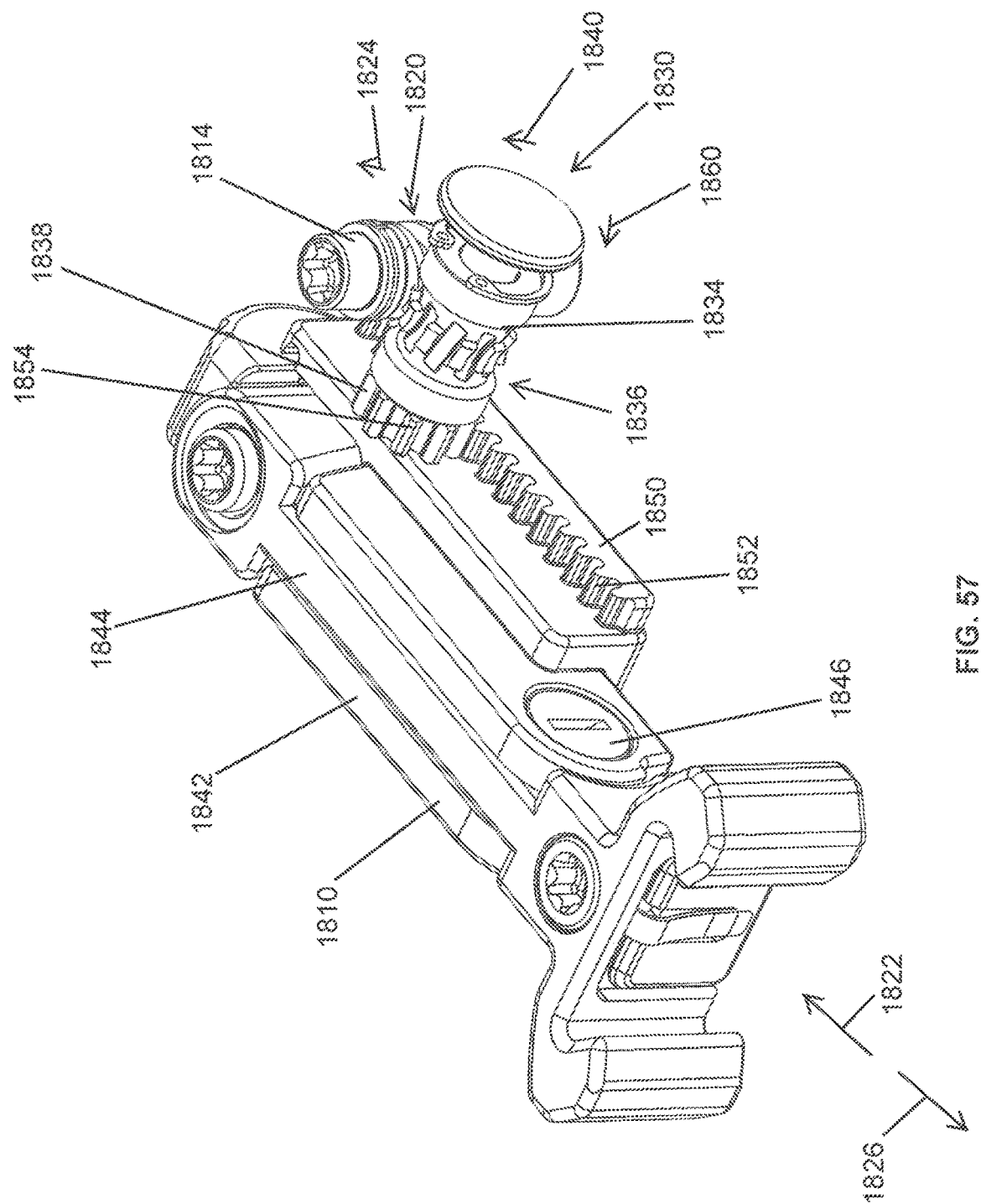
FIG. 57 is a perspective view of a slider and a slider linear drive of one of the operating mechanisms of FIG. 56.

With reference to FIG. 57, the worm screw 1814 is engaged with a worm gear 1834 of a worm gear assembly 1836. The worm gear assembly 1836 includes a rotatable drive member, such as a pinion gear 1838, that is selectively coupled to the worm gear 1834. The worm gear 1834 has a helical tooth 1874 (see FIG. 58) that engages teeth 1870 of the worm gear 1834 (see FIG. 59). The worm screw 1814 and the worm gear 1834 are configured to be self-locking to inhibit unintended rotation of the worm gear 1834 and pinion gear 1838 coupled thereto which locks the slider 1810 in position relative to the frame 1802 when the surgeon is not turning the worm screw 1814.

Further, the engagement between the helical tooth 1874 and teeth 1870 permits positioning of the slider 1810 that is not limited by increments defined by a ratchet mechanism. The continuous helical tooth 1874 of the worm screw 1814 is always engaged with at least one of the teeth 1870 of the worm gear 1834 and operates as an inclined plane to drive the at least one tooth 1870 the distance imparted by turning of the worm screw 1814. In other words, the engagement between the helical tooth 1874 and teeth 1870 permits infinitely adjustable positioning of the slider 1810 and tissue engaging member. A user can thereby turn the worm screw 1814 to cause as large or as small of a change in position of the slider 1810 as desired. Because the slider 1810 is not limited to shifting in increments dictated by a ratchet mechanism, the retractor 1800 provides enhanced flexibility in positioning the sliders 1810 with respect to the anatomy of a patient.

With reference to FIG. 57, each operating mechanism 1806 includes a clutch 1830 having a release mode wherein the clutch 1830 decouples the worm gear 1834 from the pinion gear 1838. The clutch 1830 is similar to the clutch discussed above that includes the cam surface 1418 of the pinion 1330 and the cam surface 1434 of the drive cap 1346. Turning the drive cap 1346 in reverse direction 1351 reconfigures the clutch to a release mode, causes the surfaces 1418, 1434 to cammingly engage, and shifts the pinion 1330 away from the drive cap 1346. The drive cap 1346 can thereby turn in reverse direction 1351 relative to the pinion 1330. Likewise, when the clutch 1830 is in the release mode, the pinion gear 1838 can turn relative to the worm gear 1834 which permits the slider 1810 to be shifted by a user in direction 1822 or direction 1826 without resistance from the meshed worm screw 1814 and worm gear 1834. The clutch 1830 also includes a drive mode wherein the clutch 1830 couples the worm gear 1834 and the pinion gear 1838. With the clutch 1830 in the drive mode, turning of the worm screw 1814 in directions 1820, 1824 causes turning of the worm gear 1834 and pinion 1838 coupled therewith and associated shifting of the slider 1810 in directions 1822, 1826.

Regarding FIG. 57, the slider 1810 has a base, such as outer member 1842, and an arm, such as inner member 1844, pivotally coupled to the outer member 1842 by a pivot pin 1846. The outer member 1842 includes a rack 1850 having teeth 1852 that are meshed with teeth 1854 of the pinion gear 1838. Thus, when the clutch 1830 is in the drive mode, rotating the worm screw 1818 in direction 1820 causes rotation of the pinion gear 1838 in direction 1840 which shifts the slider outer member 1842 in direction 1822. Conversely, turning the worm screw 1818 in direction 1824 causes rotation of the pinion gear 1838 in direction 1860 which shifts the slider outer member 1842 in direction 1826. Thus, the worm screw 1814 is turned to shift the slider 1810 in either the retracting direction 1822 or the release direction 1826.

Figure 58:
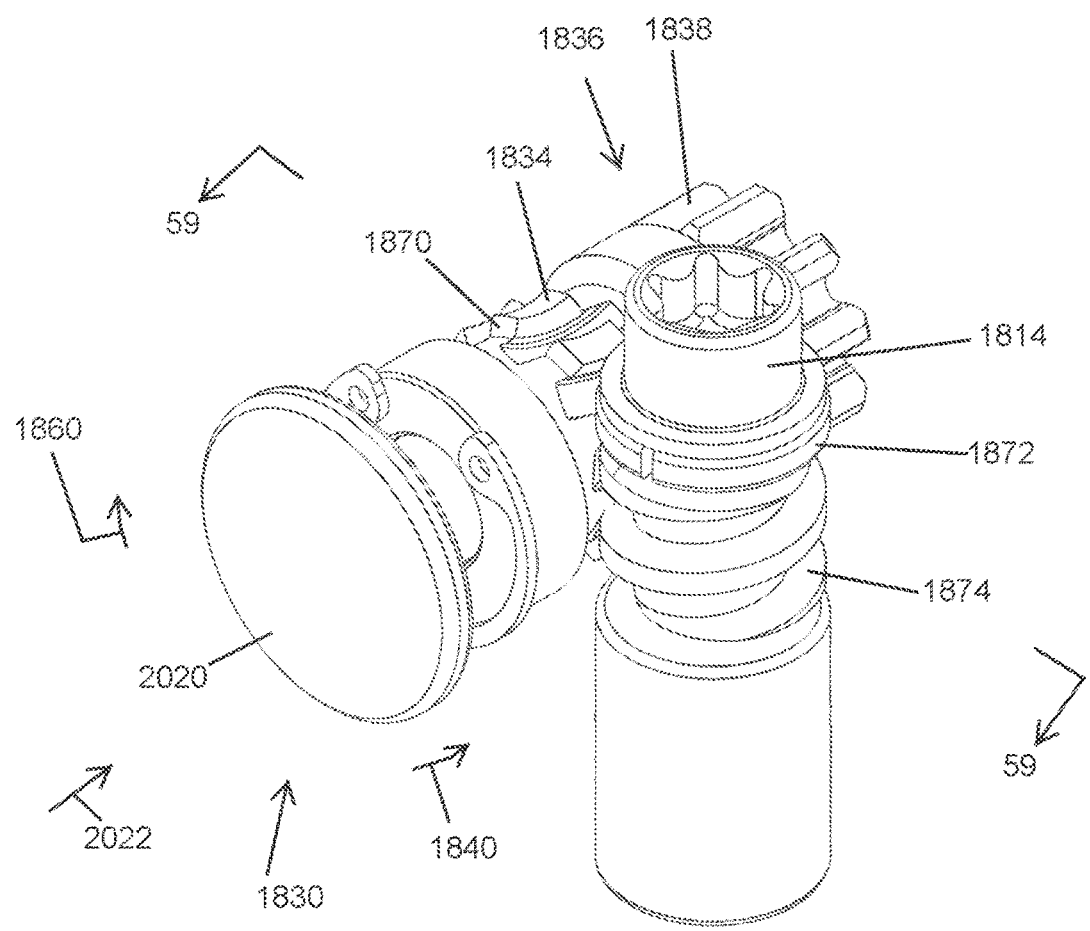
FIG. 58 is a perspective view of a worm screw and a worm gear assembly of the linear drive mechanism of FIG. 57.
Figure 59:
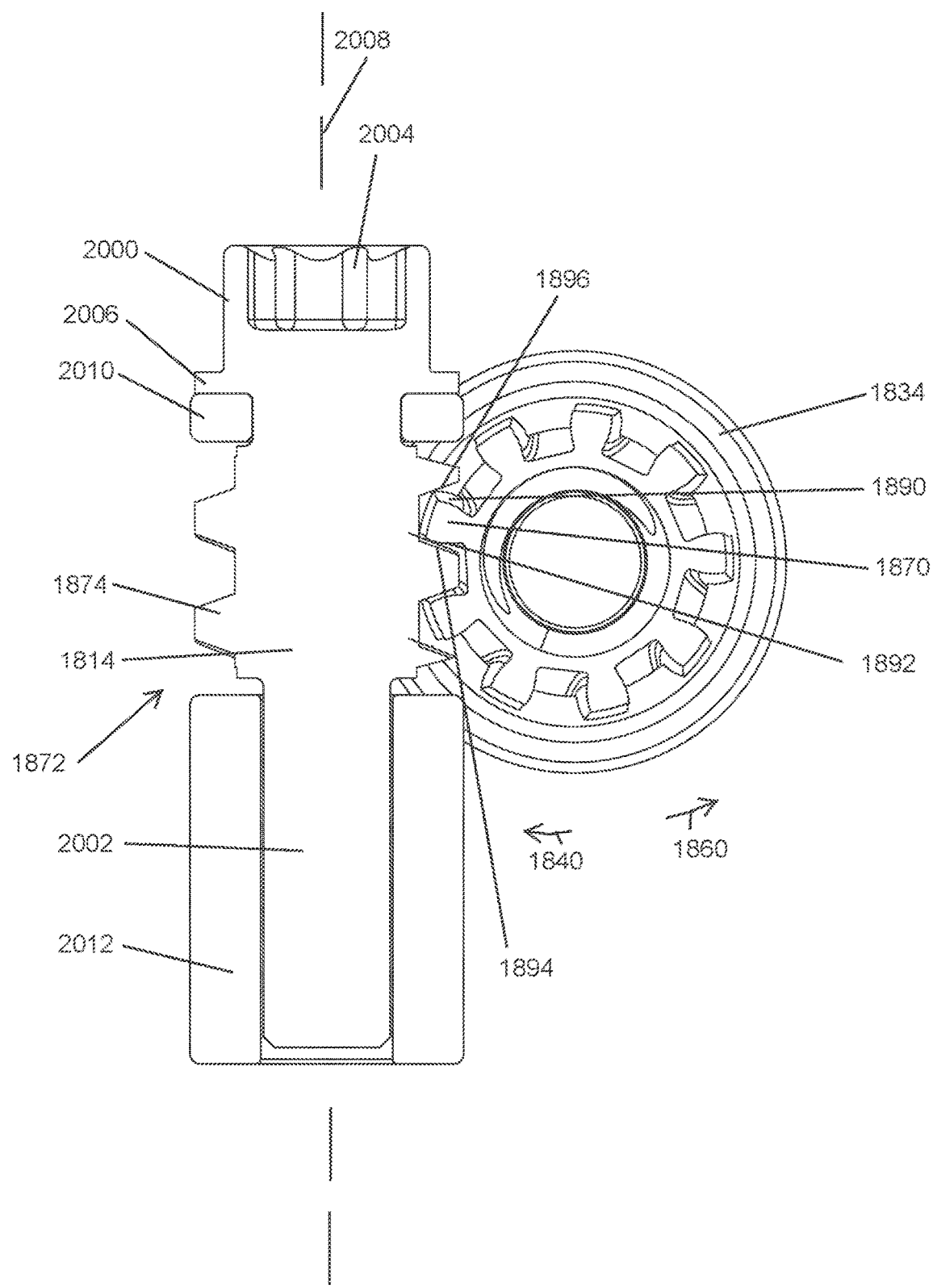
FIG. 59 is a cross-sectional view taken across line 59-59 in FIG. 58 showing a helical tooth of the worm screw engaged with teeth of the worm gear assembly.

With reference to FIGS. 58 and 59, the teeth 1870 of the worm gear 1834 and the helical tooth 1874 of the worm screw 1814 are configured to be self-locking. In other words, the frictional engagement between one or more of the teeth 1870 and the helical tooth 1874 is sufficiently high to resist turning of the worm gear 1834 due to force imparted on a tissue engagement member supported by the slider 1810. Thus, once the user has driven the worm screw 1814 to position the slider 1810 in the desired position, the slider 1810 is locked in position and cannot shift in either direction 1822, 1826 until the surgeon decides to again drive the worm screw 1814 in direction 1820 or 1824 or reconfigures the clutch 1830 from the drive mode to the release mode.

With reference to FIG. 59, the teeth 1870 have each have a thread profile with a generally involute gear shape and the helical tooth 1874 has a trapezoidal thread profile. The self-locking operation of the worm screw 1814 and the worm gear 1834 are provided at least in part by surfaces 1890, 1892 of each of the teeth 1870 and surfaces 1894, 1896 of the helical tooth 1874. For example, once the slider 1810 has been retracted to a desired position, the retracted tissue may urge the slider 1810 in direction 1826 (see FIG. 57). This urges the tooth 1870 in direction 1860 (see FIG. 59) and presses the surface 1892 of the worm gear tooth 1870 against the upper surface 1894 of the helical tooth 1874. The engagement between the surfaces 1892, 1894 resists turning of the worm gear 1834 in direction 1860. Because the worm gear 1834 does not turn in direction 1860, and the clutch 1830 is in the drive mode, the pinion gear 1838 does not turn in direction 1860 and the slider 1810 does not shift in direction 1826 despite the loading from the retracted tissue.

As another example, once the slider 1810 has been retracted to a desired position, if an instrument contacts the tissue engaging member and urges the slider 1810 in direction 1822, the pinion 1838 will be urged in direction 1840 which would bring the surface 1890 (see FIG. 59) into engagement with the surface 1896 of the helical tooth 1874. The engagement between the surfaces 1890, 1896 inhibits turning of the worm gear 1834 in direction 1840. Because the worm gear 1834 does not turn in direction 1840, and the clutch 1830 is in drive mode, the pinion gear 1838 does not turn in direction 1840 and the slider 1810 does not shift in direction 1822 despite the contact with the instrument.

Regarding FIG. 59, the worm screw 1814 includes a worm portion 1872 including the helical tooth 1874, a head 2000, and a shank 2002. The head 2000 includes a tool-engaging portion, such as a socket 2004, configured to receive a hexalobular driver to turn the worm screw 1814. The worm screw 1814 is captured in the bore hole 1816 (see FIG. 56) of the frame 1802 by a c-ring positioned above a flange 2006 of the worm screw 1814 The worm screw 1814 is rotatable about an axis 2008 and is subjected to loading parallel and transverse to the axis 2008 due to engagement with the worm gear 1834. In one embodiment, thrust bearings 2010, 2012 support the worm screw 1814 in the bore hole 1816 and permit the worm screw 1814 to turn with limited resistance from the frame 1802.

With reference to FIGS. 56 and 58, the clutch 1830 is operable to disengage the pinion gear 1838 from the worm gear 1834. In one embodiment, the clutch 1830 is a component of the worm gear assembly 1836 and turns with turning of the worm screw 1814. More specifically, the clutch 1830 includes a button 2020 that is pressed in direction 2022 to decouple the worm gear 1834 from the pinion gear 1838 and reconfigure the clutch 1830 from the drive mode to the release mode. When the clutch 1830 is in the release mode, the pinion gear 1838 may turn relative to the worm gear 1834. Because the pinion gear 1838 may turn relative to the worm gear 1834, the slider 1810 may be shifted in directions 1826, 1822 to a desired position without resistance from the intermeshed worm gear 1834 and the worm screw 1814. The surgeon may shift the slider 1810 by hand in directions 1826, 1822 or by utilizing an instrument when the clutch 1830 is in the release mode.

Figure 60:
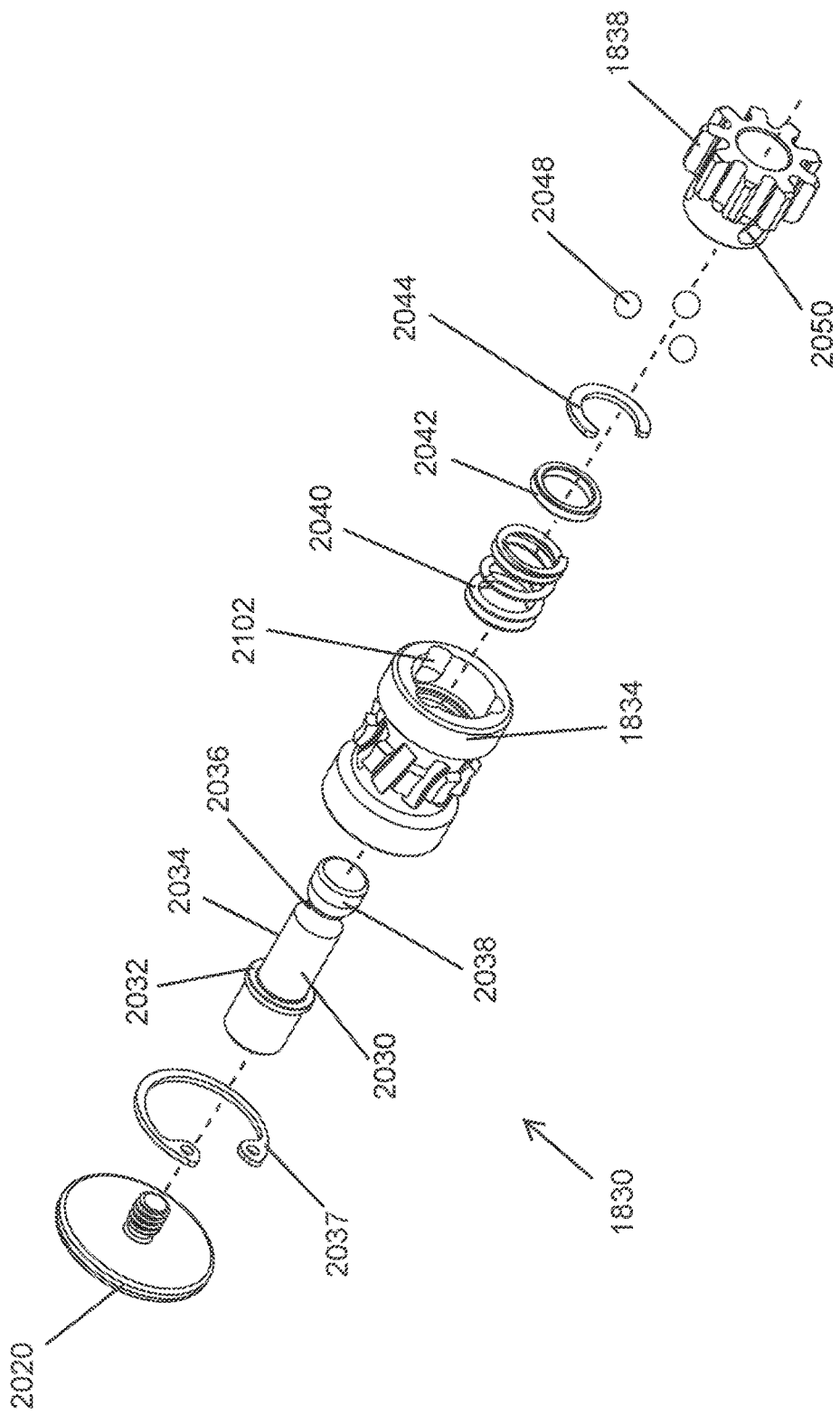
FIG. 60 is an exploded, perspective view of the worm gear assembly of FIG. 58 showing ball bearings that are radially shiftable to couple and decouple a worm gear and a pinion gear of the worm gear assembly.

With reference to FIG. 60, the clutch 1830 includes a release shaft 2030 to which the button 2020 is mounted, such as via a threaded connection therebetween. The release shaft 2030 has a collar 2032, a cylindrical portion 2034, a neck portion 2036, and a head portion 2038. The clutch 1830 includes a spring 2040, a spring seat washer 2042, and a retaining ring 2044. The head 2038 of the release shaft 2030 engages at least one coupling member, such as ball bearings 2048. The ball bearings 2048 are received in openings 2050 of the pinion gear 1838 and may extend into pockets 2102 of the worm gear 1834.

The ball bearings 2048 are shiftable radially between a radially outward position wherein the ball bearings 2048 extend into the worm gear pockets 2102 and couple the pinion 1838 to the worm gear 1834 and a radially inward position where the ball bearings 2048 are spaced from the worm gear 2034 and decouple the pinion gear 1838 from the worm gear 1834. To reconfigure the clutch 1830 from the drive mode to the release mode, the user presses the button 2020 in direction 2022 (see FIG. 61B) which shifts the release shaft 2030 in direction 2022 to position the neck portion 2036 in alignment with the ball bearings 2048 thereby permitting the ball bearings 2048 to shift radially inward as discussed in greater detail below. A snap ring 2037 (see FIG. 60) may be provided to capture the worm gear assembly 1836 within a bore hole 1839 (see FIG. 56) of the frame 1802.

Figure 61A:
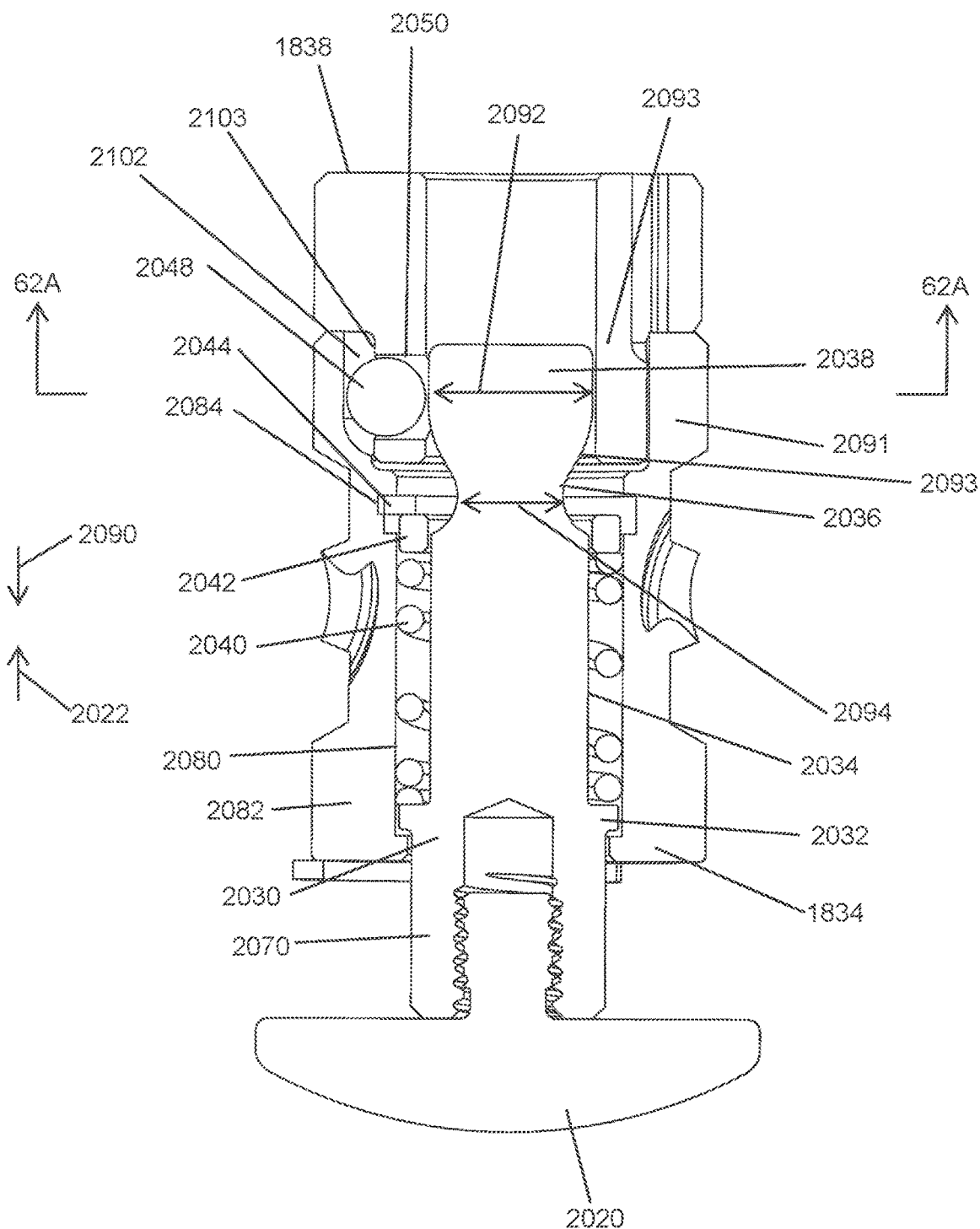
FIG. 61A is a cross-sectional view of the worm gear assembly of FIG. 60 in an assembled configuration, FIG. 61A showing a release shaft of the worm gear assembly in a drive position wherein a head portion of the release shaft keeps the ball bearings shifted radially outward and couples the worm gear and the pinion gear.

With reference to FIG. 61A, the release shaft 2030 is shown in a drive position thereof. The worm gear 1834 includes a bore 2080 that receives the cylindrical portion 2034 of the release shaft 2030 and the spring 2040 extending thereabout. The worm gear 1834 includes a wall 2082 extending about the bore 2080 that includes a groove 2084 which receives the retaining ring 2044. The spring 2040 is captured between the collar 2032 of the release shaft 2030 and the spring seat washer 2042. Thus, pressing the button 2020 in direction 2022 shifts the release shaft 2030 in direction 2022 and brings the collar 2032 closer to the spring seat washer 2042 which compresses the spring 2040. The button 2020 is pressed to shift the release shaft 2030 in direction 2022 until the release shaft 2030 reaches a release position thereof which radially aligns the neck portion 2036 of the release shaft 2030 with the ball bearings 2048. The neck portion 2036 permits the ball bearings 2048 to shift radially inward which decouples the worm gear 1834 from the pinion gear 1838. When the user releases the button 2020, the spring 2040 urges the release shaft 2030 back in direction 2090 to the drive position thereof wherein the head portion 2038 of the release shaft 2030 is radially aligned with the ball bearings 2048. The spring 2040 thereby automatically returns the clutch 1830 to the drive mode once the user releases the button 2020.

Regarding FIGS. 60 and 61A, the worm gear 1834 includes a sleeve portion 2091 extending about an annular wall 2093 of the pinion 1834. The annular wall 2093 has the through openings 2050 extending therethrough. The sleeve portion 2091 of the worm gear 1834 has pockets 2102 spaced thereabout. The pockets 2102 include openings 2103 sized to permit a portion of the ball bearings 2048 to extend into the pockets 2102.

Figure 62A:
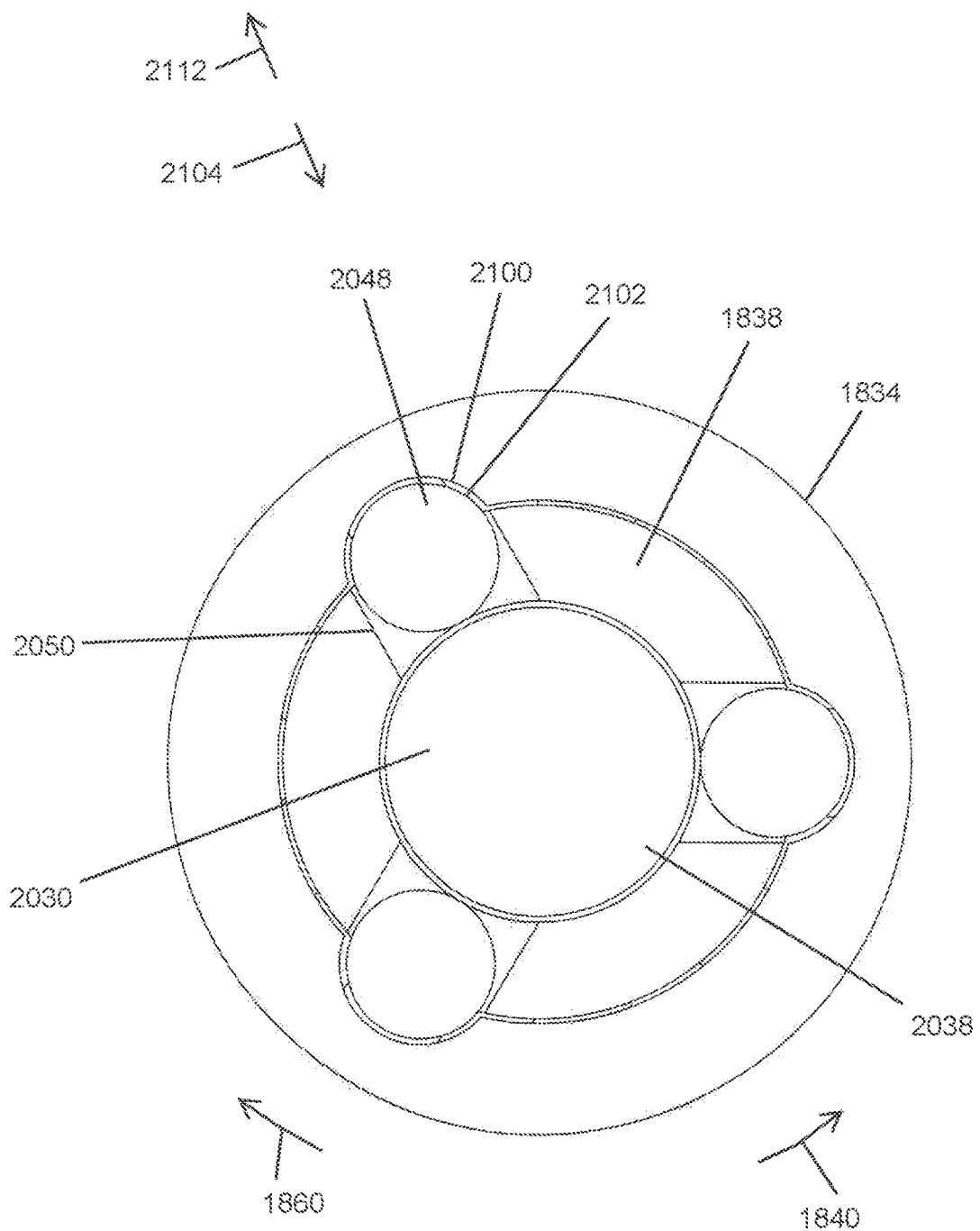
FIG. 62A is a cross-sectional view taken across line 62A-62A in FIG. 61A showing the release shaft in the drive position and the ball bearings extending in through openings of the pinion gear and into pockets of the worm gear.

With reference to FIGS. 61A and 62A, the release shaft 2030 is shown in the drive position and the head portion 2038 radially aligned with the ball bearings 2048. The head portion 2038 of the release shaft 2030 has a diameter 2092 that is larger than a diameter 2094 of the neck portion 2036. The larger diameter 2092 of the head portion 2038 keeps the ball bearings 2048 extending into the pockets 2102 of the worm gear 1834 and inhibits the ball bearings 2048 from shifting radially inward. When the smaller diameter 2094 of the neck portion 2036 is aligned with the ball bearings 2048, the clearance between the neck portion 2036 and the ball bearings 2048 permits the ball bearings 2048 to shift radially inward and out of the pockets 2102 of the worm gear 1834.

Figure 61B:
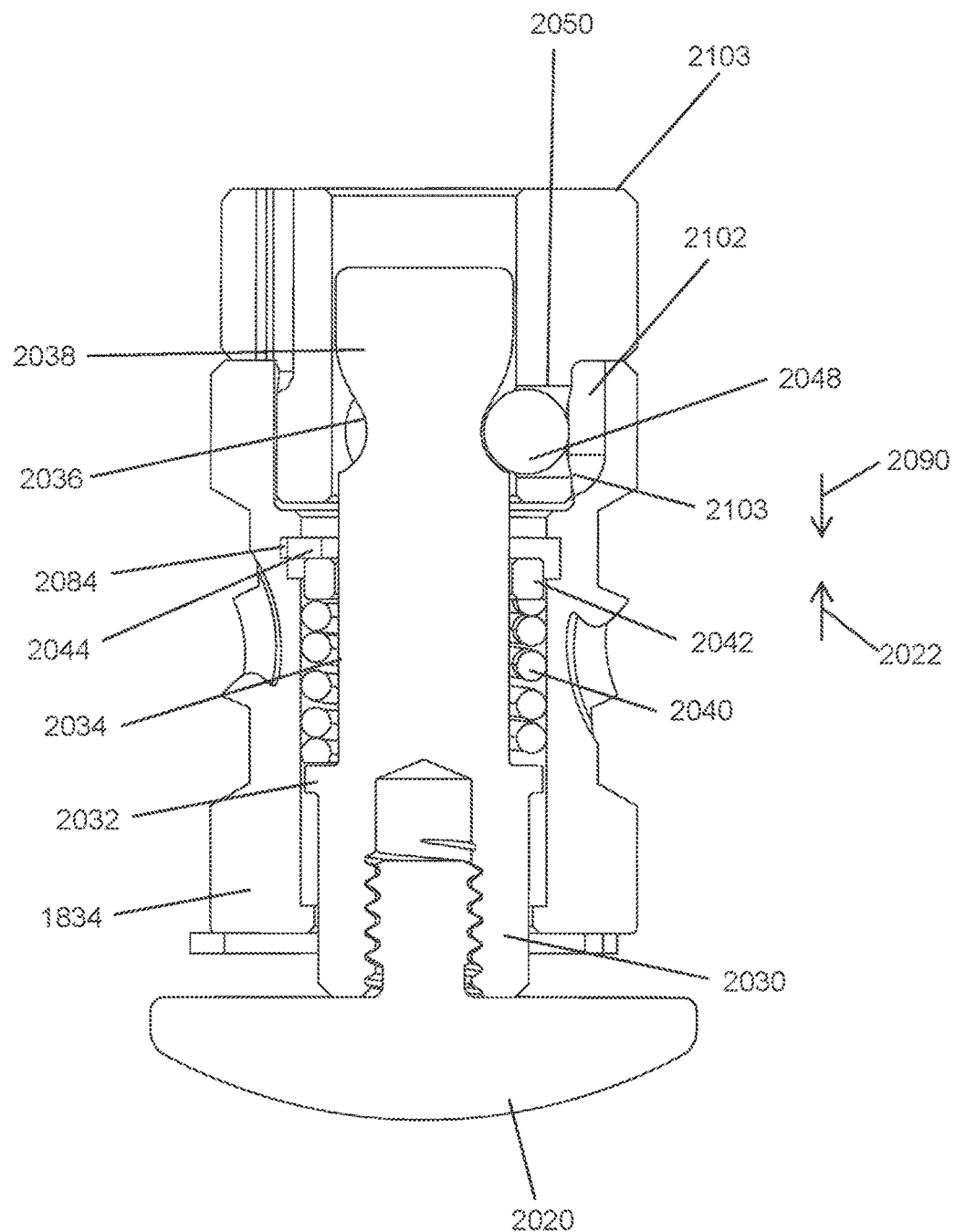
FIG. 61B is a cross-sectional view similar to FIG. 61A showing the release shaft in a release position wherein a neck portion of the release shaft permits the ball bearings to shift radially inward and decouple the worm gear and the pinion gear.
Figure 62B:
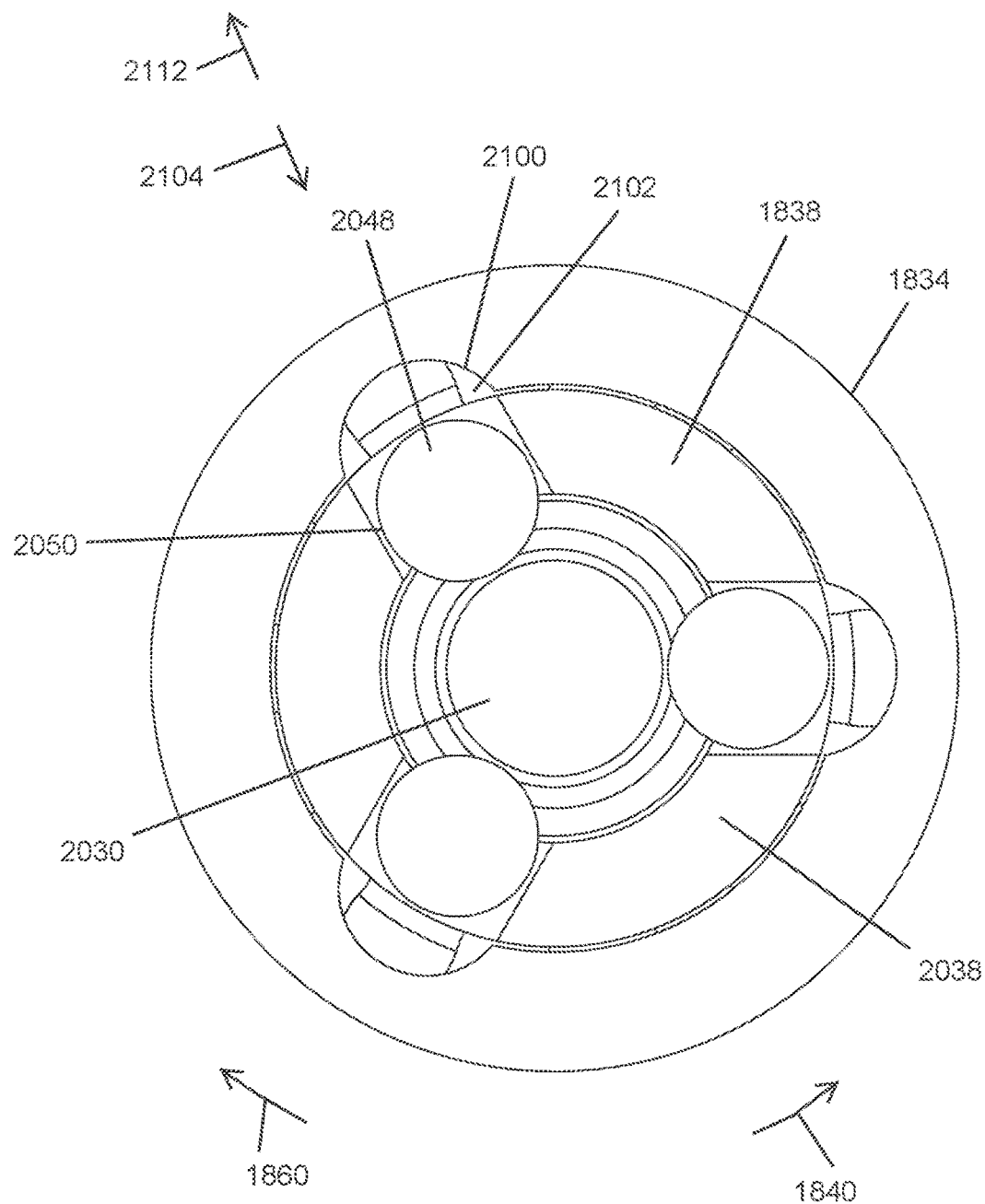
FIG. 62B is a cross-sectional view similar to FIG. 61A showing the release shaft in the release position and the ball bearings shifted out of the pockets of the worm gear.

With reference to FIGS. 61B and 62B, the release shaft 2030 is shown in the release position and the neck portion 2036 is radially aligned with the ball bearings 2048. When the pinion 1838 is urged in one of the directions 1840, 1860, such as by a user manually shifting the slider 1810 in direction 1822 or direction 1826, the pinion gear 1838 will turn and curved surfaces 2100 of the worm gear pockets 2102 cam the ball bearings 2048 radially inward in direction 2104.

Once the surgeon has moved the slider 1810 to the desired position and has released the button 2020, the spring 2040 urges the release shaft 2030 in direction 2090 to bring the head portion 2038 of the release shaft 2030 into the release position. With reference to FIG. 61A, the release shaft 2030 has a cam surface 2093 that is configured to engage and shift the ball bearings 2048 radially outward in direction 2112 as the spring 2040 returns the release shaft 2030 to the drive position thereof. Once the release shaft 2030 is in the drive position, the head portion 2038 keeps the ball bearings 2048 from shifting radially inward in direction 2104.

As shown in FIG. 62A, the ball bearings 2048 extend in the pockets 2102 of the worm gear 1834 and the through openings 2050 of the pinion 1838. The ball bearings 2048 are therefore subjected to shearing forces from the worm gear 1834 and the pinion gear 1838 as the ball bearings 2048 lock the worm gear 1834 and pinion gear 1838 together. The ball bearings 2048 may be made of a metallic material, such as stainless steel, to resist the sheer loading applied to the ball bearings 2048. The worm screw 1814, worm gear 1834, pinion gear 1838, spring 2040, and release shaft 2030 may also be made of one or more metallic materials, such as stainless steel, and/or high-strength plastic materials.

Figure 63:
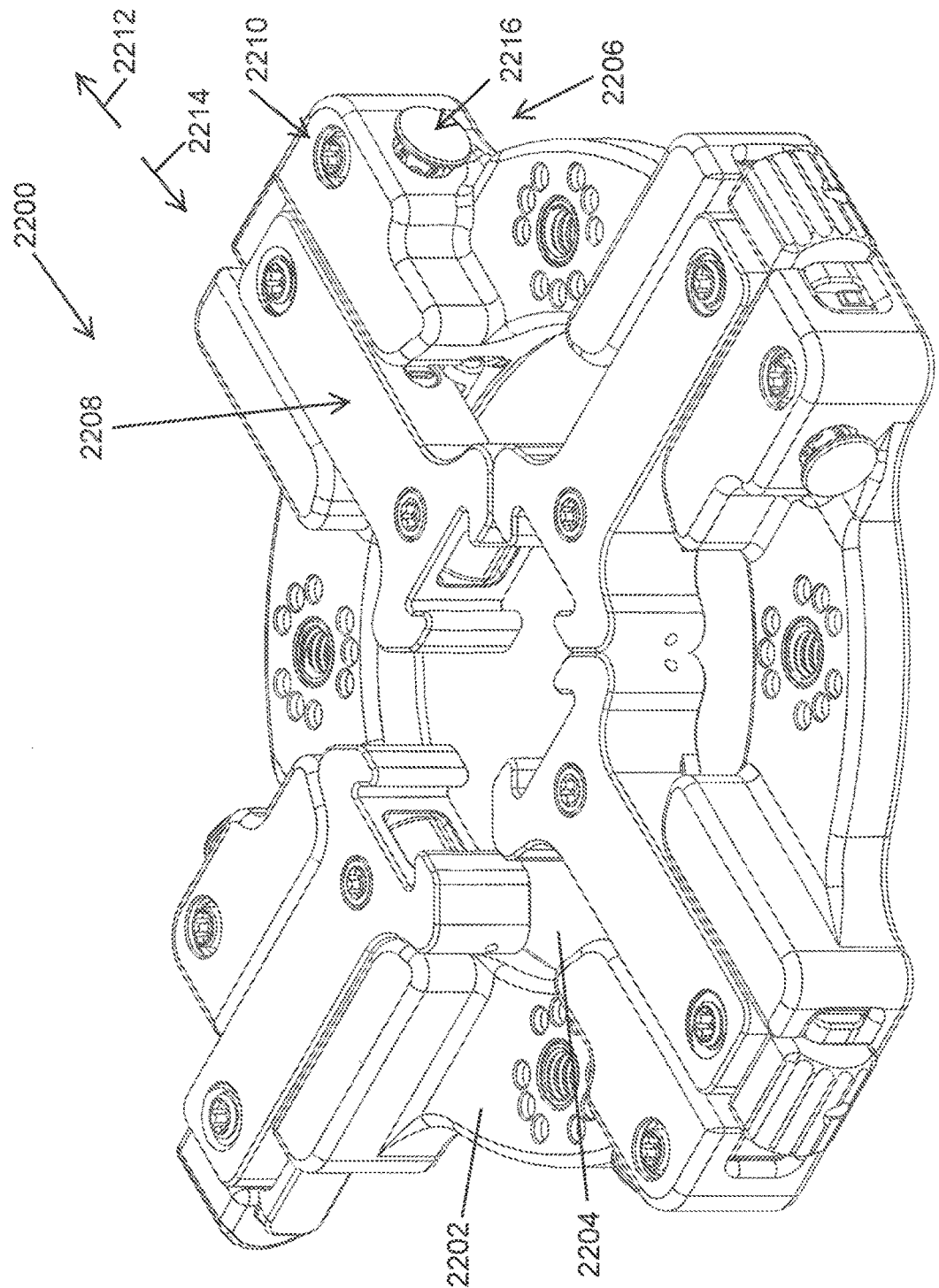
FIG. 63 is a perspective view of a retractor having operating mechanisms that support tissue engaging members and permit a user to retract the tissue engaging members and retract tissues of a patient.

With reference to FIG. 63, a retractor 2200 is provided that is similar in many respects to the retractors discussed above. The retractor 2200 includes a frame 2202 extending about a central opening 2204 and having operating mechanisms 2206 for connecting tissue engaging members to the frame 2202. The operating mechanisms 2206 each include a slider 2208 and a slider linear drive 2210 for shifting the slider 2208 in directions 2212, 2214. The retractor 2200 also includes a clutch 2216 associated with the slider linear drive 2210. The slider linear drive 2210 and the clutch 2216 are similar to the slider linear drive 1812 and clutch 1830 discussed above.

Figure 64:
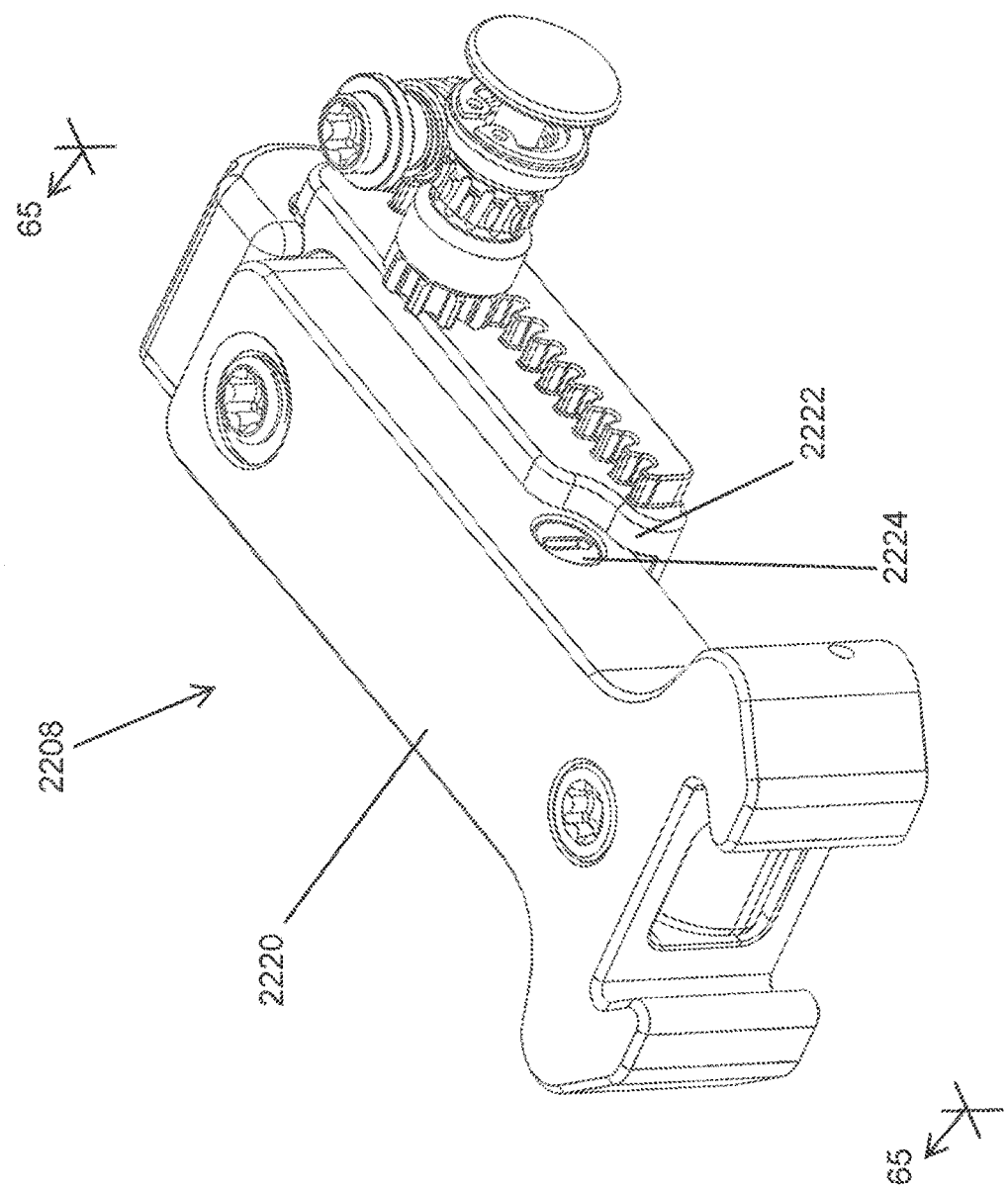
FIG. 64 is a perspective view of a slider and a slider linear drive of one of the operating mechanisms of the retractor of FIG. 63.

Regarding FIG. 64, the sliders 2208 may be made of a carbon fiber material which is radiolucent and provides less obstructed x-ray imaging of a surgical site during a surgical procedure. Each slider 2208 includes an arm, such as an inner member 2220, and a base, such as an outer member 2222, that are pivotally connected by a pivot pin 2224.

Figure 65:
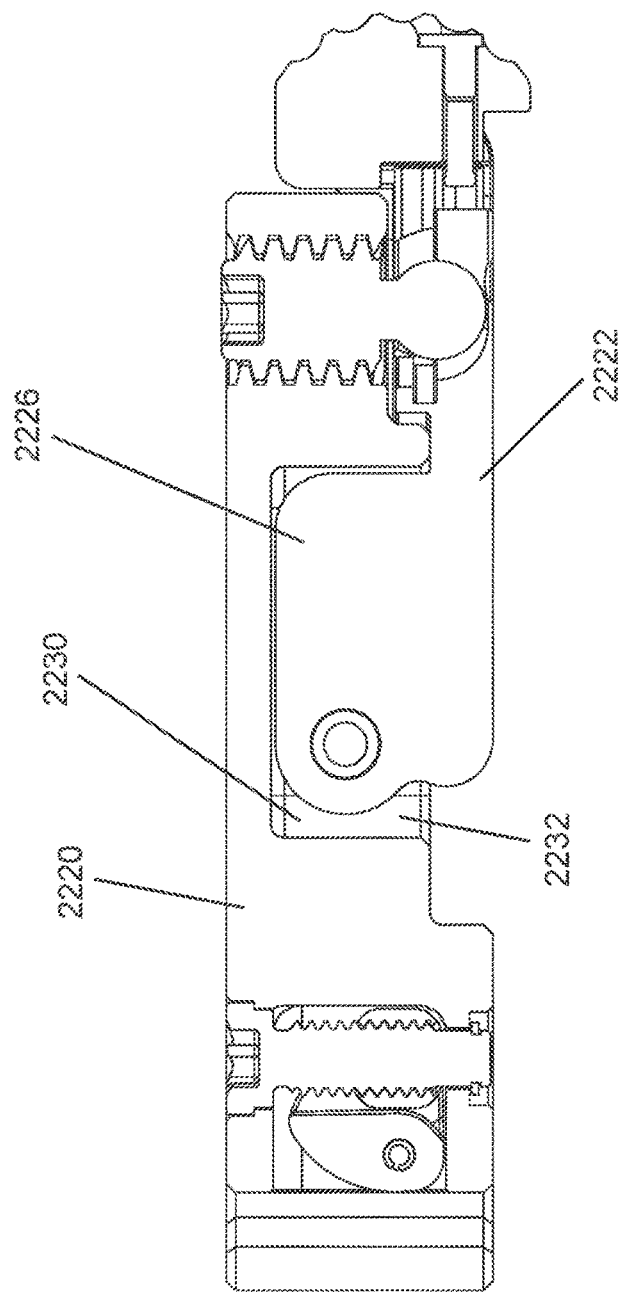
FIG. 65 is a cross-sectional view taken across line 65-65 in FIG. 64 showing a wall of an outer member of the slider received in a pocket of an inner member of the slider.
Figure 66:
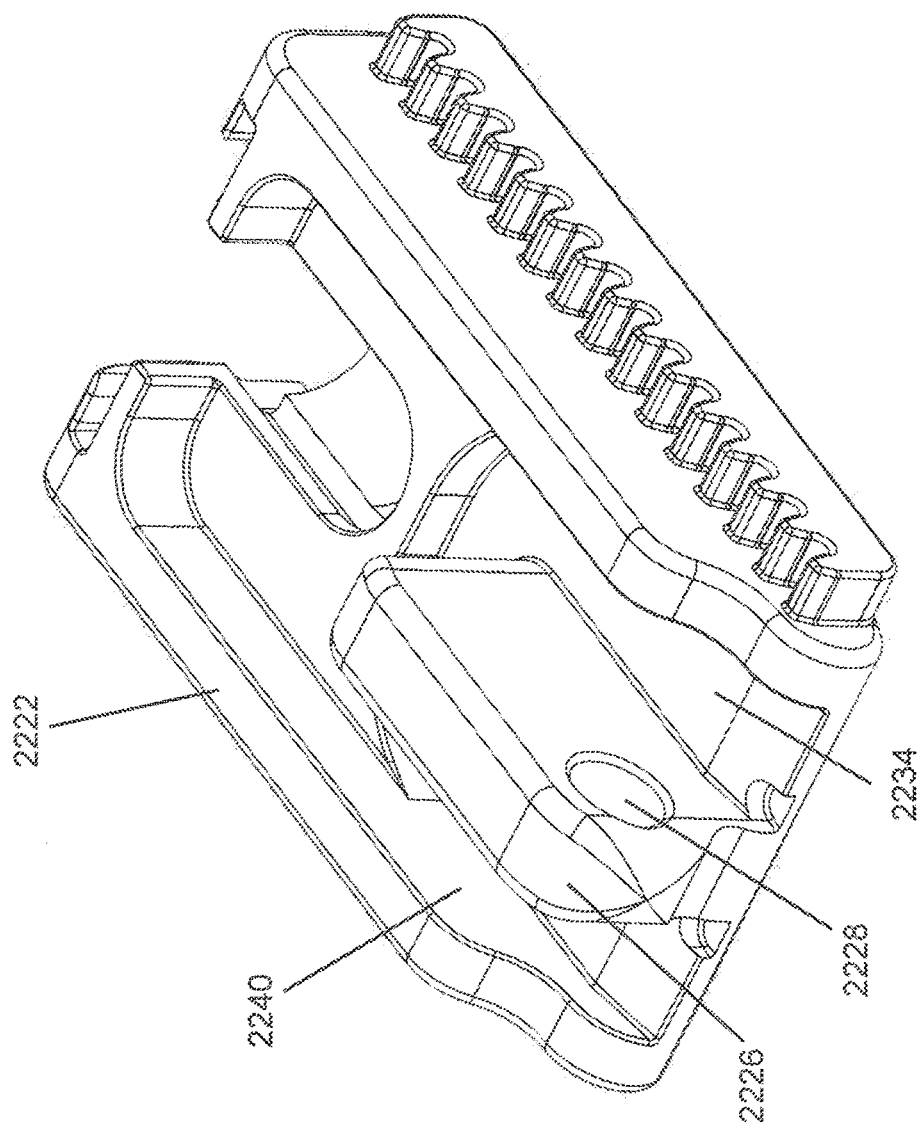
FIG. 66 is a perspective view of the outer member of the slider of FIG. 65 showing a through opening of the wall that receives a pivot pin to connect the outer member to the inner member of the slider.

With reference to FIGS. 65 and 66, the outer member 2222 has an upstanding wall 2226 that has a hole 2228 which receives the pivot pin 2224. The inner member 2220 includes a pocket 2230 that receives the wall 2226. The pocket 2230 has walls 2232 on opposite sides of the wall 2226 therebetween and guide the inner member 2220 as it pivots relative to the outer member 2222. Further, the outer member 2222 may have peripheral walls 2240 that further guide the inner member 2220 as the inner member 2220 pivots relative to the outer member 2222. Because the inner member 2220 and the outer member 2222 may be made of carbon fiber, the walls 2226, 2240, and 2232 are sized to provide sufficient rigidity to the material of the inner member 2220 and the outer member 2222 to resist fracture of the carbon fiber material.

Those skilled in the art will recognize that a wide variety of modifications, alterations, and combinations can be made with respect to the above described embodiments without departing from the spirit and scope of the invention, and that such modifications, alterations, and combinations, are to be viewed as being within the scope of the invention.

What is claimed is:

1. A retractor configured to enlarge an incision, the retractor comprising:
    a frame;
    a plurality of tissue engaging members configured for insertion into an incision;
    a plurality of sliders configured to connect the tissue engaging members to the frame, each slider being shiftable between an extended position and a retracted position,
    wherein each slider is selectively shiftable between the extended position and the retracted position; and
    a worm screw engaged with a worm gear and rotatable in a first direction to cause the worm gear to rotate in a retracting direction, the worm screw being rotatable in an opposite, second direction to cause the worm gear to rotate a drive member associated with one of the sliders in an extending direction.

2. The retractor of claim 1, wherein the worm gear is operatively coupled to the drive member, and wherein the worm screw is configured to be self-locking to inhibit unintended rotation of the drive member and lock at least one of the plurality of sliders in position relative to the frame.

3. The retractor of claim 1, wherein the worm gear is operatively couplable to the drive member and rotatable about a first axis, and wherein the worm screw is rotatable about a second axis perpendicular to the first axis.

4. The retractor of claim 1, wherein each of the plurality of sliders includes a second slider, the retractor further comprising:
    a second drive member associated with the second slider;
    a second worm gear operably coupled to the second drive member; and
    a second worm screw engaged with the second worm gear and rotatable in a third direction to rotate the second worm gear along with the drive member in a second retracting direction transverse to the retracting direction of the second slider, the second worm screw being rotatable in an opposite, fourth direction to rotate the second worm gear along with the second drive member in a second extending direction transverse to the extending direction of the second slider.

5. The retractor of claim 1, wherein one slider of the plurality includes a slider body slidably connected to the frame and a support pivotally connected to the slider body, the support having a tissue engaging member portion connectable to one of the tissue engaging members.

6. The retractor of claim 1, wherein one slider of the plurality includes:
    a pivotal support having a tissue engaging member portion configured to be connected to one of the tissue engaging members and an actuator portion spaced from the tissue engaging member portion; and
    a rotatable actuator connected to the actuator portion of the support and having a tool-receiving portion configured to receive a separate tool for rotating the actuator and causing the support and the one tissue engaging member connected thereto to pivot relative to the frame.

7. The retractor of claim 6, wherein the pivotal support is pivotal about a pivot axis intermediate the tissue engaging member and the actuator portion along the support.

8. The retractor of claim 7, wherein the pivot axis is closer to the tissue engaging member portion than the actuator portion along the support.

9. The retractor of claim 8, wherein the rotatable actuator and the slider body include a ball and socket that permits the rotatable actuator to pivot relative to the slider body with pivoting of the support and the tissue engaging member connected thereto.

10. The retractor of claim 7, wherein one slider of the plurality includes a slider body slidably connected to the frame and the support is pivotally connected to the slider body.

11. A retractor configured to enlarge an incision, the retractor comprising:
    a frame;
    a plurality of tissue engaging members configured for insertion into an incision;
    a plurality of operating mechanisms configured to move the tissue engaging members apart to enlarge the incision;
    a slider of one of the operating mechanisms connectable to one of the tissue engaging members, the slider being connected to the frame and shiftable between an extended position and a retracted position;
    a linear drive mechanism associated with the slider and including a drive member configured to cause the slider to selectively shift between the extended and retracted positions;
    a worm gear operatively coupled to the drive member;
    a tool-receiving member of the linear drive mechanism operably coupled to the drive member; and a clutch of the linear drive mechanism configured to permit the tool receiving member to turn relative to the drive member,
wherein the clutch is selectively disposable between a drive mode and a release mode.

12. The retractor of claim 11, wherein the clutch comprises a release shaft cooperatively configured with a release actuator to couple and decouple the worm gear from the drive member to dispose the clutch respectively in the drive mode and the release mode.

13. The retractor of claim 11, wherein the release shaft comprises a head operatively configured with at least one coupling member of the drive member.

14. The retractor of claim 13, wherein the at least one coupling member comprises a plurality of ball bearings disposed into pockets of the worm gear; the plurality of ball bearings disposable into a radially outward position extending into the pockets of the worm gear and a radially inward position wherein the plurality of ball bearings are spaced apart from the worm gear decoupling the drive member.

15. A retractor configured to enlarge an incision, the retractor comprising:
a frame;
a plurality of tissue engaging members configured for insertion into an incision;
a plurality of operating mechanisms configured to move the tissue engaging members apart to enlarge the incision;
a slider of one of the operating mechanisms connectable to one of the tissue engaging members, the slider being connected to the frame and selectively shiftable between extended and retracted positions;
a linear drive mechanism associated with the slider and including a drive member configured to cause the slider to shift to the retracted position;
a worm gear operatively coupled to the drive member;
a tool-receiving member of the linear drive mechanism operably coupled to the drive member; and
a clutch of the linear drive mechanism configured to permit the tool receiving member to turn relative to the drive member,
wherein the clutch is selectively disposable between a drive mode and a release mode,
wherein the clutch comprises a release shaft comprising a head operatively configured with at least one coupling member of the drive member, and
wherein the release shaft is operatively configured with a release actuator to couple and decouple the worm gear from the drive member to dispose the clutch respectively in the drive mode and the release mode.

* * * * *

UNITED STATES PATENT AND TRADEMARK OFFICE
CERTIFICATE OF CORRECTION

PATENT NO. : 12,408,909 B2
APPLICATION NO. : 18/658301
DATED : September 9, 2025
INVENTOR(S) : Scott J. Perrow, Bruce Anthony Riceman and Jacob Anton Colantonio It is certified that error appears in the above-identified patent and that said Letters Patent is hereby corrected as shown below:

In the Specification

In Column 4, Lines 3-4, the text "FIG. 5A is a cross-sectional view taken across the line 5A-5A in FIG. 5A" should read --FIG. 5A is a cross-sectional view taken across the line 5A-5A in FIG. 5--

In Column 4, Lines 5-9, the text "FIG. 6 is a perspective view of another one of the retractor blades of FIG. 1 showing a slot of the blade for slidably receiving a mounting rail of the guide dilator, the retractor blade of FIG. 6 lacking a cannula similar to the retractor blade of FIG. 5;" should read --FIG. 6 is a perspective view of another one of the retractor blades of FIG. 1 showing a slot of the blade for slidably receiving a mounting rail of the guide dilator;--

In Column 9, Lines 49-54, the text "In one form, axially extending surfaces of the flange 112 and the walls 196, 198 extend from a midline 199 of the blade 12 toward the distal end 36 of the blade 12 a distance that is at least a quarter of a blade length 210 (see FIG. 5) when the blade 12 is connected to the guide dilator 10." should read --In one form, axially extending surfaces of the flange 112 and the walls 196, 198 extend from a midline 199 of the blade 12 toward the distal end 34 of the blade 12 a distance that is at least a quarter of a blade length 210 (see FIG. 5) when the blade 12 is connected to the guide dilator 10.--

In Column 9, Lines 37-39, the text "The mounting rails 92, 96 have similar lower end walls 178, 180 for engaging stop surfaces on the retractor blades 80, 82, such as a stop surface 176 of the blade 14 (see FIG. 6)." should read --The mounting rails 92, 96 have similar lower end walls 178, 180 for engaging stop surfaces on the retractor blades 14, 18, such as a stop surface 176 of the blade 14 (see FIG. 6).--

In Column 10, Lines 27-29, the text "Like the blade 12, the blade 80 has a slot 220 with an open end 222, a closed end 224, and inwardly extending walls 226, 228 with serrations 230." should read --Like Signed and Sealed this
Twenty-seventh Day of January, 2026

John A. Squires
*Director of the United States Patent and Trademark Office* the blade 12, the blade 14 has a slot 220 with an open end 222, a closed end 224, and inwardly extending walls 226, 228 with serrations 230.--

In Column 13, Lines 5-3, the text "Fixation screws 676, 678 are tightened to engage blades 660, 662 with the operating mechanisms 642, 644." should read --Fixation screws 676, 678 are tightened to engage blades 650, 662 with the operating mechanisms 642, 644.--